(12) United States Patent
Harder et al.

(10) Patent No.: US 12,427,291 B2
(45) Date of Patent: Sep. 30, 2025

(54) IMPLANTABLE DEVICES FOR REDUCING PULSATILE PRESSURE WITHIN A BLOOD VESSEL

(71) Applicant: Aria CV, Inc., St. Paul, MN (US)

(72) Inventors: Lucas Harder, Minneapolis, MN (US); Lynn Zwiers, Lino Lakes, MN (US); Karl Vollmers, Minneapolis, MN (US); John Scandurra, St. Paul, MN (US); John Gainor, Mendota Heights, MN (US); Hendrik de Hoog, Robbinsdale, MN (US); Marc Knutson, Rogers, MN (US); Katherine Soojian, Rosemount, MN (US); Miles Wing, Ashby, MN (US)

(73) Assignee: Aria CV, Inc., St. Paul, MN (US)

( * ) Notice: Subject to any disclaimer, the term of this patent is extended or adjusted under 35 U.S.C. 154(b) by 1103 days.

(21) Appl. No.: 17/356,410

(22) Filed: Jun. 23, 2021

(65) Prior Publication Data
US 2021/0402159 A1    Dec. 30, 2021

Related U.S. Application Data

(60) Provisional application No. 63/044,337, filed on Jun. 25, 2020.

(51) Int. Cl.
| | | |
|---|---|---|
| *A61M 25/10* | (2013.01) | |
| *A61F 2/95* | (2013.01) | |
| *A61M 25/09* | (2006.01) | |

(52) U.S. Cl.
CPC ............ *A61M 25/104* (2013.01); *A61F 2/95* (2013.01); *A61F 2002/9505* (2013.01); *A61M 2025/09183* (2013.01); *A61M 2205/04* (2013.01)

(58) Field of Classification Search
CPC ...... A61M 25/104; A61M 2025/09183; A61M 2205/04; A61F 2/95; A61F 2002/9505
See application file for complete search history.

(56) References Cited

U.S. PATENT DOCUMENTS

| 3,275,001 A | 9/1966 | Rosecrans |
|---|---|---|
| 3,634,924 A | 1/1972 | Blake et al. |

(Continued)

FOREIGN PATENT DOCUMENTS

| CN | 102657910 A | 9/2012 |
|---|---|---|
| CN | 103260547 A | 8/2013 |

(Continued)

OTHER PUBLICATIONS

International Search Report & Written Opinion dated Nov. 29, 2021 in Int'l PCT Patent Appl. Serial No. PCT/US2021/038771.

(Continued)

*Primary Examiner* — Katherine M Rodjom
(74) *Attorney, Agent, or Firm* — Greenberg Traurig, LLP; Christopher C. Bolten; Albert K. Heng

(57) ABSTRACT

An implantable device for reducing pulsatile pressure within a blood vessel is described herein, for example to treat pulmonary hypertension. The implantable device may include a fluid reservoir, a compliant member (e.g., a balloon), and a conduit coupled to the fluid reservoir and the compliant member. Advanced designs for anchoring the compliant member in the blood vessel are described. In addition, enhanced reservoir, conduit, and balloon designs, as well as methods for implanting/using the same, are provided.

17 Claims, 58 Drawing Sheets

(56) References Cited

U.S. PATENT DOCUMENTS

| | | | |
|---|---|---|---|
| 3,818,903 A | 6/1974 | Bleecker | |
| 4,422,447 A | 12/1983 | Schiff | |
| 4,793,351 A | 12/1988 | Landman et al. | |
| 4,902,273 A | 2/1990 | Choy et al. | |
| 4,938,766 A | 7/1990 | Jarvik | |
| 4,955,905 A | 9/1990 | Reed | |
| 5,002,531 A | 3/1991 | Bonzel | |
| 5,112,303 A | 5/1992 | Pudenz et al. | |
| 5,222,980 A | 6/1993 | Gealow | |
| 5,409,444 A * | 4/1995 | Kensey | A61B 17/12109 600/16 |
| 5,486,192 A | 1/1996 | Walinsky et al. | |
| 5,496,311 A | 3/1996 | Abele et al. | |
| 5,578,085 A | 11/1996 | Johnson, Jr. et al. | |
| 5,713,867 A | 2/1998 | Morris | |
| 5,769,821 A | 6/1998 | Abrahamson et al. | |
| 5,795,325 A | 8/1998 | Valley et al. | |
| 5,814,016 A | 9/1998 | Valley et al. | |
| 5,820,542 A | 10/1998 | Dobak, III et al. | |
| 5,833,655 A | 11/1998 | Freed et al. | |
| 6,017,324 A | 1/2000 | Tu et al. | |
| 6,030,336 A | 2/2000 | Franchi | |
| 6,039,744 A * | 3/2000 | Forber | A61F 2/95 606/108 |
| 6,053,891 A | 4/2000 | DeCampli | |
| 6,136,025 A | 10/2000 | Barbut et al. | |
| 6,210,318 B1 | 4/2001 | Lederman | |
| 6,261,304 B1 | 7/2001 | Hall et al. | |
| 6,371,971 B1 * | 4/2002 | Tsugita | A61F 2/0108 606/200 |
| 6,461,367 B1 | 10/2002 | Kirsch et al. | |
| 6,558,349 B1 | 5/2003 | Kirkman | |
| 6,559,349 B1 | 5/2003 | Slaugh et al. | |
| 6,576,007 B2 | 6/2003 | Dehdashtian et al. | |
| 6,579,224 B1 | 6/2003 | Burton et al. | |
| 6,682,473 B1 | 1/2004 | Matsuura et al. | |
| 7,044,967 B1 | 5/2006 | Solem et al. | |
| 7,074,178 B2 | 7/2006 | Connors et al. | |
| 7,468,050 B1 | 12/2008 | Kantrowitz | |
| 7,540,876 B2 | 6/2009 | Connors et al. | |
| 7,766,814 B2 | 8/2010 | Walsh | |
| 7,811,249 B2 | 10/2010 | Saab | |
| 7,928,367 B2 | 4/2011 | Hirota et al. | |
| 8,016,740 B2 | 9/2011 | Connors et al. | |
| 8,092,521 B2 | 1/2012 | Figulla et al. | |
| 8,116,883 B2 | 2/2012 | Williams et al. | |
| 8,206,378 B1 | 6/2012 | Kalpin et al. | |
| 8,585,572 B2 | 11/2013 | Mehmanesh | |
| 8,747,386 B2 | 6/2014 | Rykhus, Jr. et al. | |
| 8,876,850 B1 * | 11/2014 | Vollmers | A61M 25/104 606/191 |
| 8,882,653 B2 | 11/2014 | Gillespie, Jr. et al. | |
| 8,956,379 B2 | 2/2015 | Luciano et al. | |
| 9,017,359 B2 | 4/2015 | Scandurra et al. | |
| 9,039,725 B1 | 5/2015 | Vollmers et al. | |
| 9,107,992 B2 | 8/2015 | Kushwaha et al. | |
| 9,242,082 B2 | 1/2016 | Vollmers et al. | |
| 9,333,328 B2 | 5/2016 | Scandurra et al. | |
| 9,610,391 B2 | 4/2017 | Vollmers et al. | |
| 9,801,989 B2 | 10/2017 | Vollmers et al. | |
| 9,987,153 B2 | 6/2018 | Scandurra et al. | |
| 10,327,880 B2 | 6/2019 | Connors et al. | |
| 10,350,397 B2 | 7/2019 | Scandurra et al. | |
| 10,376,681 B2 | 8/2019 | Bak-Boychuk et al. | |
| 10,617,538 B2 | 4/2020 | Scandurra et al. | |
| 10,682,448 B2 | 6/2020 | Vollmers et al. | |
| 10,702,682 B2 | 7/2020 | Scandurra et al. | |
| 10,751,519 B2 | 8/2020 | Scandurra et al. | |
| 11,141,581 B2 | 10/2021 | Vollmers et al. | |
| 11,331,105 B2 | 5/2022 | Gainor et al. | |
| 11,406,803 B2 | 8/2022 | Scandurra et al. | |
| 11,511,089 B2 | 11/2022 | Vollmers et al. | |
| 11,583,420 B2 | 2/2023 | Scandurra et al. | |
| 11,833,343 B2 | 12/2023 | Vollmers et al. | |
| 11,938,291 B2 | 3/2024 | Scandurra et al. | |
| 11,992,636 B2 | 5/2024 | Vollmers et al. | |
| 2001/0023332 A1 | 9/2001 | Hahnen | |
| 2003/0055465 A1 | 3/2003 | Ben-Haim et al. | |
| 2003/0208259 A1 | 11/2003 | Penhasi | |
| 2004/0093007 A1 | 5/2004 | Sussman et al. | |
| 2004/0106971 A1 | 6/2004 | Schwartz et al. | |
| 2004/0111006 A1 | 6/2004 | Alferness et al. | |
| 2004/0143319 A1 | 7/2004 | Schwartz et al. | |
| 2004/0210304 A1 | 10/2004 | Seguin et al. | |
| 2005/0015107 A1 | 1/2005 | O'Brien | |
| 2005/0059965 A1 | 3/2005 | Eberl et al. | |
| 2005/0070938 A1 | 3/2005 | Copa et al. | |
| 2005/0131451 A1 | 6/2005 | Kleshinski et al. | |
| 2005/0251175 A1 | 11/2005 | Weisenburgh et al. | |
| 2005/0267596 A1 | 12/2005 | Chen et al. | |
| 2006/0085028 A1 | 4/2006 | Boock | |
| 2006/0093642 A1 | 5/2006 | Ranade | |
| 2006/0106450 A1 | 5/2006 | Ben Muvhar | |
| 2006/0129083 A1 | 6/2006 | Brenneman et al. | |
| 2006/0135962 A1 | 6/2006 | Kick et al. | |
| 2006/0155310 A1 | 7/2006 | Binmoeller | |
| 2006/0241745 A1 | 10/2006 | Solem | |
| 2006/0253095 A1 | 11/2006 | Stull | |
| 2007/0142819 A1 | 6/2007 | El-Nounou et al. | |
| 2007/0156013 A1 | 7/2007 | Birk | |
| 2007/0156167 A1 | 7/2007 | Connors et al. | |
| 2007/0293848 A1 | 12/2007 | Endo et al. | |
| 2008/0114338 A1 | 5/2008 | Kumar | |
| 2008/0132750 A1 | 6/2008 | Miller | |
| 2008/0147181 A1 | 6/2008 | Ghione et al. | |
| 2008/0194905 A1 | 8/2008 | Walsh | |
| 2008/0195174 A1 | 8/2008 | Walker et al. | |
| 2008/0243093 A1 | 10/2008 | Kalpin et al. | |
| 2008/0312679 A1 | 12/2008 | Hardert et al. | |
| 2009/0143837 A1 | 6/2009 | Rossing et al. | |
| 2009/0222083 A1 | 9/2009 | Nguyen et al. | |
| 2009/0240277 A1 | 9/2009 | Connors et al. | |
| 2009/0294031 A1 | 12/2009 | Pepper et al. | |
| 2010/0042070 A1 | 2/2010 | Gill et al. | |
| 2010/0099945 A1 | 4/2010 | Birk et al. | |
| 2010/0185049 A1 | 7/2010 | Birk et al. | |
| 2010/0197994 A1 | 8/2010 | Mehmanesh | |
| 2010/0204590 A1 | 8/2010 | Hatib et al. | |
| 2010/0274221 A1 | 10/2010 | Sigg et al. | |
| 2010/0324472 A1 | 12/2010 | Wulfman | |
| 2010/0331767 A1 | 12/2010 | Frankowski et al. | |
| 2011/0124951 A1 | 5/2011 | Walsh | |
| 2011/0137210 A1 | 6/2011 | Johnson | |
| 2011/0137428 A1 | 6/2011 | Terliuc | |
| 2012/0053514 A1 | 3/2012 | Robinson et al. | |
| 2012/0083646 A1 | 4/2012 | Benson | |
| 2012/0172654 A1 | 7/2012 | Bates | |
| 2013/0079871 A1 | 3/2013 | Scandurra et al. | |
| 2013/0165964 A1 | 6/2013 | Vollmers et al. | |
| 2013/0245665 A1 | 9/2013 | Scandurra et al. | |
| 2014/0214149 A1 | 7/2014 | Kuraguntla et al. | |
| 2014/0228878 A1 | 8/2014 | Scandurra et al. | |
| 2014/0370246 A1 | 12/2014 | Hurt | |
| 2015/0196303 A1 | 7/2015 | Seguin | |
| 2015/0216531 A1 | 8/2015 | Seguin | |
| 2015/0282859 A1 | 10/2015 | Bencini et al. | |
| 2015/0352335 A1 | 12/2015 | Moeller | |
| 2015/0366652 A1 | 12/2015 | Connors | |
| 2016/0082169 A1 | 3/2016 | Scandurra et al. | |
| 2016/0144091 A1 | 5/2016 | Breedon et al. | |
| 2016/0237237 A1 | 8/2016 | Tour et al. | |
| 2016/0310306 A1 | 10/2016 | Brister et al. | |
| 2018/0036464 A1 | 2/2018 | Vollmers et al. | |
| 2018/0368854 A1 * | 12/2018 | Kleshinski | A61B 17/12145 |
| 2019/0192835 A1 | 6/2019 | Scandurra et al. | |
| 2020/0046369 A1 | 2/2020 | Gainor et al. | |
| 2020/0205738 A1 * | 7/2020 | Adawi | A61B 5/028 |
| 2020/0306435 A1 | 10/2020 | Vollmers et al. | |
| 2020/0368507 A1 | 11/2020 | Scandurra et al. | |
| 2021/0069396 A1 | 3/2021 | Vollmers et al. | |

(56) References Cited

U.S. PATENT DOCUMENTS

| | | | |
|---|---|---|---|
| 2021/0196462 A1* | 7/2021 | Khairkhahan | ........ A61F 2/2445 |
| 2021/0298763 A1* | 9/2021 | Stahmann | ........ A61B 17/12122 |

FOREIGN PATENT DOCUMENTS

| | | |
|---|---|---|
| DE | 19508129 A1 | 9/1996 |
| DE | 19508129 C2 | 2/1997 |
| DE | 102005060197 A1 | 6/2007 |
| EP | 0366814 A1 | 5/1990 |
| EP | 0959912 A1 | 12/1999 |
| EP | 0959912 B1 | 9/2004 |
| EP | 2016961 A1 | 1/2009 |
| EP | 2016961 B1 | 2/2010 |
| FR | 3016279 A1 | 7/2015 |
| FR | 3017044 A1 | 8/2015 |
| JP | 2005538807 A | 12/2005 |
| JP | 2007526039 A | 9/2007 |
| JP | 2009502247 A | 1/2009 |
| JP | 2009509650 A | 3/2009 |
| WO | WO-9004430 A1 | 5/1990 |
| WO | WO-9006086 A1 | 6/1990 |
| WO | WO-9317731 A1 | 9/1993 |
| WO | WO-9510317 A1 | 4/1995 |
| WO | WO-9532018 A1 | 11/1995 |
| WO | WO-9600095 A1 | 1/1996 |
| WO | WO-9612518 A1 | 5/1996 |
| WO | WO-9634647 A1 | 11/1996 |
| WO | WO-9850100 A1 | 11/1998 |
| WO | WO-9904833 A1 | 2/1999 |
| WO | WO-0066030 A1 | 11/2000 |
| WO | WO-0236048 A1 | 5/2002 |
| WO | WO-2004026112 A2 | 4/2004 |
| WO | WO-2004080338 A2 | 9/2004 |
| WO | WO-2005084730 A1 | 9/2005 |
| WO | WO-2006020942 A1 | 2/2006 |
| WO | WO-2006067473 A1 | 6/2006 |
| WO | WO-2007014028 A1 | 2/2007 |
| WO | WO-2007038476 A2 | 4/2007 |
| WO | WO-2007059594 A1 | 5/2007 |
| WO | WO-2008154145 A1 | 12/2008 |
| WO | WO-2010022173 A1 | 2/2010 |
| WO | WO-2010129089 A2 | 11/2010 |
| WO | WO-2010129089 A4 | 3/2011 |
| WO | WO-2012071395 A1 | 5/2012 |
| WO | WO-2013109891 A1 | 7/2013 |
| WO | WO-2013148697 A1 | 10/2013 |
| WO | WO-2013185138 A1 | 12/2013 |
| WO | WO-2015102693 A2 | 7/2015 |
| WO | WO-2015107434 A1 | 7/2015 |
| WO | WO-2015114471 A1 | 8/2015 |
| WO | WO-2015133849 A1 | 9/2015 |
| WO | WO-2018075552 A1 | 4/2018 |

OTHER PUBLICATIONS

U.S. Appl. No. 13/701,721 / U.S. Pat. No. 9,987,153, filed May 31, 2011 / Jun. 5, 2018.
U.S. Appl. No. 13/884,169 / U.S. Pat. No. 9,017,359, filed Nov. 22, 2011 / Apr. 28, 2015.
U.S. Appl. No. 14/253,127 / U.S. Pat. No. 9,333,328, filed Apr. 15, 2014 / May 10, 2016.
U.S. Appl. No. 14/309,758 / U.S. Pat. No. 8,876,850, filed Jun. 19, 2014 / Nov. 4, 2014.
U.S. Appl. No. 14/531,846 / U.S. Pat. No. 9,039,725, filed Nov. 3, 2014 / May 26, 2015.
U.S. Appl. No. 14/710,180 / U.S. Pat. No. 9,242,082, filed May 12, 2015 / Jan. 26, 2016.
U.S. Appl. No. 14/955,109 / U.S. Pat. No. 10,751,519, filed Dec. 1, 2015 / Aug. 25, 2020.
U.S. Appl. No. 14/956,127 / U.S. Pat. No. 10,350,397, filed Dec. 1, 2015 / Jul. 16, 2019.
U.S. Appl. No. 14/990,627 / U.S. Pat. No. 9,610,391, filed Jan. 7, 2016 / Apr. 4, 2017.
U.S. Appl. No. 15/474,902 / U.S. Pat. No. 9,801,989, filed Mar. 30, 2017 / Oct. 31, 2017.
U.S. Appl. No. 15/785,304 / U.S. Pat. No. 10,682,448, filed Oct. 16, 2017 / Jun. 16, 2020.
U.S. Appl. No. 15/993,572 / U.S. Pat. No. 10,617,538, filed May 30, 2018 / Apr. 14, 2020.
U.S. Appl. No. 16/288,088 / U.S. Pat. No. 10,702,682, filed Feb. 27, 2019 / Jul. 7, 2020.
U.S. Appl. No. 16/342,968, filed Apr. 17, 2019.
U.S. Appl. No. 16/842,612, filed Apr. 7, 2020.
U.S. Appl. No. 16/900,794, filed Jun. 12, 2020.
U.S. Appl. No. 16/989,830, filed Aug. 10, 2020.
U.S. Appl. No. 17/011,870, filed Sep. 3, 2020.
"Aria CV Awarded Top Prize At TCT's 2018 Shark Tank Competition",https://cathlabdigest.com/content/Aria-CV-Awarded-Top-Prize-TCT's-2018-Shark-Tank-Competition, dated Oct. 9, 2018, (accessed Dec. 13, 2019).
"Aria CV Wins Contest for Pulmonary Arterial Hypertension Medical Device, "https ://pulmonaryhypertensionnews.com/2018/09/27/aria-cv-wins-contest-pulmonary-arterial-hypertension-medical-device/, dated Sep. 27, 2018, (accessed Dec. 13, 2019).
"Aria CV Wins top honors in device organization Shark Tank Competition," http://www.startribune.com/loe-carlson/271816721, dated Apr. 22, 2019, (accessed Dec. 13, 2019).
Borlaug, et al., Ventricular-Vascular Interaction in Heart Failure, Heart Failure Clinics, 4(1):23-36 (2008).
Brian, Jr., M.D., Johnny E., Associate Professor, Department of Anesthesia, University of Iowa College of Medicine, "Gas Exchange, Partial Pressure Gradients, and the Oxygen Window," Oct. 2001.
Elzinga, et al., Left and Right Ventricular Pump Function and Consequences of Having Two Pumps in One Heart, Circ. Res, 46:564-574 (1980).
Elzinga, et al., Pressure and Flow Generated by the Left Ventricle Against Different Impedances, Circulation Research, 32(2): 178-186 (1973).
Extended European Search Report dated Mar. 1, 2017 in EP Patent Appl. Serial No. EP11792905.9. (0430).
Extended European Search Report dated Feb. 6, 2018 in EP Patent Appl. Serial No. 11843546.0, 7 pages (0230).
Extended European Search Report dated Jun. 19, 2019 in EP Patent Appl. Serial No. EP19165162.9, 5 pages (0335).
Grant, et al., Clinical Significance of Pulmonary Arterial Input Impedance, European Respiratory Journal, 9(11):2196-2199 (1996).
Harnek, et al., Transcatheter Implantation of the Monarc Coronary Sinus Device for Mitral Regurgitation: 1-Year Results from the Evolution Phase I Study (Clinical Evaluation of the Edwards Lifesciences Percutaneous Mitral Annuloplasty System for the Treatment of Mitral Regurgitation), JACC: Cardiovascular Interventions 4.1 (2011): 115-122 (2011).
International Search Report & Written Opinion dated Nov. 27, 2020 in Int'l PCT Patent Appl. Serial No. PCT/US2020/049252 (0710).
International Search Report & Written Opinion dated Jan. 31, 2018 in Int'l PCT Patent Application Serial No. PCT/US2017/057035 (0510).
International Search Report and Written Opinion dated Dec. 22, 2015 in Int'l PCT Patent Application Serial No. PCT/US2015/036201 (0310).
International Search Report dated Sep. 8, 2011 in PCT Patent Application No. PCT/US2011/38558 (0410).
Lammers, et al., Mechanics and Function of the Pulmonary Vasculature: Implications For Pulmonary Vascular Disease and Right Ventricular Function, Comprehensive Physiology, 2:295-319 (2012).
Lankhaar, et al., Pulmonary Vascular Resistance and Compliance Stay Inversely Related During Treatment of Pulmonary Hypertension, European Heart Journal, 29:1688-1695 (2008).
Lategola, Michael T., Measurement of Total Pressure of Dissolved Gas in Mammalian Tissue In Vivo, J.Appi.Physiol., 19:322-4 (1964).
Loring, Stephen H., et al., Gas Exchange in Body Cavities, Handbook of Physiology- The Respiratory System IV, Chapter 15, pp. 283-295 (1987).
Mahapatra, et al., Relationship of Pulmonary Arterial Capacitance and Mortality in Idiopathic Pulmonary Arterial Hypertension, Journal of the American College of Cardiology, 47(4), 799-803 (2006).

(56) References Cited

OTHER PUBLICATIONS

Naeije, et al., Right Ventricular Function in Pulmonary Hypertension: Physiological Concepts, European heart journal supplements, 9.suppl H: H5-H9 (2007).
PCT International Search Report and Written Opinion dated Mar. 24, 2015 for PCT/IB/2015/050068.
PCT International Search Report and Written Opinion dated Mar. 24, 2015 in Int'l PCT Patent Appl. No. PCT/IB/2015/050066.
PCT International Search Report dated Mar. 8, 2012 in International PCT Patent Application Serial No. PCT/US11/061815 (0210).
Pellegrini, et al., Prognostic Relevance of Pulmonary Arterial Compliance in Patients With Chronic Heart Failure, Chest, Original Research, Pulmonary Vascular Disease, 145(5):1064-1070 (2014).
Piiper, Johannes, Physiological Equilibria of Gas Cavities in the Body, Handbook of Physiology. Section 3: Respiration, vol. II, pp. 1205-1218 (1965).
Procyrion., A tool for the Cardiologist, published Jul. 3, 2013. http://web.archive.org/web/20130703020540/http://www.procyrion.com/techno- logy.
Reuben, S. R., Compliance of the Human Pulmonary Arterial System in Disease, Circulation Research, 29(1), 40-50 (1971).
Saouti, et al., The Arterial Load in Pulmonary Hypertension, European Respiratory Review, 19(117):197-203 (2010).
Second Written Opinion dated Jul. 7, 2016 in Int'l PCT Patent Application Serial No. PCT/US2015/036201 (0310).
Souza, Rogerio., Assessment of Compliance in Pulmonary Arterial Hypertension, European Heart Journal, 29:1603-1604 (2008).
Sunagawa, et al., Left Ventricular Interaction with Arterial Load Studied in Isolated Canine Ventricle, American Journal of Physiology—Heart and Circulatory Physiology, 245(5), H773-H780 (1983).
Tenney, et al., Gas Transfers in a Sulfur Hexafluoride Pneumoperitoneum, Journal of Applied Physiology, 6(4):201-208 (1953).
Tucker, et al., Inert Gas Exchange in Subcutaneous Gas Pockets of Air-Breathing Animals: Theory and Measurement, Respiration Physiology, 1:151-171 (1966).
Wang, et al., Pulmonary Vascular Wall Stiffness: an Important Contributor to the Increased Right Ventricular Afterload with Pulmonary Hypertension, Pulmonary circulation, 1(2), 212-223 (2011).
Written Opinion dated Mar. 8, 2012 in International PCT Patent Application Serial No. PCT/US11/061815 (0210).
Written Opinion dated Sep. 8, 2011 in International PCT Patent Application Serial No. PCT/US11/038558 (0410).

\* cited by examiner

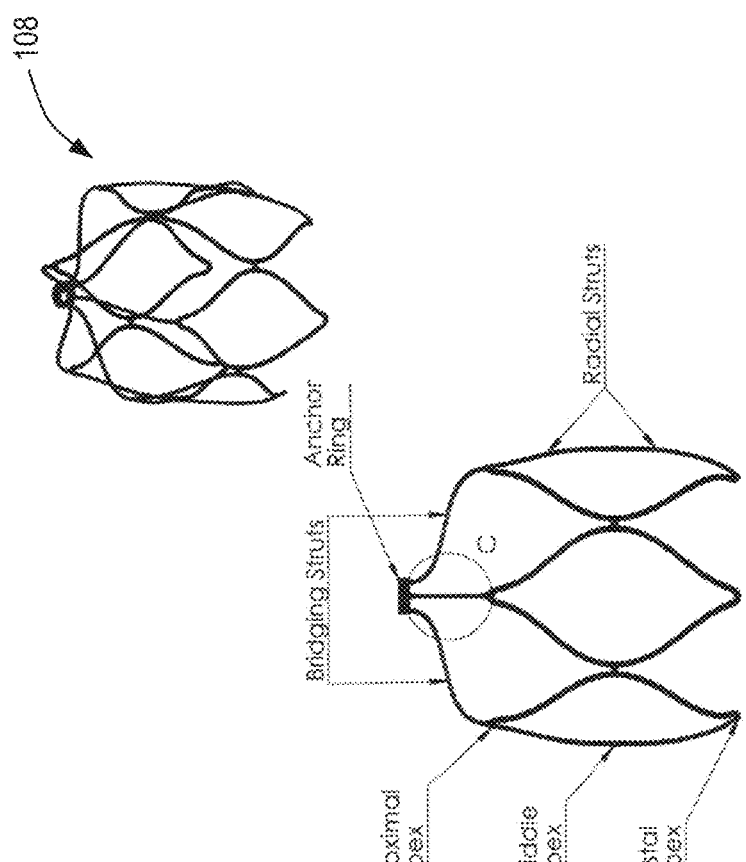
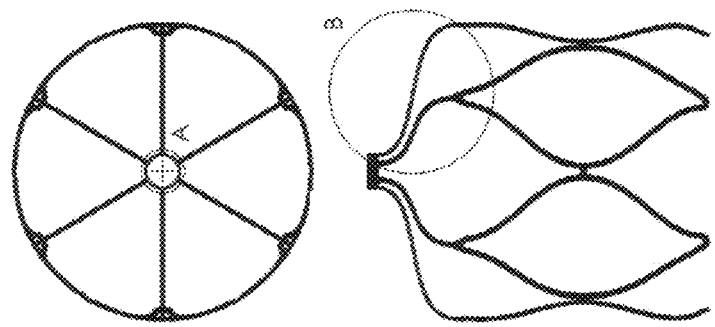
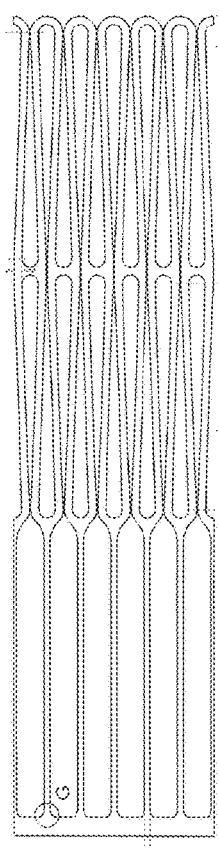
FIG. 2J
FIG. 2K
FIG. 2L

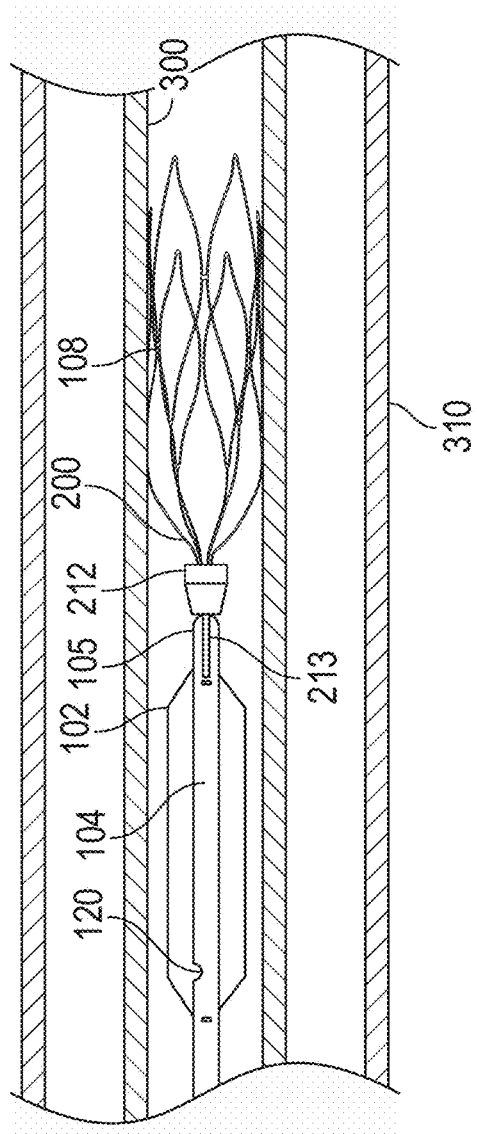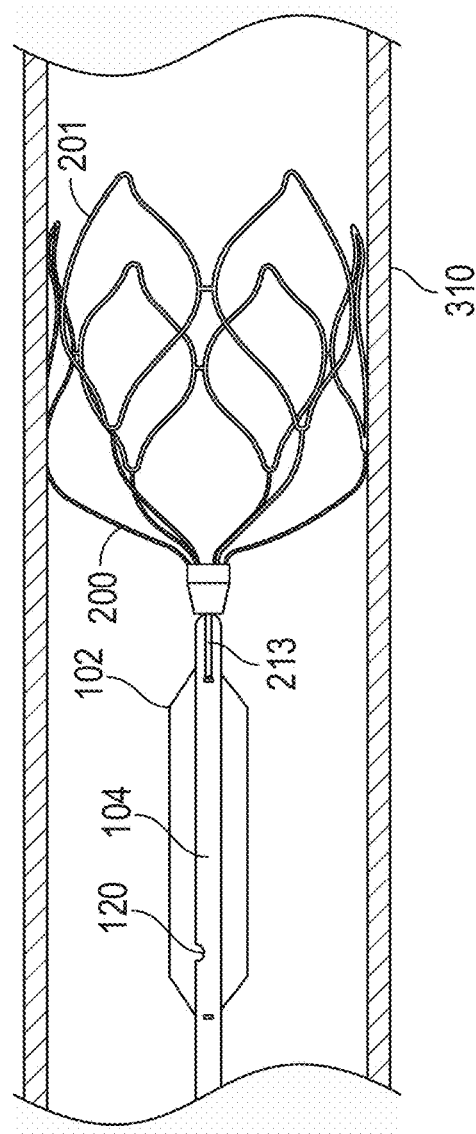

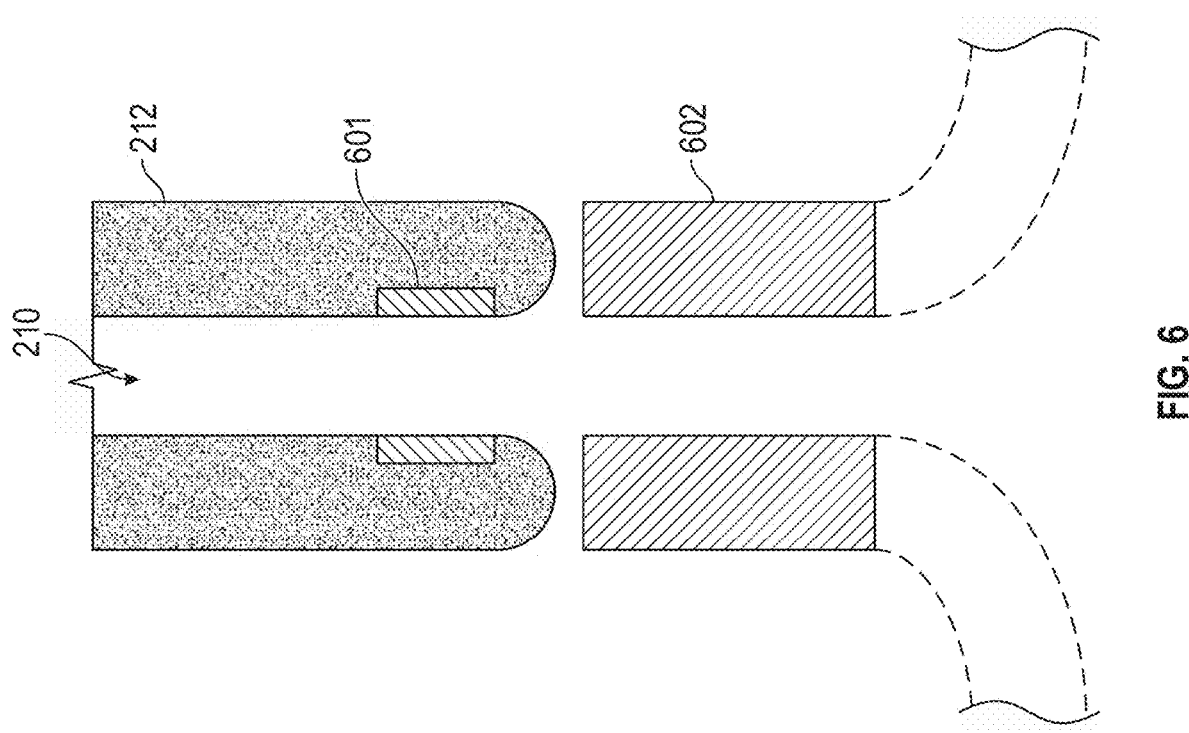

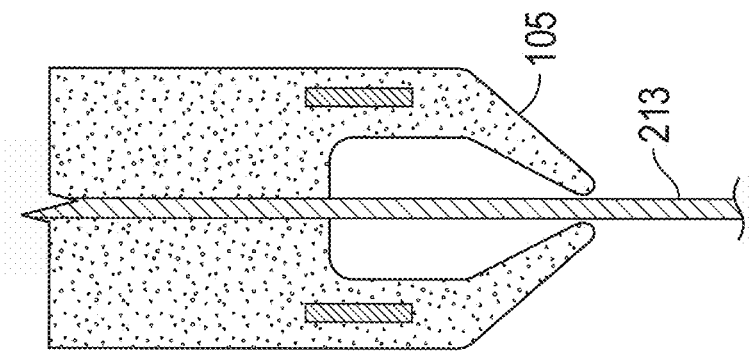
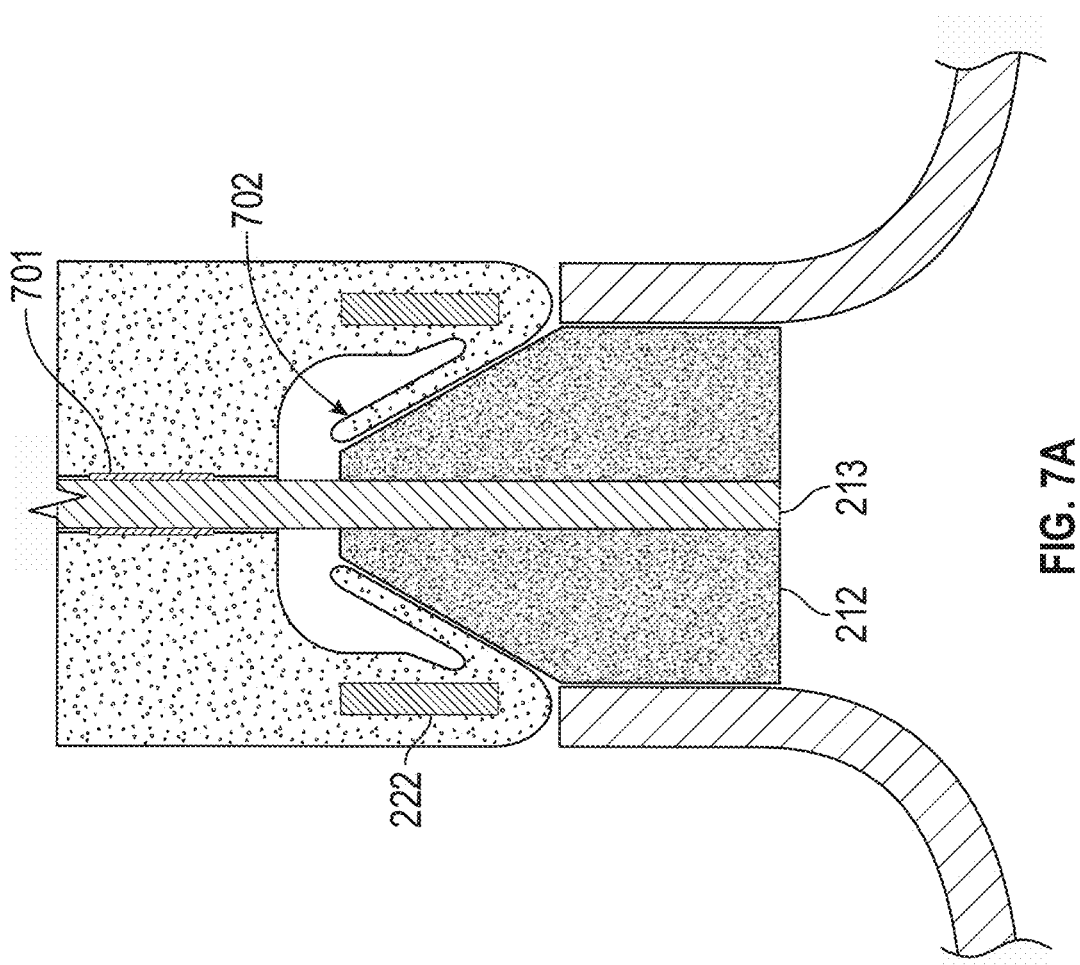
FIG. 7A
FIG. 7B

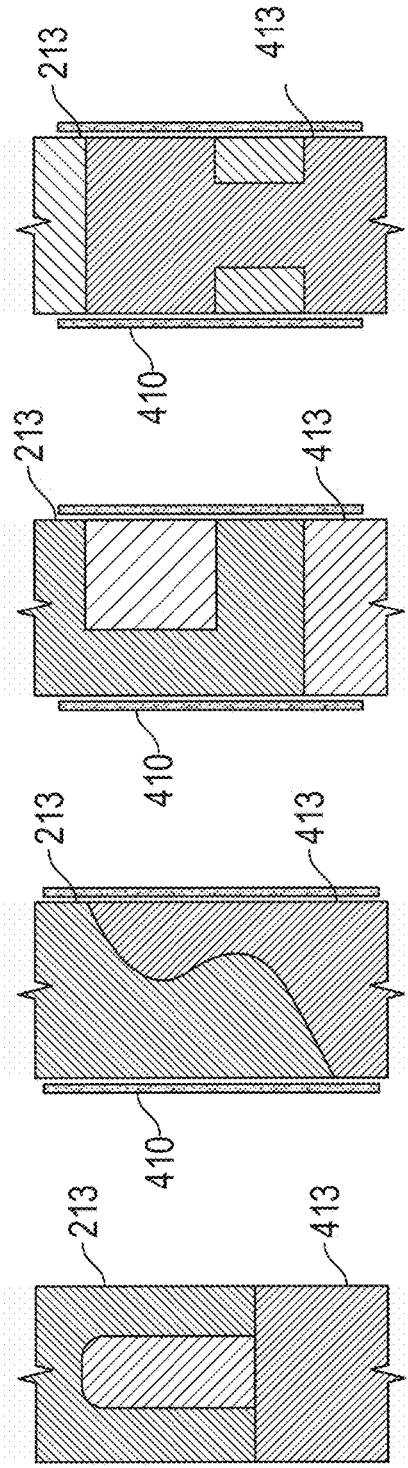
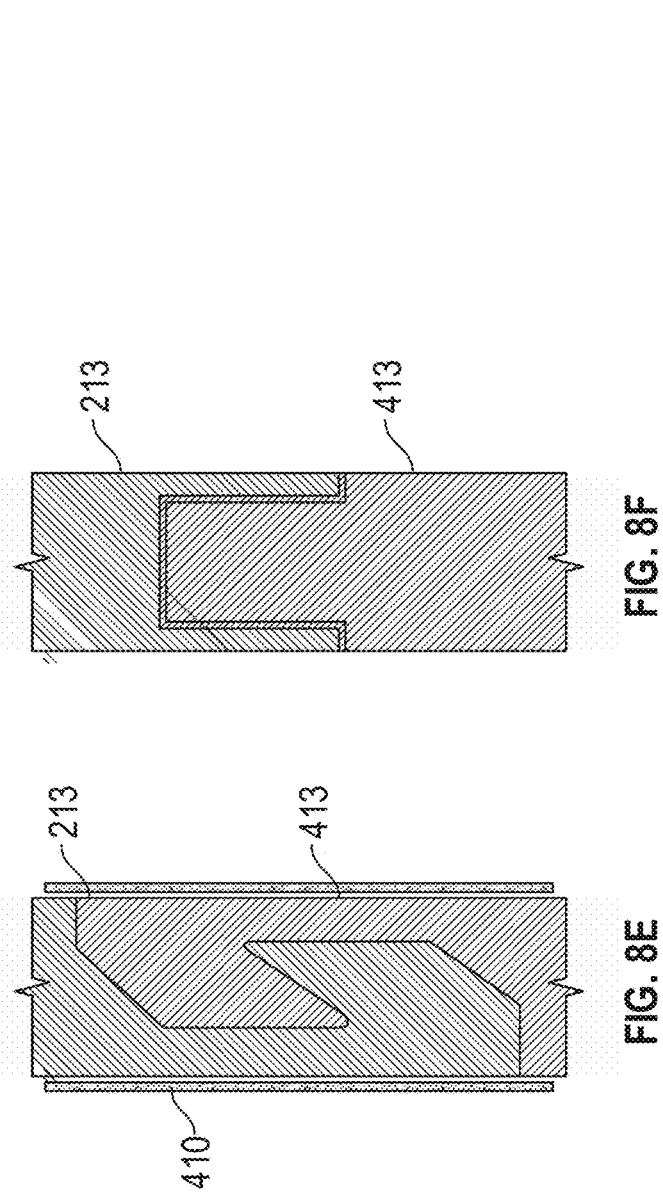

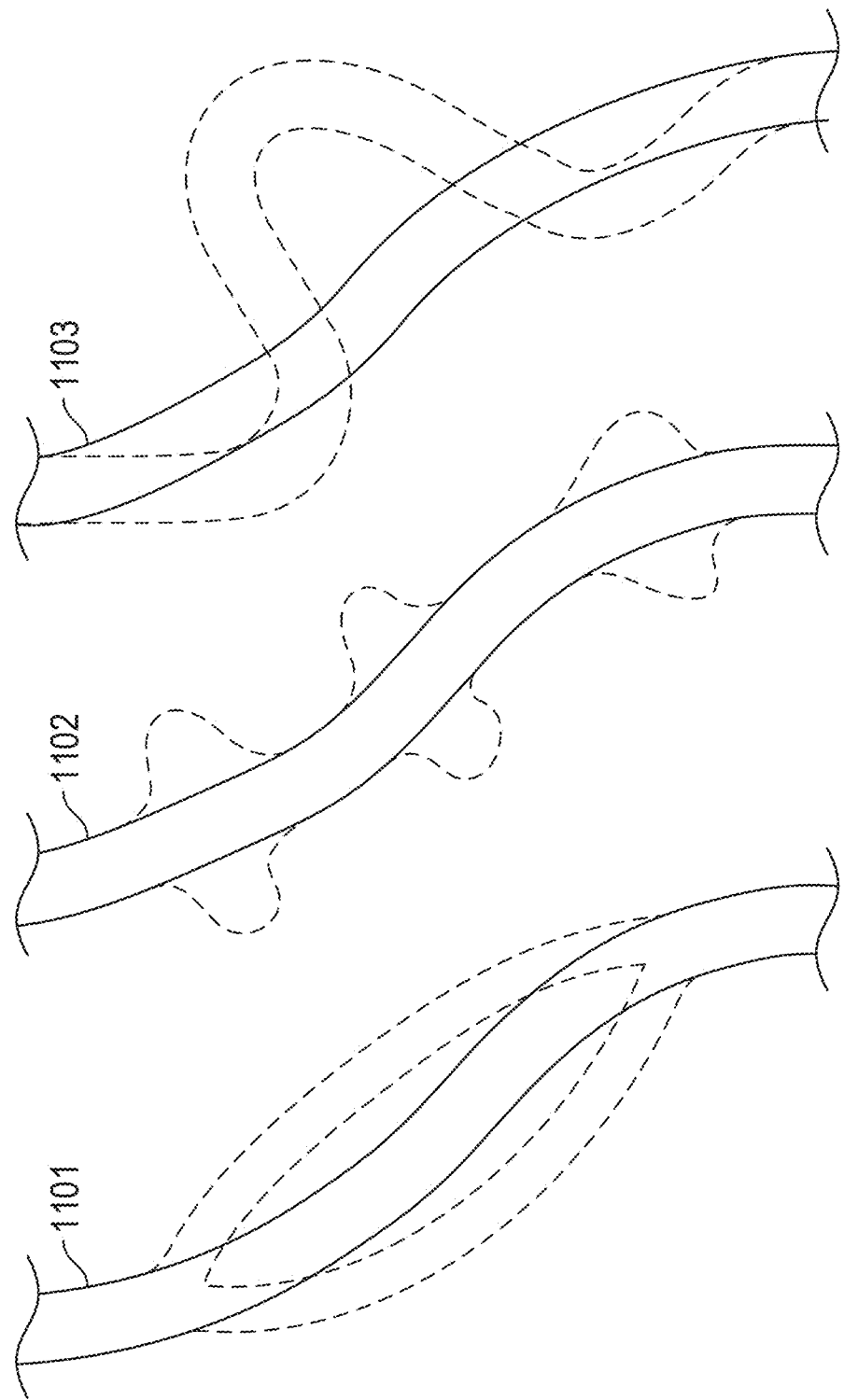

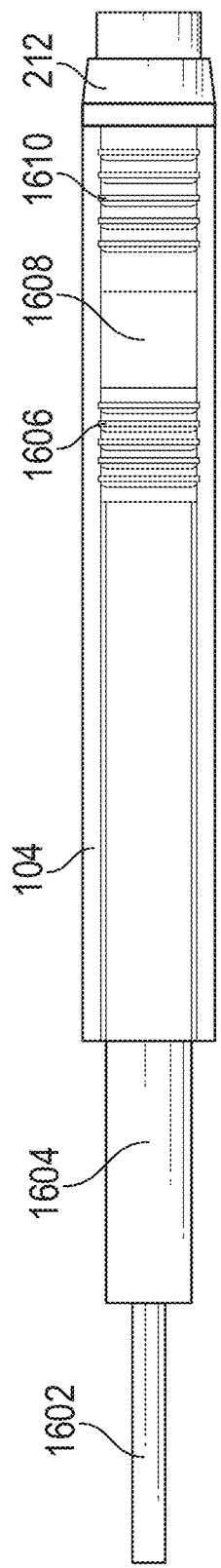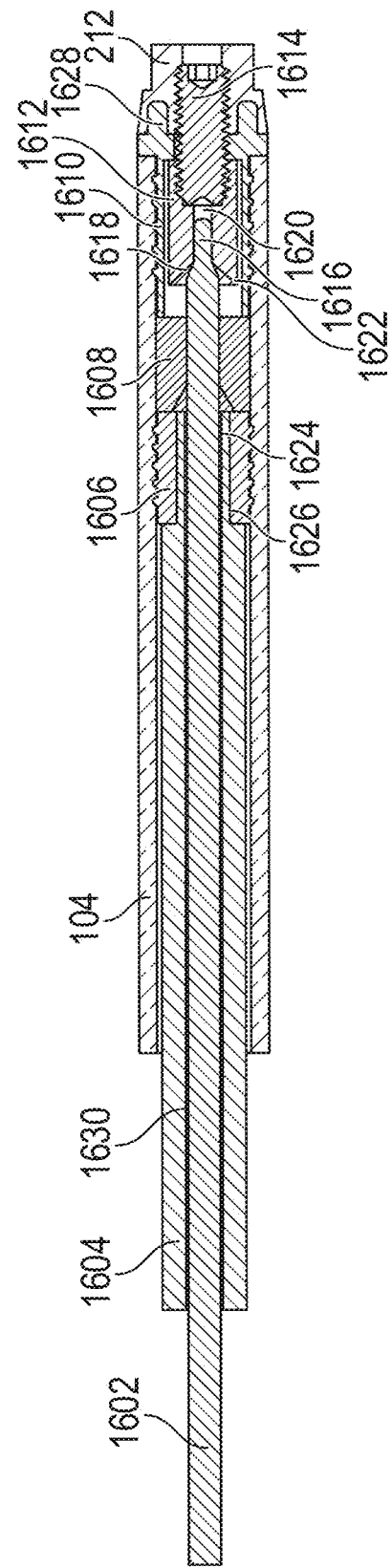

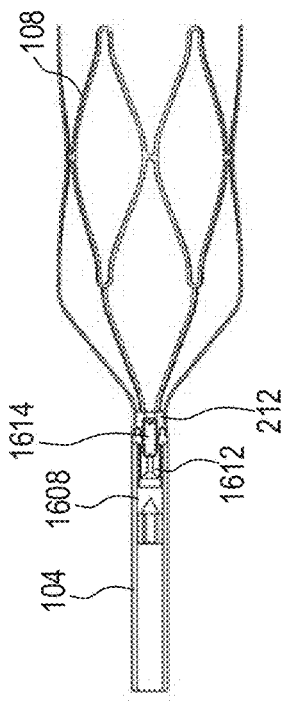 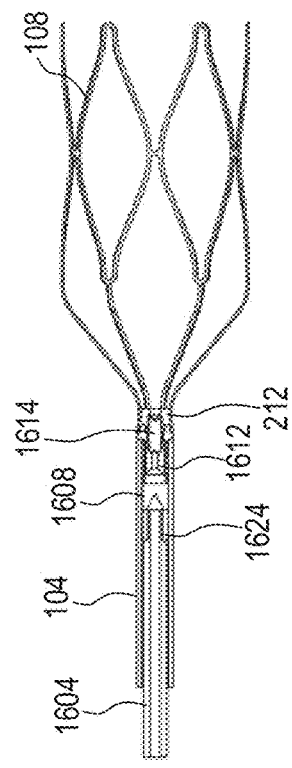 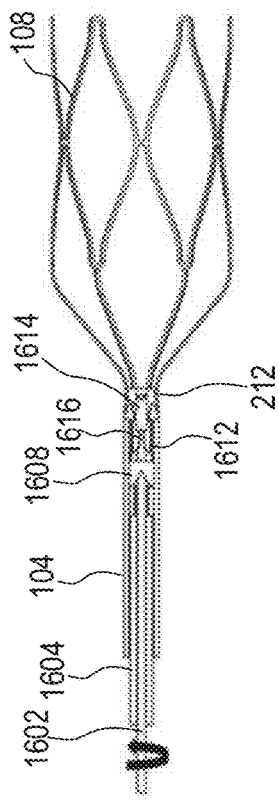
FIG. 17A  FIG. 17B  FIG. 17C
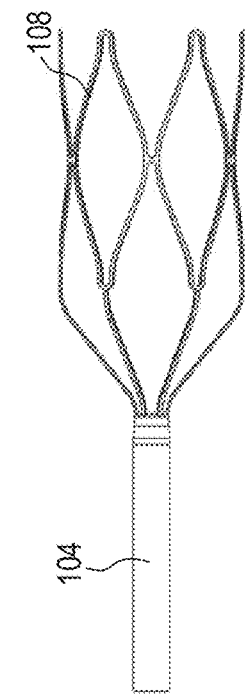 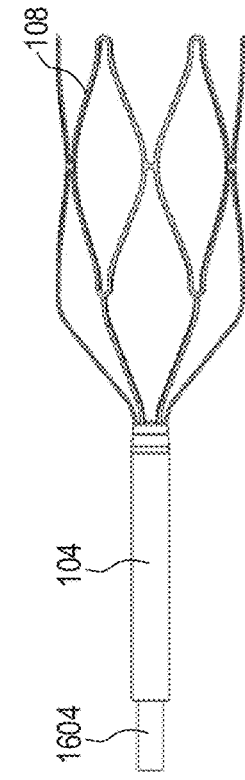 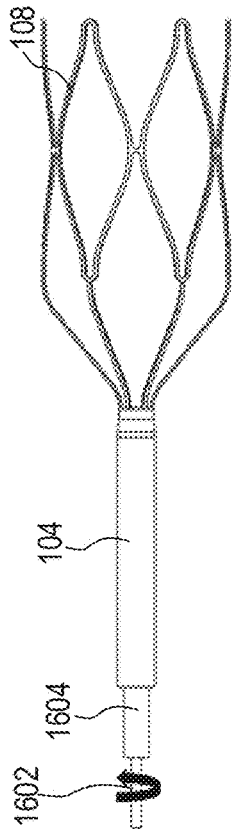

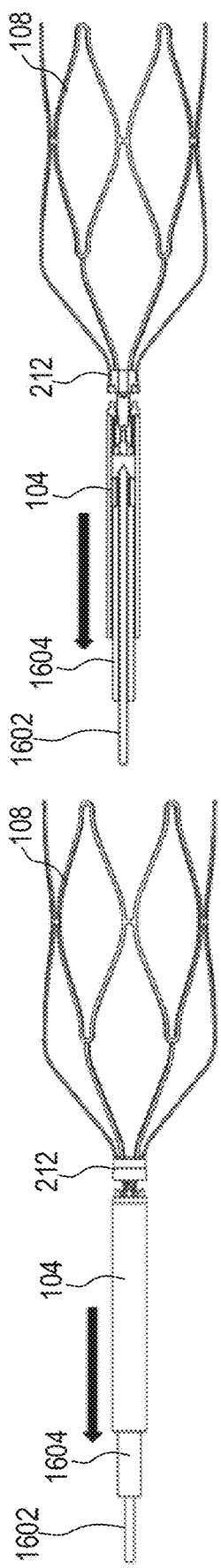
FIG. 17D
FIG. 17E

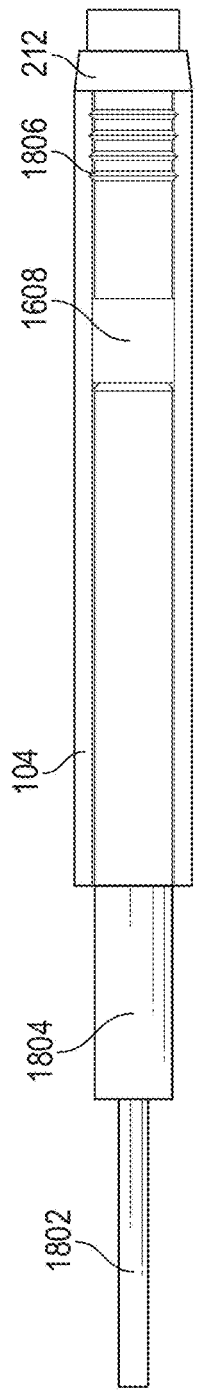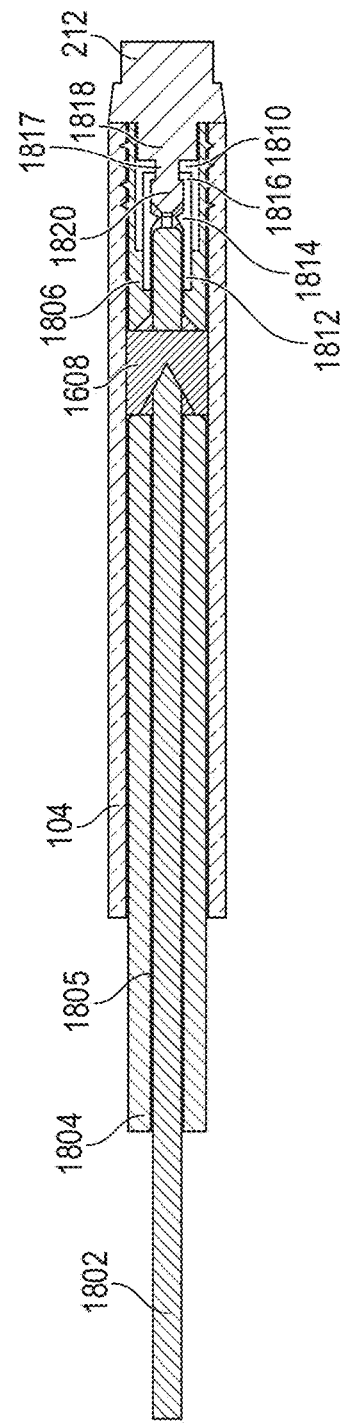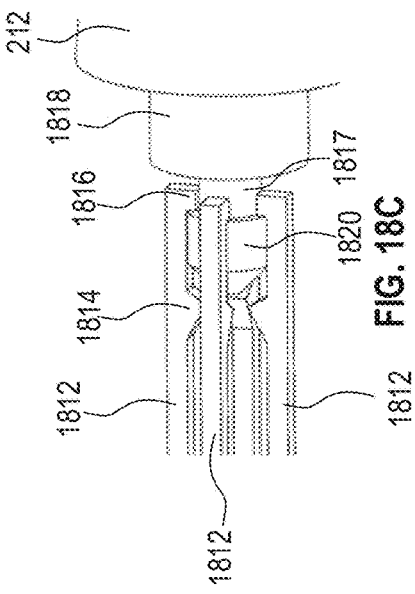
FIG. 18A
FIG. 18B
FIG. 18C

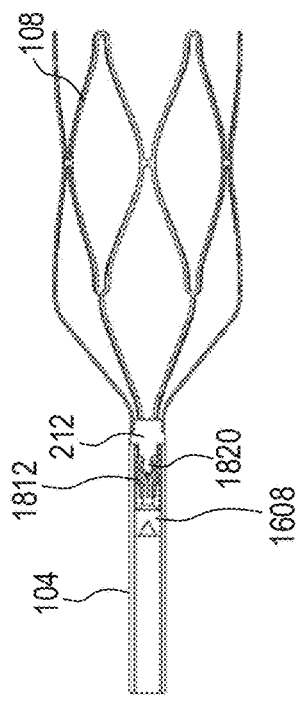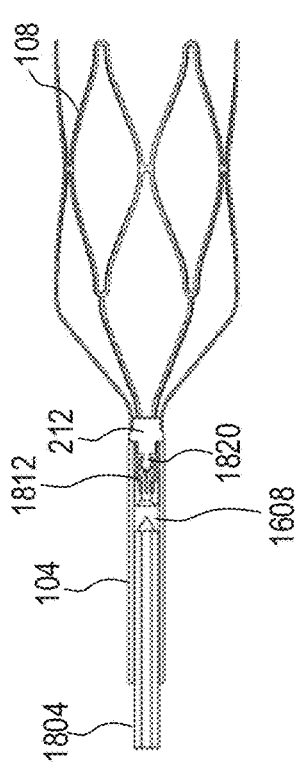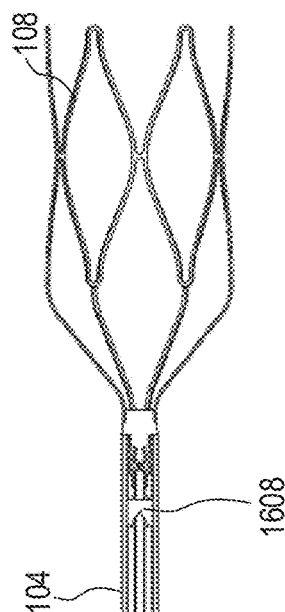
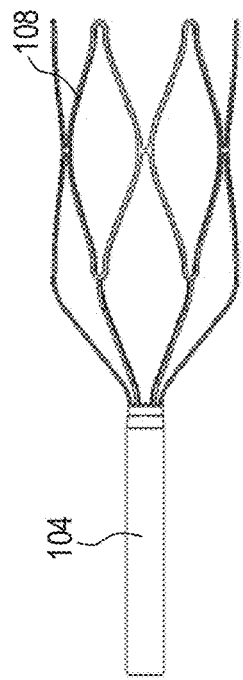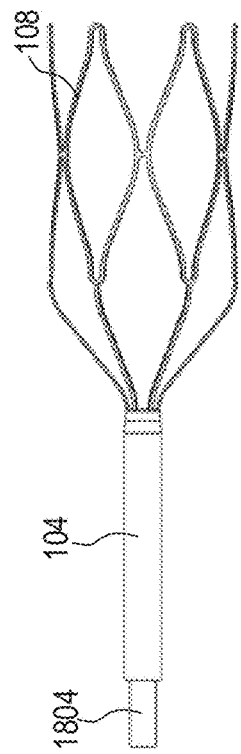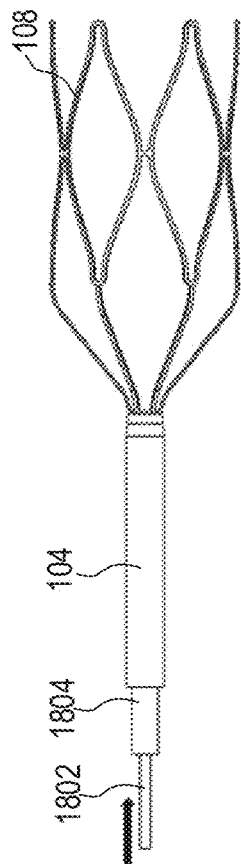
FIG. 19A
FIG. 19B
FIG. 19C

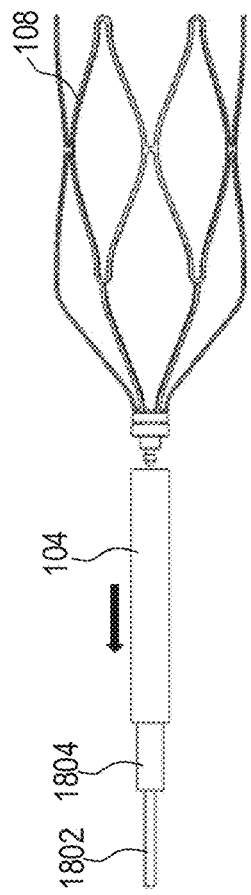
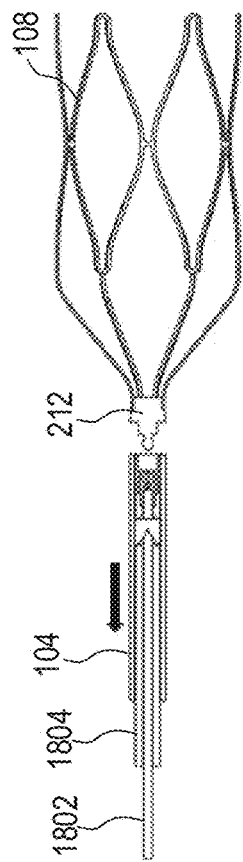
FIG. 19F
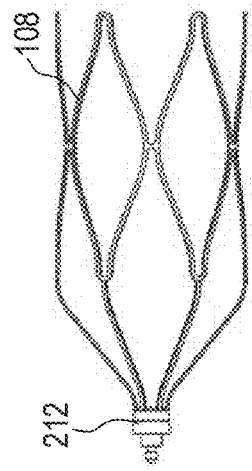
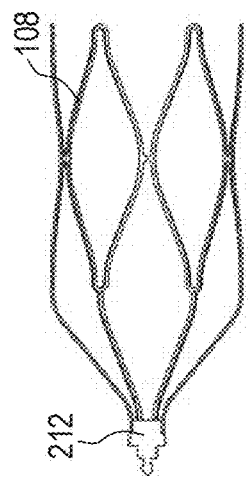
FIG. 19G

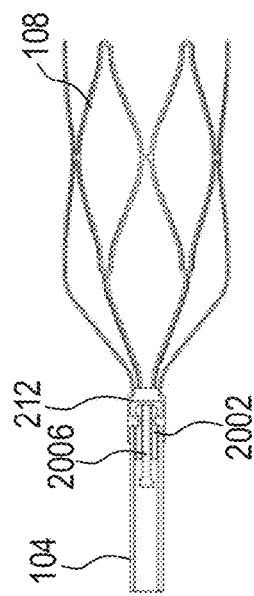
FIG. 21A
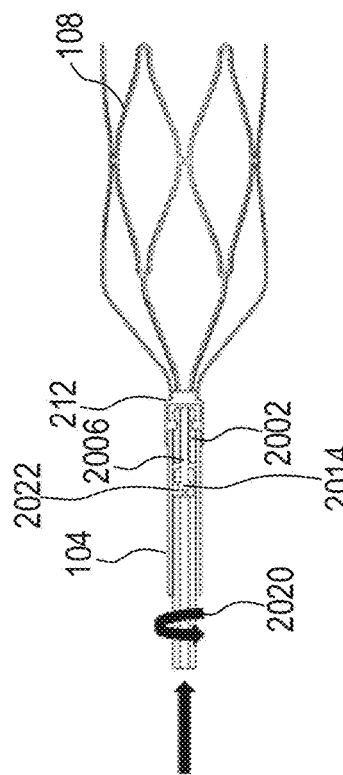
FIG. 21B
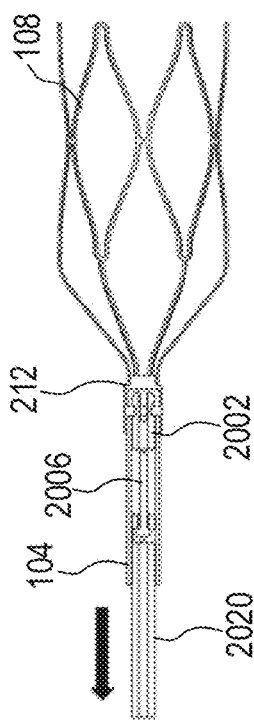
FIG. 21C
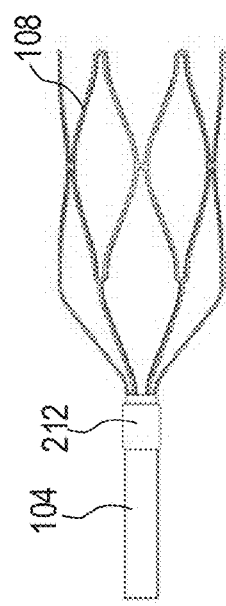
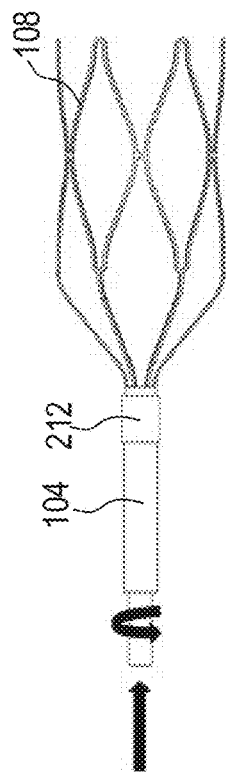

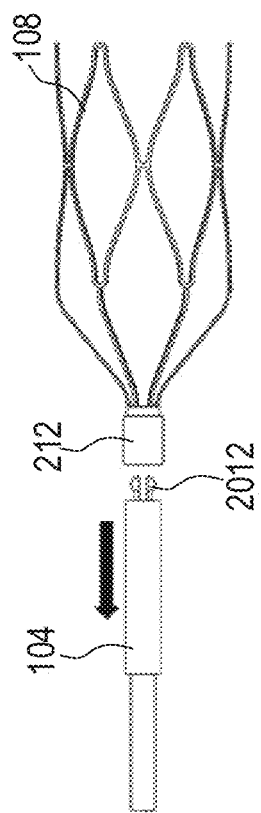
FIG. 21D
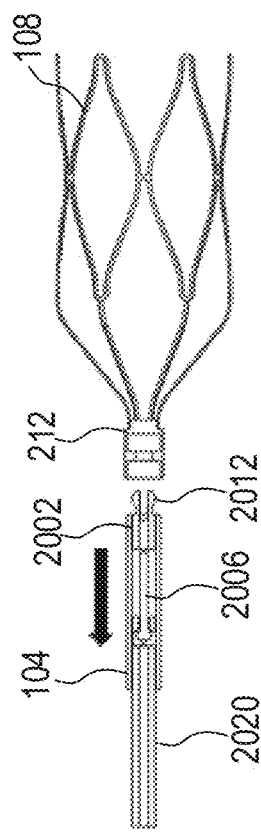
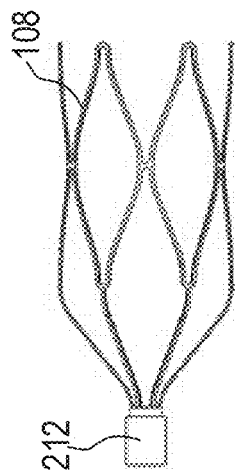
FIG. 21E
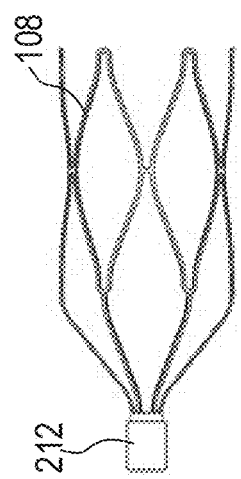

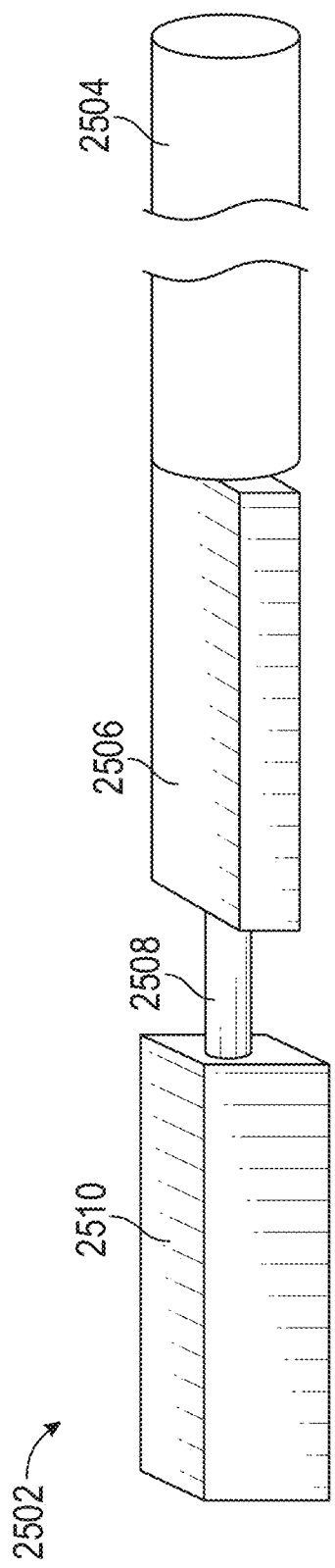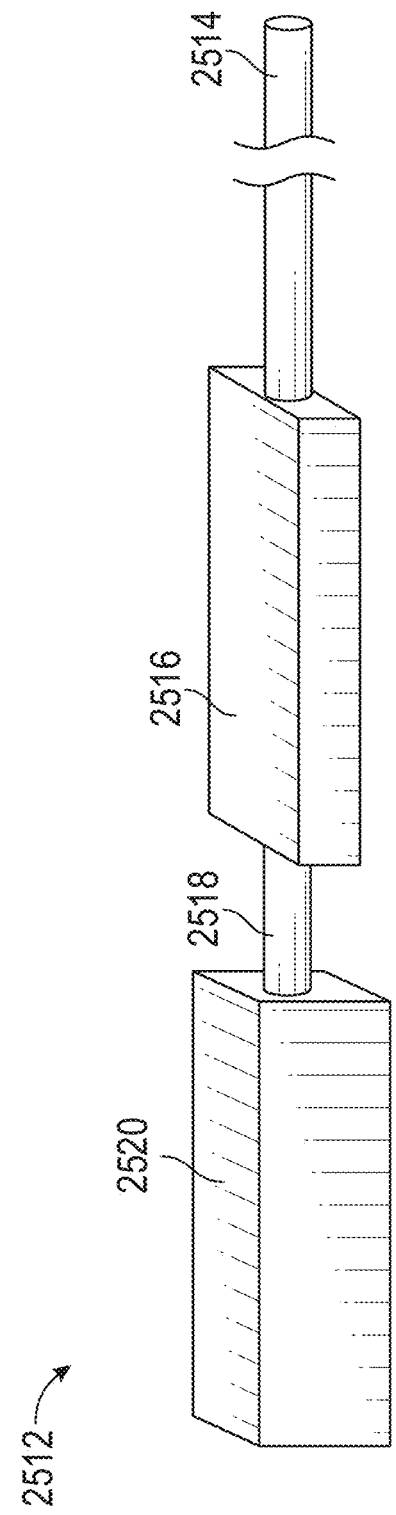
FIG. 25A
FIG. 25B

IMPLANTABLE DEVICES FOR REDUCING PULSATILE PRESSURE WITHIN A BLOOD VESSEL

CROSS-REFERENCE TO RELATED APPLICATIONS

This application claims the benefit of priority of U.S. Provisional Application Ser. No. 63/044,337, filed Jun. 25, 2020, the entire contents of which are incorporated herein by reference.

TECHNICAL FIELD

This application generally relates to implantable devices for reducing pulsatile pressure within a blood vessel, and methods of delivering such devices, such as for use in treating pulmonary hypertension.

BACKGROUND

Pulmonary hypertension (PH) is defined as a rise in mean pressure in the main pulmonary artery. PH may arise from many different causes, but, in all patients, has been shown to increase mortality rate. A deadly form of PH arises in the very small branches of the pulmonary arteries and is known as Pulmonary Arterial Hypertension (PAH). In PAH, the cells inside the small arteries multiply due to injury or disease, decreasing the area inside of the artery and thickening the arterial wall. As a result, these small pulmonary arteries narrow and stiffen, causing blood flow to become restricted and upstream pressures to rise. The stiffening of the pulmonary arteries, or reduction in compliance, increases the workload on the right ventricle, contributing to right heart failure, the typical cause of death in pulmonary hypertension. This increase in stiffness and pressure in the main pulmonary artery is the common connection between all forms of PH regardless of underlying cause.

PH causes the larger pulmonary arteries to dilate and stiffen. As the stiffening progresses, the pulmonary artery is less able to stretch to accommodate each incoming stroke volume. The lack of expansion causes a much larger rise in pressure with each heartbeat (called systolic or peak pressure) than would occur in a healthy, compliant vessel. In between heartbeats, the arteries in a diseased patient do not recoil as they normally would and diastolic pressure and flow through the lungs drops resulting in a reduction in cardiac output. The heart has to work harder to push the same stroke volume of blood into the stiff artery at a higher pressure. At the same time, the high pulse pressure travels down the pulmonary arteries to the small vessels and activates molecular signaling pathways causing the cells to multiply more rapidly, accelerating disease progression.

As the pressure within the pulmonary artery increases, the right side of the heart thickens and enlarges to compensate, but eventually reaches the point where it cannot continue to pump enough blood through the lungs to satisfy the body's need for oxygenated blood. This progressive reduction of blood flow is first noticed as shortness of breath when exercising. Over time, the right ventricular remodeling worsens and patients lose the ability to maintain a normal daily level of activity and enter end-stage heart failure where the right ventricle dilates and loses its ability to contract, reducing blood flow even further. At the end-stage, the patient mortality rate is high.

Current treatment protocols for PH and Primary PAH include administration of pharmaceuticals. However, such pharmaceuticals are extremely expensive and do not directly address the excess stiffening.

Alternatively, by implanting a balloon having a fluid therein, e.g., a gas that may be compressible, in the pulmonary artery, compliance may be restored, and thus the deleterious effects of vessel stiffening may be reduced. Previously known implantable systems and devices having a balloon, conduit, and reservoir have been described, for example by U.S. Pat. Nos. 9,017,359 and 9,333,328 to Scandurra and U.S. Pat. Nos. 8,876,850, 9,039,725, and 9,242,082 to Vollmers, assigned to the assignee of the present disclosure, the entire disclosure of each of which is incorporated by reference herein. During right ventricular systole, the increased blood pressure in the pulmonary artery compresses the fluid in the balloon, and forces the fluid out of the balloon through the conduit and into the reservoir, which may be implanted outside of the vascular system. During right ventricular diastole, the drop in blood pressure within the pulmonary artery results in a pressure gradient between the fluid pressure in the reservoir and the deflated balloon in the pulmonary artery. This gradient causes the fluid to flow back through the conduit into the balloon from the reservoir.

It would be desirable to provide devices and methods for treating heart disease, such as pulmonary hypertension and right heart failure, with improved stability to provide patient convenience and safety, as well as device efficacy.

SUMMARY

The present disclosure provides anchorable devices for reducing pulsatile pressure within a vessel, and methods of delivering such devices, for example, for use in treating pulmonary hypertension or right heart failure, or both pulmonary hypertension and right heart failure. The device may include a reservoir configured to hold a fluid, e.g., a compressible or non-compressible fluid, a transvascular conduit having a distal region and a proximal region coupled to the reservoir, and a compliant member adapted to be implanted in a vessel, e.g., a pulmonary artery, and coupled to the distal region of the transvascular conduit. The compliant member may collapse during systole to move the fluid towards the reservoir and expand during diastole to thereby reduce peak pressure in the vessel.

Under one aspect, a device for reducing pulsatile pressure within a blood vessel includes a fluid reservoir; a compliant member; a conduit coupled to the fluid reservoir and the compliant member and including a distal tip; and an anchor configured to detachably engage the distal tip of the conduit. The anchor may include an expandable structure configured to engage a blood vessel in a deployed state; and a tether wire disposed within the conduit. When the distal tip of the conduit is engaged with the anchor, the compliant member is anchored within a blood vessel, and when the distal tip of the conduit is disengaged from the anchor, the conduit and the compliant member are movable along the tether wire relative to the anchor.

In some configurations, the anchor further includes a docking hub configured to receive and detachably engage the distal tip of the conduit. Optionally, the distal tip of the conduit includes a detent and the docking hub includes a protrusion that detachably engages the detent. Optionally, the docking hub includes a sloped surface configured to engage with a sheath. Optionally, the distal tip of the conduit includes a radiopaque marker configured to permit visualization of location of the distal tip relative to the docking hub.

In some configurations, the expandable structure is constructed from a single piece of NiTi tube. Additionally, or alternatively, the expandable structure optionally includes a plurality of structural members coupled to one another. Optionally, each of the structural members includes a distal apex rolled toward an interior of the anchor to create an atraumatic termination. Additionally, or alternatively, the expandable structure optionally further includes an anchor ring and a plurality of bridging struts, each bridging strut joining a corresponding one of the structural members to the anchor ring.

Optionally, the tether wire has a diameter of 0.2 to 0.5 mm, for example, 0.373 mm. Additionally, or alternatively, the tether wire includes superelastic NiTi.

Some configurations optionally further include a tether wire extension having a first profile. The tether wire may have a second profile configured to detachably engage the first profile so as to create a joint. Some configurations optionally further include a slotted locking tube configured to be advanced over the joint to further secure the tether wire extension to the tether wire. Some configurations optionally further include a wire reservoir coupled to the conduit and configured to house the tether wire.

Under another aspect, a method for delivering a device for reducing pulsatile pressure within a blood vessel includes selecting a device. The device may include a fluid reservoir, a first compliant member, a first conduit coupled to the fluid reservoir and the first compliant member and including a first distal tip, and an anchor including an expandable structure and a tether wire, the tether wire being disposed within the conduit. The method may include engaging the expandable structure with a blood vessel. The method may include engaging the first distal tip with the anchor so as to anchor the first compliant member within the blood vessel.

The method optionally may further include, while the expandable structure is engaged with the blood vessel, disengaging the first distal tip from the anchor; and while the first distal tip is disengaged from the anchor, moving the first conduit and the first compliant member along the tether wire relative to the anchor.

Additionally, or alternatively, the method optionally may include, while the expandable structure is engaged with the blood vessel, removing the first conduit and the first compliant member from the tether wire; inserting the tether wire into a second conduit coupled to a second compliant member and including a second distal tip; and engaging the second distal tip with the anchor so as to anchor the second compliant member within the blood vessel.

In some configurations, the anchor includes a docking hub, and engaging the first distal tip with the anchor includes receiving, by the docking hub, the first distal tip. In some configurations, the docking hub includes a protrusion and the first distal tip includes a detent, and engaging the first distal tip with the anchor includes the protrusion engaging the detent.

In some configurations, the tether wire includes a first profile and the device includes a tether wire extension having a second profile, and the method optionally further includes detachably engaging the first profile of the tether wire with the second profile of the tether wire extension to create a joint. The method optionally further includes advancing a locking tube over the joint to further secure the tether wire extension to the tether wire. The method optionally further includes utilizing a slotted locking tube to align the wires while engaging them.

In accordance with another aspect of the present disclosure, a system for reducing pulsatile pressure within a blood vessel is provided. The system may include a fluid reservoir, a conduit coupled to the fluid reservoir, the conduit having a distal tip, and a balloon disposed on a distal portion of the conduit. The balloon is sized and shaped to be implanted in the blood vessel and is fluidically coupled to the fluid reservoir via the conduit. The system further includes an anchor having an expandable structure sized and shaped to engage the blood vessel in a deployed state, and a docking hub that detachably engages with the distal tip of the conduit. In addition, the system includes a guidewire that may be slidably moveable through a lumen of the conduit. The guidewire has a distal end that may be actuated to disengage the distal tip of the conduit from the docking hub of the anchor such that the balloon and the conduit are removable from the blood vessel while the anchor remains implanted.

The system further may include a seal positioned within the lumen of the conduit proximal to the distal tip. The seal fluidically isolates the fluid reservoir, the compliant member, and the conduit when the conduit is coupled to the fluid reservoir and the compliant member. Moreover, the seal has a passageway for receiving the guidewire therethrough. The passageway of the seal may include a conical proximal portion and a linear distal portion. In addition, the system includes a pusher that may be slidably moveable through the lumen of the conduit. The pusher has a lumen sized and shaped to receive the guidewire therethrough to stabilize the guidewire when the distal end of the guidewire is actuated to disengage the distal tip of the conduit from the docking hub of the anchor.

In some embodiments, the distal end of the guidewire has a first geometry, and the system further includes a screw head positioned within the lumen of the conduit at the distal tip of the conduit. The screw head has a passageway having a second geometry sized and shaped to receive the first geometry of the distal end of the guidewire, and a threaded distal portion that may detachably engage with the docking hub of the anchor. Accordingly, when the distal end of the guidewire is engaged with the screw head, the distal end of the guidewire may be actuated by rotating the guidewire to thereby rotate the threaded distal portion to disengage the distal tip of the conduit from the docking hub of the anchor.

In this embodiment, the system further may include a pusher stop positioned within the lumen of the conduit proximal to the seal. The pusher stop has a passageway sized and shaped to receive a distal portion of the pusher to provide counter-torque when the guidewire is rotated to disengage the distal tip of the conduit from the docking hub of the anchor. Moreover, the system further may include a housing at least partially positioned within the lumen of the conduit at the distal tip of the conduit. The housing has a cavity sized and shaped to rotatably receive at least a portion of the screw head.

In another embodiment, the system further includes one or more tangs positioned within the lumen of the conduit at the distal tip of the conduit, which are transitionable between a contracted state and an expanded state. Each of the one or more tangs may include a ramp that may be actuated via distal movement of the distal end of the guidewire against the ramp to transition from the contracted state to the expanded state, as well as a distal gripping portion sized and shaped to engage the docking hub in the contracted state and to release the docking hub in the expanded state to disengage the distal tip of the conduit from the docking hub of the anchor.

For example, the one or more tangs may include a plurality of tangs arranged circumferentially around a path of the distal end of the guidewire. In addition, the distal end of the guidewire may be actuated by moving the guidewire distally to thereby engage the ramp and transition the one or more tangs from the contracted state to the expanded state to disengage the distal tip of the conduit from the docking hub of the anchor. In this embodiment, the docking hub may include a neck portion and a bulb, such that the distal gripping portion of the one or more tangs is sized and shaped to engage the neck portion of the docking hub in the contracted state to prevent distal movement of the bulb. Moreover, a housing may be positioned within the lumen of the conduit at the distal tip of the conduit, wherein at least a portion of the one or more tangs are positioned within a cavity of the housing. The cavity is sized and shaped to permit the one or more tangs to transition from the contracted state to the expanded state therein.

In yet some other embodiments, the system may include a plug having a proximal portion sized and shaped to be fixed within the lumen of the conduit at the distal tip of the conduit, a collapsible bulb, and a neck portion extending therebetween, wherein the plug has a lumen extending therethrough. In addition, the system may include a wire that may be removeably positioned within the lumen of the plug such that, when the wire is positioned within the lumen of the plug, the collapsible plug is prevented from collapsing. Moreover, the docking hub may include a ridge sized and shaped to engage with the neck portion of the plug such that the bulb prevents distal movement of the docking hub.

A proximal end of the wire may include a knob, and the distal end of the guidewire may have a groove sized and shaped to engage with the knob. For example, the groove may have an L shape such that the distal end of the guidewire may engage the knob by being moved distally to receive the knob and rotated to lock the knob within the groove such that proximal movement of the guidewire causes proximal movement of the wire. Accordingly, the distal end of the guidewire may be actuated to engage the knob such that proximal movement of the guidewire removes the wire from the lumen of the plug, and proximal movement of the conduit and the plug when the wire is removed causes the bulb to collapse against the ridge of the docking hub to disengage the distal tip of the conduit from the docking hub of the anchor.

In some embodiments, the conduit includes an anchor tab extending distally from the distal tip of the conduit, and the docking hub includes one or more tangs that are transitionable between a contracted state and an expanded state, such that the one or more tangs are sized and shaped to engage the anchor tab in the contracted state. In this embodiment, the system further includes a collar slidably moveable over the one or more tangs, such that the guidewire may push the collar distally over the one or more tangs. The one or more tangs are biased toward the expanded state such that when the guidewire pushes the collar distally such that the one or more tangs are exposed from the collar, the one or more tangs transition from the contracted state to the expanded state to release the anchor tab and disengage the distal tip of the conduit from the docking hub of the anchor.

In some embodiments, the distal tip of the conduit includes a plurality of tangs pivotally coupled via a scissor hinge, the plurality of tangs sized and shaped to engage the docking hub in an expanded state. In addition, the system includes a seal slidably moveable through the lumen of the conduit, and the guidewire may push the seal distally to engage the plurality of tangs to transition the plurality of tangs from the expanded state to a contracted state via the scissor hinge to release the docking hub and disengage the distal tip of the conduit from the docking hub of the anchor.

In some embodiments, the docking hub includes an anchor tab extending proximally from the docking hub, and the system further includes one or more tangs positioned within the lumen of the conduit at the distal tip and transitionable between a contracted state and an expanded state, the one or more tangs sized and shaped to engage the anchor tab in the contracted state. In addition, the system includes a collar slidably moveable over the one or more tangs. The collar has an eyelet, such that the distal end of the guidewire may engage with the eyelet of the collar. The one or more tangs are biased toward the expanded state such that proximal movement of the guidewire when the distal end of the guidewire is engaged with the eyelet of the collar moves the collar proximally such that the one or more tangs are exposed from the collar and transition from the contracted state to the expanded state to release the anchor tab and disengage the distal tip of the conduit from the docking hub of the anchor.

In some embodiments, the system includes a bulb coupled to the distal tip of the conduit via a plurality of thin connectors, the bulb sized and shaped to engage with the docking hub via a snap fit connection. The bulb includes an eyelet, such that the distal end of the guidewire may engage with the eyelet of the bulb, such that proximal movement of the guidewire when the distal end of the guidewire is engaged with the eyelet of the bulb breaks the plurality of thin connectors and releases the bulb from the docking hub to disengage the distal tip of the conduit from the docking hub of the anchor.

In some embodiments, the fluid reservoir includes a main body having an interior chamber and a groove extending circumferentially along an outer surface of the main body, the groove sized and shaped to receive at least a portion of the conduit. In addition, the fluid reservoir may include a header removably coupled to the main body via a clip attachment. The header is sized and shaped to receive a proximal end of the conduit to fluidicly couple the conduit and the interior chamber of the fluid reservoir.

In accordance with another aspect of the present invention, an alternative system for reducing pulsatile pressure within a blood vessel is provided. The system includes a fluid reservoir, a first conduit that may be coupled to the fluid reservoir, a balloon disposed on a distal portion of the first conduit, the balloon sized and shaped to be implanted in the blood vessel and fluidicly coupled to the fluid reservoir via the first conduit, and a second conduit extending distally from the first conduit, the second conduit having a lumen and a distal tip. The system further includes an anchor having an expandable structure transitionable between a contracted state within the lumen of the second conduit and an expanded state to engage the blood vessel, and a docking hub coupled to the expandable structure, which may be slidably moveable within the second conduit. The docking hub has an asymmetric passageway.

In addition, the system includes a guidewire that may be slidably moveable through a lumen of the first and second conduits, the guidewire having a proximal portion having a first geometry, a distal portion having a second geometry offset from the first geometry, and a neck portion therebetween. For example, the first geometry of the proximal portion may have a first flat surface, and the second geometry of the distal portion may have a second flat surface offset from the first flat surface by 90 degrees. When the guidewire is in a first orientation, the distal portion of the guidewire is slidably moveable through the asymmetric passageway of the docking hub, and when the guidewire is rotated to a second orientation offset from the first orientation while the neck portion of the guidewire is positioned within the asymmetric passageway, the proximal portion of the guidewire is slidably moveable through the asymmetric passageway while the distal portion of the guidewire is not slidably moveable through the asymmetric passageway. The distal tip of the second conduit is sized and shaped to prevent distal movement of the docking hub beyond the distal tip of the second conduit.

In some embodiments, when the guidewire is in the second orientation and the distal portion of the guidewire is distal to the docking hub, proximal movement of the guidewire causes the distal portion of the guidewire to engage the docking hub and retract the docking hub within the lumen of the second conduit to thereby transition the expandable structure from the expanded state to the contracted state within the lumen of the second conduit. In some embodiments, when the guidewire is in the first orientation and the expandable structure is in the contracted state within the lumen of the second conduit, distal movement of the guidewire causes the proximal portion of the guidewire to engage the docking hub and push the docking hub distally within the lumen of the second conduit to thereby transition the expandable structure from the contracted state to the expanded state within the blood vessel.

In some embodiments, the distal tip of the second conduit converges radially inward such that a distal end of the distal tip has a diameter less than a diameter of the docking hub to thereby prevent distal movement of the docking hub beyond the distal tip of the second conduit. In some embodiments, the distal tip of the second conduit includes a lip that extends radially inward, and the docking hub includes a retention ring that engages with the lip to thereby prevent distal movement of the docking hub beyond the distal tip of the second conduit. In some embodiments, the distal tip of the second conduit includes one or more crossbars extending across an opening of the distal tip to thereby prevent distal movement of the docking hub beyond the distal tip of the second conduit. In some embodiments, the distal tip of the second conduit includes one or more tabs that extend radially inward to thereby prevent distal movement of the docking hub beyond the distal tip of the second conduit.

In some embodiments, the system includes a seal positioned between the first conduit and the second conduit. The seal is sized and shaped to fluidicly isolate the fluid reservoir, the compliant member, and the first conduit when the first conduit is coupled to the fluid reservoir and the compliant member. The seal has a passageway for receiving the guidewire therethrough.

In accordance with another aspect of the present invention, a method for reducing pulsatile pressure within a blood vessel of a patient is provided. The method includes: delivering a distal portion of a conduit within a blood vessel, the distal portion having a balloon disposed thereon; deploying an anchor coupled to a distal tip of the conduit via a docking hub; coupling a proximal portion of the conduit to a fluid reservoir; implanting the reservoir within the patient; decoupling the proximal portion of the conduit from the fluid reservoir; inserting a guidewire through a lumen of the conduit; and actuating a distal end of the guidewire to disengage the distal tip of the conduit from the docking hub of the anchor such that the balloon and the conduit are removable from the blood vessel while the anchor remains implanted.

BRIEF DESCRIPTION OF THE DRAWINGS

FIGS. 2A-2I schematically illustrate exemplary configurations of components of the implantable device of FIGS. 1A-1C, in accordance with the principles of the present disclosure.

FIG. 3B schematically illustrates the device of FIGS. 1A-1C and 2A-2I in a delivery state in which the anchor is contracted within a sheath within a blood vessel.

FIG. 3C schematically illustrates the device of FIGS. 1A-1C and 2A-2I in a deployed state in which the anchor expands to engage the blood vessel.

FIGS. 5A-7B schematically illustrate alternative structures for coupling a docking hub to a conduit in accordance with the principles of the present disclosure.

FIGS. 8A-8F schematically illustrate alternative exemplary structures for coupling a tether wire to a tether wire extension in accordance with the principles of the present disclosure.

FIGS. 9A-11C schematically illustrate alternative exemplary struts of the anchor in accordance with the principles of the present disclosure.

FIGS. 16A-16E schematically illustrate additional alternative structures for decoupling a docking hub from a conduit via a screw attachment in accordance with the principles of the present disclosure.

FIGS. 17A-17E schematically illustrate an exemplary method of decoupling and removing the conduit from the docking hub using the structures of FIGS. 16A-16E, in accordance with the principles of the present disclosure.

FIGS. 18A-18C schematically illustrate additional alternative structures for decoupling a docking hub from a conduit via a push mechanism in accordance with the principles of the present disclosure.

FIGS. 19A-19G schematically illustrate an exemplary method of decoupling and removing the conduit from the docking hub using the structures of FIGS. 18A-18C, in accordance with the principles of the present disclosure.

FIGS. 25A and 25B schematically illustrate alternative guidewires for withdrawing and deploying an anchor through a conduit in accordance with the principles of the present disclosure.

DETAILED DESCRIPTION

Provided herein are implantable devices including anchors and detachable compliant members for reducing pulsatile pressure within a blood vessel, and methods of delivering such devices. In accordance with the principles of the present disclosure, the present implantable devices may be used to treat all forms of pulmonary hypertension (PH) as described in the World Health Organization Clinical Classification, including Pulmonary Arterial Hypertension (PAH), and right heart failure (RHF). However, it should be understood that the present devices and methods may be adapted for use with and delivered into any suitable blood vessel.

Figure 1A:
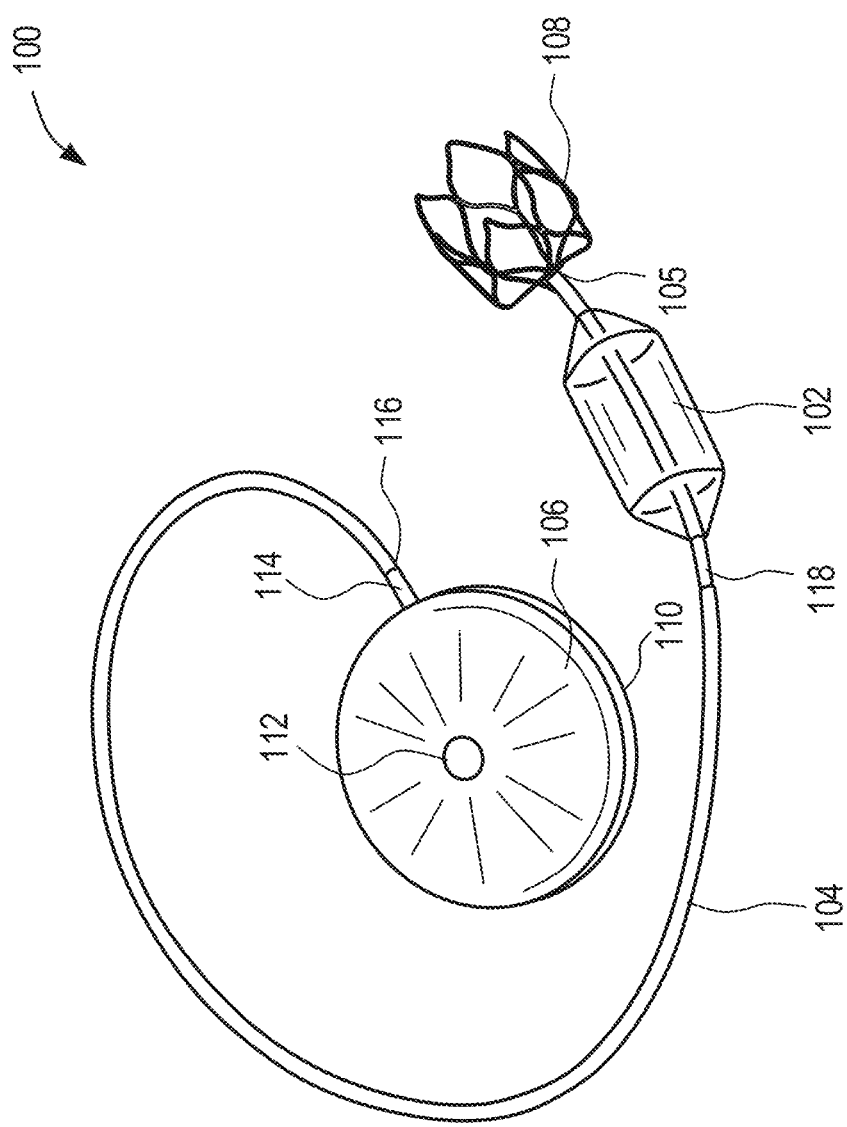
FIGS. 1A-1C schematically illustrate components of exemplary configurations of an implantable device including an anchor and a detachable compliant member for reducing pulsatile pressure within a blood vessel, in accordance with the principles of the present disclosure.
Figure 1B:
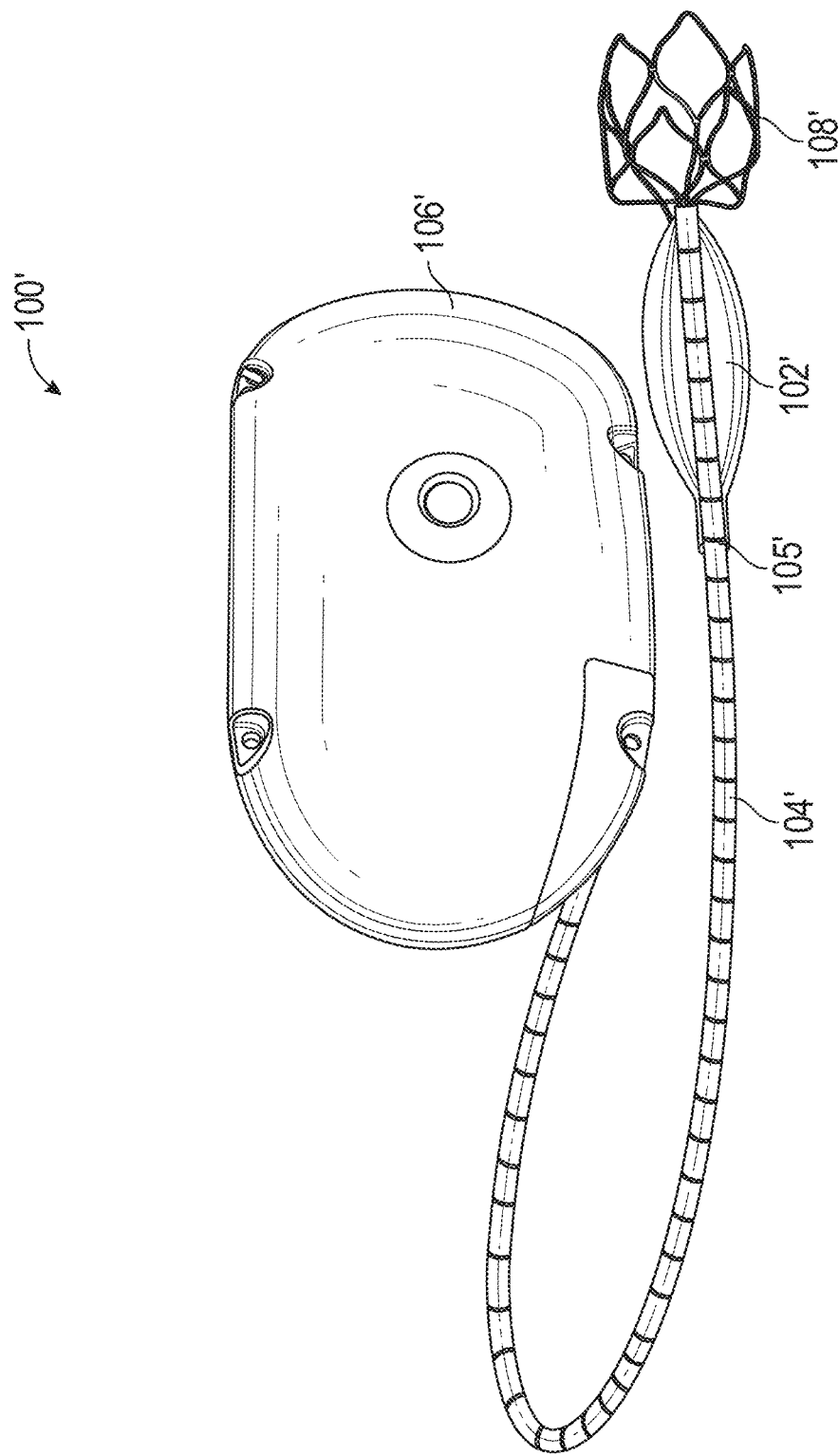
Figure 1C:
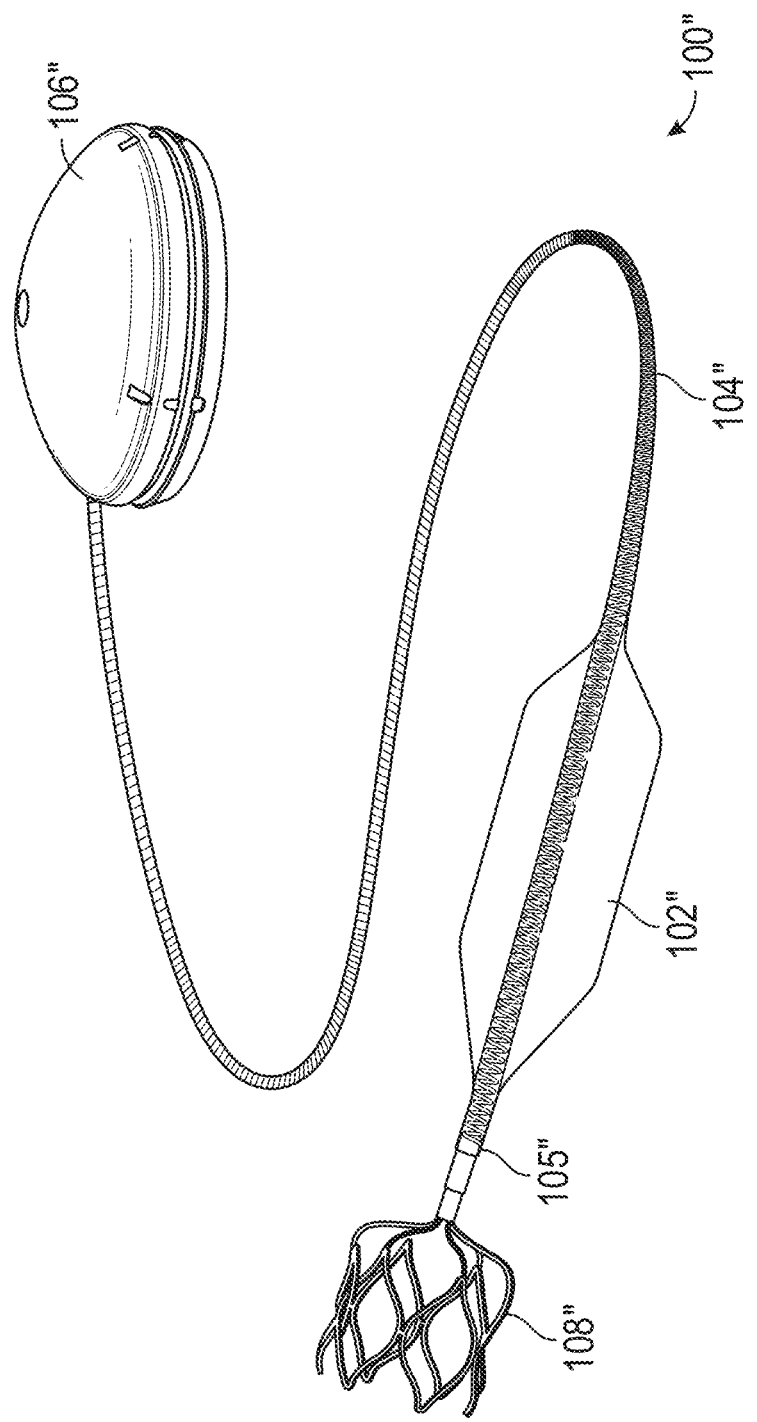

FIGS. 1A-1C schematically illustrate components of exemplary configurations of an implantable device for reducing pulsatile pressure within a blood vessel, in accordance with the principles of the present disclosure. Device 100 illustrated in FIG. 1A may include detachable compliant member 102, conduit 104, fluid reservoir 106, and anchor 108. Conduit 104 is coupled to reservoir 106 and compliant member 102 and includes distal tip 105. Anchor 108 is configured to detachably secure compliant member 102 at any suitable portion of any suitable blood vessel, such as the pulmonary artery, for example any suitable portion of the main pulmonary artery and/or one or more of the pulmonary artery branches. For example, anchor 108 may be implanted within a pulmonary artery branch to anchor compliant member 102 in the main pulmonary artery. As used herein, pulmonary artery includes the main pulmonary artery and the pulmonary artery branches. Compliant member 102 may be configured for long-term implantation within the body lumen, e.g., from a period of several weeks, months or years. In a preferred embodiment, compliant member 102 is a balloon. Compliant member 102 may be attachable to and detachable from anchor 108, for example, so as to be movable or removable relative to anchor 108 while anchor 108 is engaged with a blood vessel in a deployed state. Optionally, compliant member 102 may be replaced with another such compliant member 102 as appropriate, as described in greater detail below.

In configurations in which compliant member 102 is implanted within a pulmonary artery, with each heartbeat, fluid within device 100 moves away from compliant member 102 to reservoir 106 via conduit 104 and then towards compliant member 102 from reservoir 106 via conduit 104. By collapsing/contracting and getting smaller in volume responsive to an increase in pulsatile pressure of the pulmonary artery, compliant member 102 mimics the expansion of the pulmonary artery (increasing intravascular volume) that naturally occurs in a healthy person, making room for incoming blood. This collapsing action has the effect of absorbing or reducing the peak systolic pressure and also reducing the rate of change (e.g., acceleration) of blood flow distal to the compliant member. When the heart begins to relax, the pulmonary valve closes and the pressure in the main pulmonary artery begins to drop. Responsive to the drop in pressure in the pulmonary artery, the compliant member 102 drops below the pressure level in reservoir 106, fluid flows from reservoir 106 to compliant member 102 via conduit 104 such that the potential energy within compliant member 102 increases. During diastole, compliant member 102 may expand, for example, to approximately the full volume of compliant member 102 to increase pressure in the pulmonary artery to push additional blood through the artery towards the lungs, thereby increasing cardiac output. Continuous expansion and collapse of compliant member 102 is expected to reduce peak systolic pressure and increase diastolic pressure, thus reducing the load on the right ventricle and increasing heart efficiency. Compliant member 102 may be designed to handle multiple expansion and collapse cycles over the course of long-term implantation, e.g., over a period of weeks, months or years. As provided herein, compliant member 102 suitably may be detached from anchor 108 so as to allow removal of compliant member 102 from the pulmonary artery (or other body lumen) and optionally so as to allow another such compliant member 102 to be anchored within the pulmonary artery or other suitable body lumen.

As will be appreciated by those of ordinary skill in the art, any suitable biocompatible fluid, e.g., liquid or gas, may be used in the device 100, e.g., may be within compliant member 102, conduit 104, and reservoir 106, and transferred between compliant member 102 and reservoir 106 via conduit 104. The fluid may be or include a compressible gas such that the volume of the gas changes in response to a change in pressure in the artery (or other implantation location of compliant member 102) consistent with the gas bulk modulus of the gas. Furthermore, the gas is preferably nontoxic, easily absorbed by the body, and has concentrations or physical properties that resist diffusion through the wall of the compliant member. Suitable gases may include, but are not limited to, nitrogen, carbon dioxide, argon, neon, nitrous oxide (NO), gaseous water, oxygen, methane, sulfur hexafluoride, a gaseous perfluorinated compound, and helium, and any suitable combinations thereof. Optionally, the gas may have therapeutic properties, such as nitric oxide which causes vasodilation. Examples of suitable gases, and compliant members that may be compatible with such gases, are described in U.S. Patent App. Pub. No. 2021/0069396 to Vollmers, entitled "Diffusion and infusion resistant implantable devices for reducing pulsatile pressure," the entire contents of which are incorporated by reference herein. Alternatively, the fluid may be or include a suitable liquid such as water or saline.

Referring back to FIG. 1A, compliant member 102 may be detachably secured within the blood vessel via anchor 108. In various optional configurations, anchor 108 may be detachably coupled to any suitable portion of compliant member 102 or to any suitable portion of conduit 104, for example so as to secure compliant member 102 within the blood vessel as appropriate, while allowing compliant member 102 to be detached from anchor 108 as appropriate while leaving anchor 108 in place within the blood vessel. For example, anchor 108 may be detachably coupled to conduit 104 at a location proximal to compliant member 102. In another example, such as illustrated in FIG. 1A, anchor 108 may be detachably coupled to conduit 104 at a location distal to compliant member 102, for example, to distal tip 105 of conduit 104. Optionally, anchor 108 and distal tip 105 respectively may include any suitable combination of structural features, such as one or more protrusions and detents respectively, that engage with one another while permitting later disengagement from one another, for example, that snap-fit with one another, such as described in greater detail elsewhere herein. Anchor 108 may be configured to expand from a contracted state, e.g., when compressed in a delivery sheath, to a deployed state responsive to an event, e.g., removal from the sheath or expansion of compliant member 102. In the expanded state, anchor 108 is sized and configured to contact and engage with the inner wall of the blood vessel, thus anchoring the compliant member 102 within the blood vessel when the distal tip of the conduit 104 is engaged with anchor 108.

Conduit 104 is configured to fluidicly couple compliant member 102 to reservoir 106. Conduit 104 includes proximal region 116 and distal region 118. In the illustrated configuration, conduit 104 is coupled to port 114 of reservoir 106 at proximal region 116 and is coupled to compliant member 102 at distal region 118. In some configurations, conduit 104 has a length suitable to extend from reservoir 106 (which may be implanted in a subcutaneous space in a region near the right or left subclavian or jugular or axillary vein, axilla, or superficial to the abdomen), through the subclavian or axillary or jugular vein, and past the pulmonary valve to compliant member 102 which is located within the pulmonary artery. In some configurations, conduit 104 extends through and past compliant member 102 by a predetermined distance, such that distal tip 105 of conduit 104 is located at or distal to the distal end of compliant member 102, e.g., such as illustrated in FIG. 1A. Conduit 104 may include one or more ports 120 (not specifically illustrated in FIG. 1A, but may be configured such as illustrated in FIGS. 3B-3C) that are located within compliant member 102 so as to permit fluid to be introduced from conduit 104 into the interior space of compliant member 102. In some configurations, conduit 104 has a length between about 60-150 cm, for example about 90-130 cm, or about 120 cm. In some configurations, the diameter of conduit 104 may be about 3-5 mm, e.g., about 4 mm, at distal region 118, and optionally may be variable along the length of conduit 104, for example, up to a predetermined maximum diameter, e.g., about 10-20 mm, for example 15 mm. Preferably, conduit 104 has a wall/membrane thickness between about 0.001 to 0.020 inches. As used herein, the terms "about" and "approximately" are intended to mean within ±10% of the stated value.

As described above, at least a portion of conduit 104 may extend through compliant member 102. Optionally, the surface of the conduit 104 within compliant member 102 may be coated with compliant material or porous compliant material which may act to cushion the surface of the conduit. Suitable materials may include polymers, open cell foamed rubber, foamed rubber, silicones, woven or knitted fibers, dense brush-type materials such as Velcro, and the like. Such coatings may, for example, prevent acoustic pressure spikes in the surrounding blood if the compliant member collapses completely responsive to an increase in pressure within the blood vessel. Such coatings may also reduce impact forces between the compliant member and the conduit.

Referring back to FIG. 1A, fluid reservoir 106 is configured to receive and hold a fluid, e.g., liquid or gas, therein. In some configurations, reservoir 106 includes housing 110, septum 112, and port 114. Reservoir 106 may be formed from any suitable material and may include materials that reduce diffusion of fluid from the internal cavity (not specifically illustrated) of reservoir 106 out of the device and of external fluid into the device, e.g., a carbon-polymer composite. Preferably, housing 110 is sealed such that when the conduit 104 is attached, no gas or fluid can enter or exit the reservoir except through the conduit 104 or through septum 112, and may include titanium, stainless steel, or other biocompatible material. Reservoir 106 optionally is configured to be implanted subcutaneously in a suitable body cavity, e.g., within a subcutaneous or sub facial space in a region near the right or left subclavian vein, axillary or abdominal positions. Reservoir 106 may be free floating within a pocket in the tissue or may be fastened in place with sutures. Although any suitable shape may be used, in one exemplary configuration, reservoir 106 has a flattened disk shape with rounded edges to reduce irritation to surrounding body tissues. The interior cavity of reservoir 106 is in fluidic communication with the interior cavity of compliant member 102, e.g., via one or more lumens (not specifically illustrated) of conduit 104, such that fluid may move between the interior cavity of reservoir 106 and the interior cavity of compliant member 102 and/or pressure may equalize between such cavities. In some configurations, the interior cavity of reservoir 106 has a volume of about 50-450 ml, for example about 100-250 ml. Optionally, the external surface of reservoir 106 may be lubricious, such that it impedes adhesion of body components such as platelets or proteins. Exemplary but not limiting lubricants may include silicone or hyaluronan based materials. The external surface of the reservoir may also be textured or coated to increase adhesion of tissue.

Septum 112 is constructed to allow the addition of fluid to or the removal of fluid from reservoir 106 using a suitable needle. For example, in configurations in which reservoir 106 is implanted subcutaneously, septum 112 may permit transcutaneous needle access to the interior cavity of reservoir 106. Septum 112 may be configured to permit repeated needle penetrations while maintaining a fluid-tight or gas-tight seal, and may be formed from any suitable material including any suitable material or combination of materials that reduces diffusion of fluid through reservoir 106, e.g., a carbon-polymer composite. Radiopaque, magnetic, acoustic, or other markers may also or alternatively be incorporated into or attached to septum 112 so as to facilitate locating, viewing or tracking of septum 112 with a suitable imaging or sensing system.

Port 114 of reservoir 106 is configured to permit fluidic communication between conduit 104 and the interior cavity of reservoir 106. Port 114 may include a suitable structure to permit coupling between conduit 104 and reservoir 106 such as a nipple, threads, ribs, collet or the like.

Device 100' illustrated in FIG. 1B may be configured similarly as device 100 described with reference to FIG. 1A. For example, device 100' may include detachable compliant member 102' which may be configured similarly as detachable compliant member 102, conduit 104' which may be configured similarly as conduit 104, fluid reservoir 106' which may be configured similarly as fluid reservoir 106, and anchor 108' which may be configured similarly as anchor 108. Conduit 104' is coupled to reservoir 106' and compliant member 102' and includes a distal tip 105'. Anchor 108' is configured to detachably secure compliant member 102' at any suitable portion of any suitable blood vessel, such as the pulmonary artery, for example any suitable portion of the main pulmonary artery and/or one or more of the pulmonary artery branches, in a manner such as described with reference to FIG. 1A. For example, anchor 108' may be implanted within a pulmonary artery branch to anchor compliant member 102' in the main pulmonary artery. As used herein, pulmonary artery includes the main pulmonary artery and the pulmonary artery branches. Compliant member 102' may be configured for long-term implantation within the body lumen, e.g., from a period of several weeks, months or years. Compliant member 102' is configured so as to be attachable to and detachable from anchor 108', for example, so as to be movable or removable relative to anchor 108' while anchor 108' is engaged with a blood vessel in a deployed state. Optionally, compliant member 102' may be replaced with another such compliant member 102' as appropriate, as described in greater detail below. In configurations in which compliant member 102' is implanted within a pulmonary artery, with each heartbeat, fluid within device 100' moves away from compliant member 102' to reservoir 106' via conduit 104' and then towards compliant member 102' from reservoir 106' via conduit 104' so as to reduce pulsatile pressure in a manner such as described with reference to FIG. 1A.

Figure 1D:
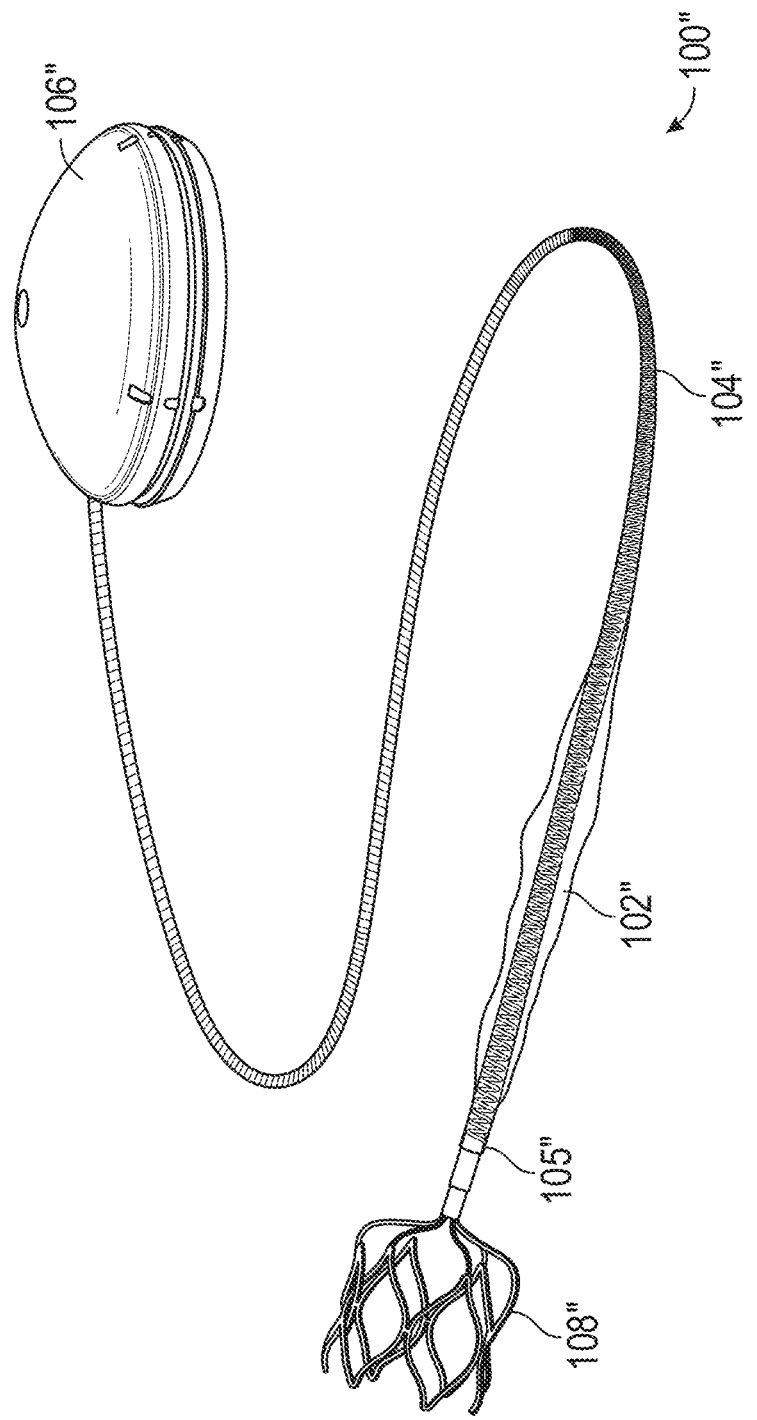
FIG. 1D illustrates the configuration of FIG. 1C with the compliant member in a collapsed configuration.

Device 100" illustrated in FIG. 1C may be configured similarly as device 100 described with reference to FIG. 1A. For example, device 100" may include detachable compliant member 102" which may be configured similarly as detachable compliant member 102, conduit 104" which may be configured similarly as conduit 104, fluid reservoir 106" which may be configured similarly as fluid reservoir 106, and anchor 108" which may be configured similarly as anchor 108. Conduit 104" is coupled to reservoir 106" and compliant member 102" and includes a distal tip 105". Anchor 108" is configured to detachably secure compliant member 102" at any suitable portion of any suitable blood vessel, such as the pulmonary artery, for example any suitable portion of the main pulmonary artery and/or one or more of the pulmonary artery branches, in a manner such as described with reference to FIG. 1A. For example, anchor 108" may be implanted within a pulmonary artery branch to anchor compliant member 102" in the main pulmonary artery. As used herein, pulmonary artery includes the main pulmonary artery and the pulmonary artery branches. Compliant member 102" may be configured for long-term implantation within the body lumen, e.g., from a period of several weeks, months or years. Compliant member 102" is configured so as to be attachable to and detachable from anchor 108", for example, so as to be movable or removable relative to anchor 108" while anchor 108" is engaged with a blood vessel in a deployed state. Optionally, compliant member 102" may be replaced with another such compliant member 102" as appropriate, as described in greater detail below. In configurations in which compliant member 102" is implanted within a pulmonary artery, with each heartbeat, fluid within device 100" moves away from compliant member 102" to reservoir 106" via conduit 104" and then towards compliant member 102" from reservoir 106" via conduit 104" so as to reduce pulsatile pressure in a manner such as described with reference to FIG. 1A. FIG. 1D illustrates the configuration of FIG. 1C with the compliant member 102 in a collapsed configuration.

Figure 1E:
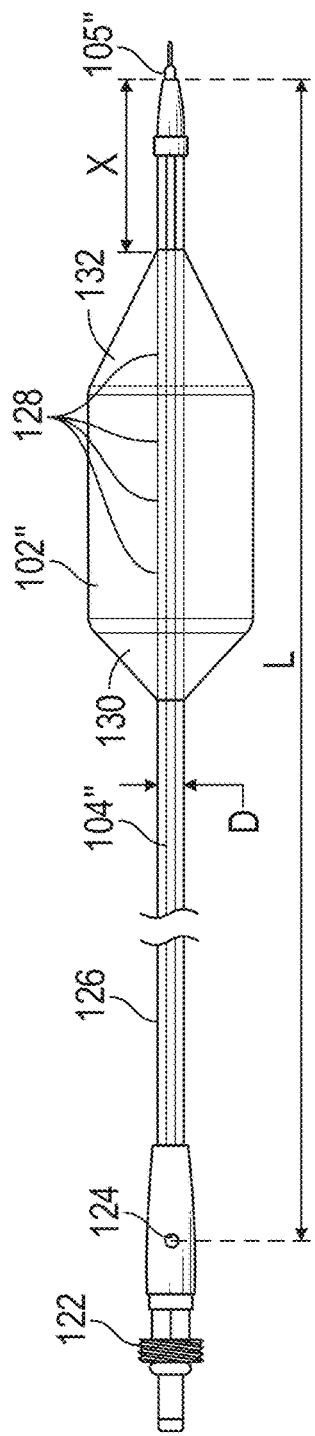
FIG. 1E illustrates an exemplary conduit and compliant member that may be used in the device of FIGS. 1C and 1D.

FIG. 1E illustrates conduit 104" and compliant member 102" of device 100" in accordance with some examples. Conduit 104" illustratively includes at its proximal region reservoir connector 122 configured to be releasably coupled to reservoir 106". Reservoir connector 122 creates a fluid tight seal with the reservoir such that fluid can flow between conduit 104" and the reservoir without leaking. Reservoir connector 122 may include a threaded portion to be releasably connected to a corresponding threaded portion in the reservoir. One or more O-rings also may be used to create the fluid tight seal. The proximal region of conduit 104" may also include tether wire exit port 124 where the tether wire of the anchor exits the wire lumen in conduit 104" such that the proximal region of the tether wire may be positioned at a suitable point within the reservoir. Tether wire exit port 124 is illustratively located distal to the fluid exit port of conduit 104" so that the tether wire may be deflected in a desirable manner into the reservoir.

Conduit 104" also may include coil 126 to enhance conduit strength and facilitate deflection of the conduit in vivo. Coil 126 may be embedded with the wall of conduit 104" and may be spiral shaped. Coil 126 may be formed of polymer and/or metal such as a shape memory metal or superelastic metal. For example, coil 126 may be nickel titanium (NiTi or Nitinol), superelastic NiTi, braided wire, a multifilar wire, a monofilament wire, stainless steel NiTi alloy, tertiary NiTi alloy, titanium, and/or MP35N alloy. As illustrated, the pitch of coil 126 may vary along the length of conduit 104". For example, the distance between peaks of coil 126 may be less proximal to balloon 102" than within balloon 102". The increased distance between peaks of coil 126 within balloon 102" may provide space for fluid ports 128 within balloon 102" for moving fluid from within balloon 102" to within conduit 104" and back. As illustrated, the distance between peaks of coil 126 may be less distal to balloon 102" than within balloon 102".

Balloon 102" may include a shape that is particularly beneficial for implantation in the pulmonary artery. As illustrated, balloon 102" may have proximal taper 130 and distal taper 132. The shape of balloon 102" between proximal taper 130 and distal taper 132 may be cylindrical, as shown. The angle of taper of proximal taper 130 and distal taper 132 may be different. As illustrated, the angle of taper of proximal taper 130 relative to the longitudinal axis of conduit 104" may be greater than the angle of taper of distal taper 132 relative to the longitudinal axis. Such design provides optimal fluid dynamics within the pulmonary artery. Length L between distal tip 105" and tether wire exit port may be about 900-1100 mm, for example about 1000 mm. Outer diameter D of conduit 104" may be about 4-6 mm, for example, about 4.8 mm. The distance X from the distal end of balloon 102" to distal tip 105" may be about 20-30 mm, for example about 25 mm.

Figure 1F:
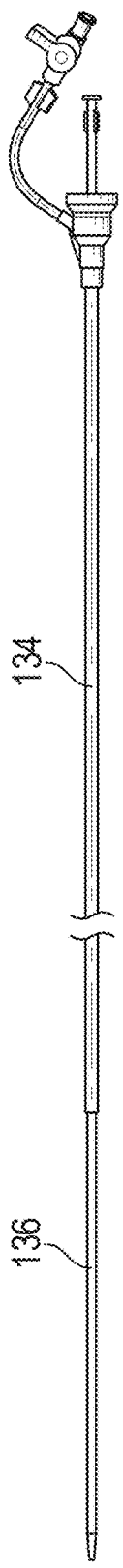
FIG. 1F illustrates an exemplary guide catheter and dilator that may be used to deliver one or more components of the implantable devices of FIGS. 1A-1E.

FIG. 1F illustrates exemplary guide catheter 134 and dilator 136 that may be used to deliver one or more components of the implantable devices of FIGS. 1A-1E. Dilator 136 is preferably inserted into guide catheter 134 until the hub of dilator 136 hub bottoms onto the hub seal of guide catheter 134. To place guide catheter 134 in accordance with some examples, gently curve the distal end of the dilator 136 to aid in passage through the cardiac anatomy, flush dilator 136 and guide catheter 134, and pass dilator 136 over a previously inserted guidewire and into the vasculature. The system is advanced until dilator 136 resides within the left pulmonary artery. While maintaining the position of dilator 136, advance the guide catheter 134 over dilator 136 until the proximal marker band is visible distal to the pulmonary valve.

Figure 1G:
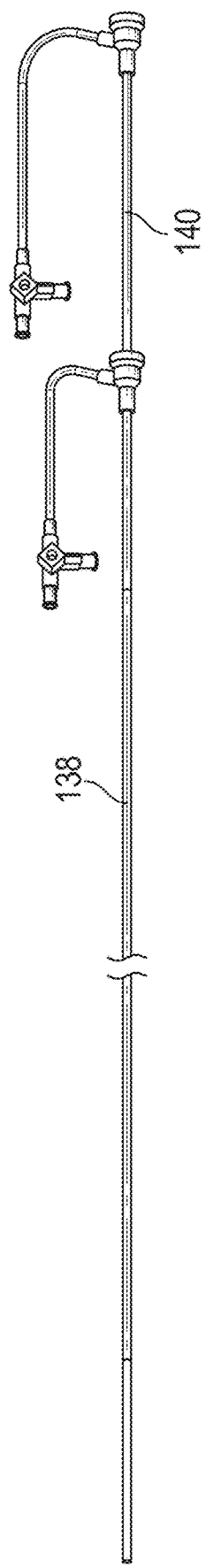
FIG. 1G illustrates an exemplary anchor loader catheter and pusher catheter that may be used to deliver or more components of the implantable devices of FIGS. 1A-1E.

FIG. 1G illustrates exemplary anchor loader catheter 138 and pusher catheter 140 that may be used to deliver or more components of the implantable devices of FIGS. 1A-1E. Exemplary steps to implant the anchor are described. Aspects of these steps are further illustrated in FIGS. 15A-15D described below. Flush anchor loader catheter 138 and pusher catheter 140 with sterile saline until all visible air is removed from anchor loader catheter 138. Remove dilator 136 and guidewire from guide catheter 134. Insert anchor loader catheter 138 into guide catheter 134 hub. Advance anchor 108" through guide catheter 134 by pushing pusher catheter 140 through anchor loader catheter 138. When anchor 108" reaches the end of guide catheter 134 but is not yet deployed, make sure that the marker band on the pusher catheter 140 is distal to the pulmonary valve. Deploy anchor 108" by maintaining the position of pusher catheter 140 and retracting guide catheter 134 until anchor 108" is engaged in the vessel. If repositioning of anchor 108" is necessary, maintain position of the pusher catheter 140 to the tether wire and advance guide catheter 134 until anchor 108" is recaptured into guide catheter 134. Adjust the position of the system and redeploy anchor 108" by retracting guide catheter 134. Withdraw pusher catheter 140 back to the Pin Vise on the tether extension system. While maintaining tether wire position, retract guide catheter 134 to the Pin Vise on the tether extension system until guide catheter 134 is removed from the vascular access site. Managing the tether wire position at the access site and managing the tether wire to extension tube position relative to the tether wire, remove the Pin Vise from the tether extension system and remove pusher catheter 140, anchor loader catheter 138 and guide catheter 134 from the tether wire.

Anchor 108 and the distal tip 105 of conduit 104, or anchor 108' and the distal tip 105' of conduit 104', or anchor 108" and the distal tip 105" of conduit 104", may have any suitable configuration that facilitates engagement of the anchor with a blood vessel and detachable engagement of the distal tip with the anchor so as to anchor the respective compliant member within that blood vessel. For example, FIGS. 2A-2I schematically illustrate exemplary configurations of components of the implantable device of FIGS. 1A-1C, in accordance with the principles of the present disclosure.

FIGS. 2A-2I schematically illustrate components of an exemplary configuration of anchor 108 that may be used in device 100 illustrated in FIG. 1A, device 100' illustrated in FIG. 1B, or device 100" illustrated in FIG. 1C, and that is configured to detachably engage the distal tip of the respective conduit 104, 104', or 104". Anchor 108 includes expandable structure 200 configured to engage a blood vessel when in a deployed state. In some configurations, expandable structure 200 is configured so as to contact the blood vessel wall, but to express only enough pressure on the blood vessel wall so as to stabilize the compliant member 102 or 102' via the coupling between anchor 108 and the compliant member, without expressing excess force that would promote unneeded remodeling of the vessel. Expandable structure 200 may include a plurality of structural members 201 coupled to one another, each structural member 201 including any suitable number of struts.

Figure 2B:
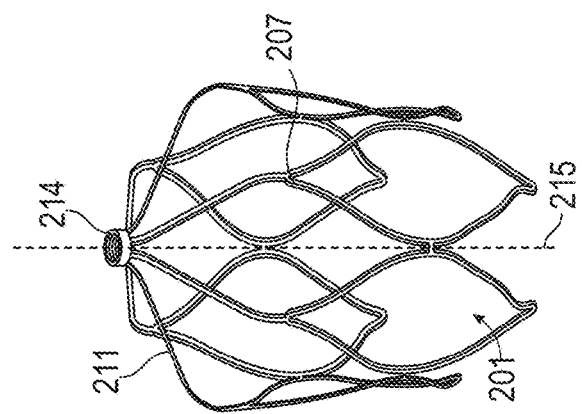
Figure 2C:
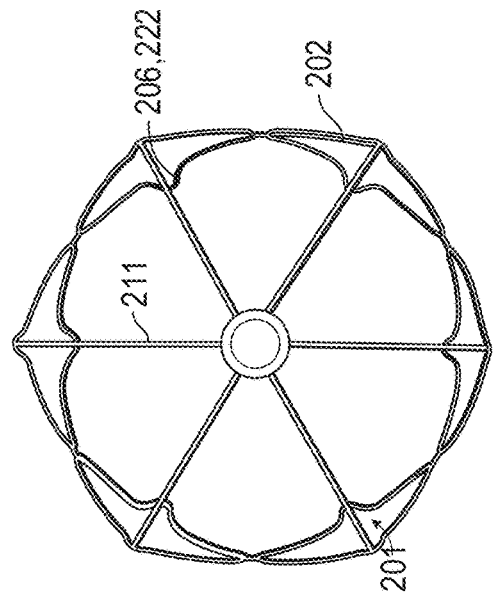
Figure 2A:
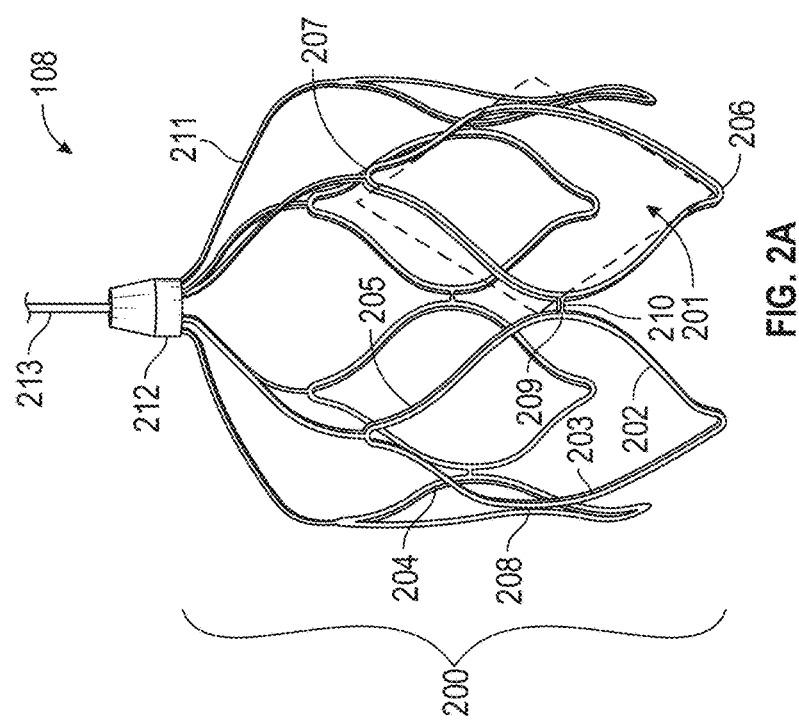

For example, each structural member 201 illustrated in FIG. 2A may be approximately the shape of a diamond, such as indicated in dotted lines, and may have, for example, four struts 202, 203, 204, 205. Struts 202 and 203 of each structural member 201 meet at an acute angle at the bottom apex 206 of that structural member. Struts 204 and 205 of each structural member 201 meet at an acute angle at the top apex 207 of that structural member. Struts 203 and 204 of each structural member 201 meet at an obtuse angle at a first side apex 208 of that structural member. Struts 202 and 205 of each structural member 201 meet at an obtuse angle at a second side apex 209 of that structural member. Expandable structure 200 also may include connector struts 210 coupling the first side apex 208 of each structural member 201 to the second side apex 209 of an adjacent structural member 201. Struts 204, 205 of each diamond-shaped structural member 201 may be cut with a taper producing a thinner strut width at approximately midway between apexes 207, 206, e.g., at approximately the respective side apexes 208, 209 of that structural member 201. Struts 202, 203 of each diamond-shaped structural member 201 may be cut with a tapered thinning away from the bottom apex 207 to the respective side apexes 209, 208 of that structural member 201. Such tapers may serve to create a more even distribution of the strain experienced by expandable structure 200. Optionally, the bottom apex 206 of each structural member 201 of expandable structure 200 may be rolled inward toward an interior of expandable structure 200, for example, toward the longitudinal axis 215 of expandable structure 200 such as indicated in dotted line in FIG. 2B, so as to create an atraumatic termination 222. Optionally, expandable structure 200 may be compressed to a delivery state in a manner such as described further below with reference to FIGS. 3A-3C.

Optionally, expandable structure 200 also includes bridging struts 211 and anchor ring 214. In some configurations, each bridging strut 211 couples the top apex 207 of a respective structural member 201 to anchor ring 214. In some configurations, anchor ring 214 may be axially centered to expandable structure 200, and may be or include a portion of a tube from which anchor 108 is cut. Anchor ring 214 may be coupled to optional docking hub 212 illustrated in FIG. 2A and as further explained below. Bridging struts 211 may be configured such that when anchor 108 is implanted into a blood vessel, bridging struts 211 provide a gradual disengagement with the blood vessel wall from the distal end of expandable structure 200 (e.g., from atraumatic terminations 222) to the proximal end of expandable structure 200 (e.g., to anchor ring 214 or docking hub 212). Bridging struts 211 may have any suitable angle relative to anchor ring 214 and to axis 215, e.g., may have an angle of about 30° and about 150° relative to axis 215, or an angle of about 60° and about 120° relative to axis 215, or an angle of about 70° and about 70° relative to axis 215, in one nonlimiting configuration an angle of about 80° relative to axis 215. The angle formed by bridging struts 211 may decrease when implanted and changes with the diameter of the vessel to be treated. Bridging struts 211 may be designed to inhibit migration of expandable structure 200 while interfering minimally with the blood flow through the blood vessel.

In some configurations, anchor 108 is formed from a single piece of NiTi tube that is laser cut and expanded through heat treatment cycles. To reduce the radial outward force that is appropriate to inhibit migration of expandable structure 200 within a blood vessel, the surface roughness of expandable structure 200 optionally may be modified to increase the static friction coefficient of the metallic surface. This rougher surface may be obtained, for example, by pickling and passivating expandable structure 200, for example instead of electropolishing expandable structure 200. Pickling substantially removes titanium oxide and nickel rich layers from the outer surface of the expandable structure 200 substantially without removing the underlying crystalline stable NiTi, leaving a rougher surface than industry standard practices of electropolishing. Passivation removes surface impurities from the expandable structure 200 after pickling, and grows a thin protective oxide layer on the part. The result of such pickling and passivation procedures is a matte finish that is still highly corrosion resistant. Optionally, the outer surface of expandable structure 200 may have small barbs that inhibit migration in vivo.

Anchor 108 optionally may include a docking hub configured to receive and detachably engage the distal tip 105 of conduit 104. For example, in the configuration illustrated in FIGS. 2A and 2D-2I, anchor 108 includes tether wire 213, and optionally further includes docking hub 212 which may be configured so as to couple expandable structure 200 to tether wire 213. Tether wire 213 may be disposed within conduit 104 in a manner such as indicated in FIGS. 1A and 2D-2I. In some configurations, when the distal tip 105 of conduit 104 is engaged with anchor 108, the compliant member 102 is anchored within the blood vessel, and when distal tip 105 is disengaged from anchor 108, the conduit 104 and compliant member 102 are movable along tether wire 213 relative to the anchor in a manner such as described below with reference to FIGS. 15A-15I. In some configurations, tether wire 213 has a length greater than the length of conduit 104 and may extend through all or substantially all of conduit 104. For example, tether wire 213 may extend through a lumen of conduit 104 and into the reservoir or may be exposed at an opening at the proximal end of conduit 104 or in the reservoir so the proximal end of tether wire 213 is accessible. In one example, the proximal end of tether wire 213 is subcutaneously implanted, e.g., in a coiled configuration, such that conduit 104 and/or compliant member 102 are removable and replaceable over the proximal end of tether wire 213 upon surgical exposure of the proximal end.

For example, in some configurations, docking hub 212 is configured to be coupled to expandable structure 200 at the distal end of docking hub 212 via anchor ring 214 and connector 216, as further explained below. Docking hub 212 is coupled to tether wire 213 at the proximal end of docking hub 212. Docking hub 212 thus serves as an optional connecting member between anchor 108 and tether wire 213, as well as a mating/sealing member with which compliant member 102 interfaces via the distal tip 105 of conduit 104. Tether wire 213 provides a guide for conduit 104 as the conduit 104 is advanced through the blood vessel in a manner such as described with reference to FIGS. 15A-15I. Once conduit 104 is in place within the blood vessel, tether wire 213 may enhance the body of the conduit, stiffening the conduit slightly. To make welding of tether wire 213 to docking hub 212 more robust, kink resistant, and MRI compatible, tether wire 213 optionally may be made of superelastic NiTi. Tether wire 213 may be configured so as to provide a relatively smooth surface over which compliant member 102, such as a balloon, and conduit 104 can advance in a manner such as described with reference to FIGS. 15A-15I. Such a smooth surface may be provided, for example, through mechanical polishing and passivation after final assembly, or by applying a coating such as polytetrafluoroethylene (PTFE). Tether wire 213 may also or alternatively be or include a braided wire, a multifilar wire, or a monofilament wire. Additionally, or alternatively, tether wire 213 may be or include a polymer, stainless steel NiTi alloy, tertiary NiTi alloy, titanium, or MP35N alloy.

Figure 2F:
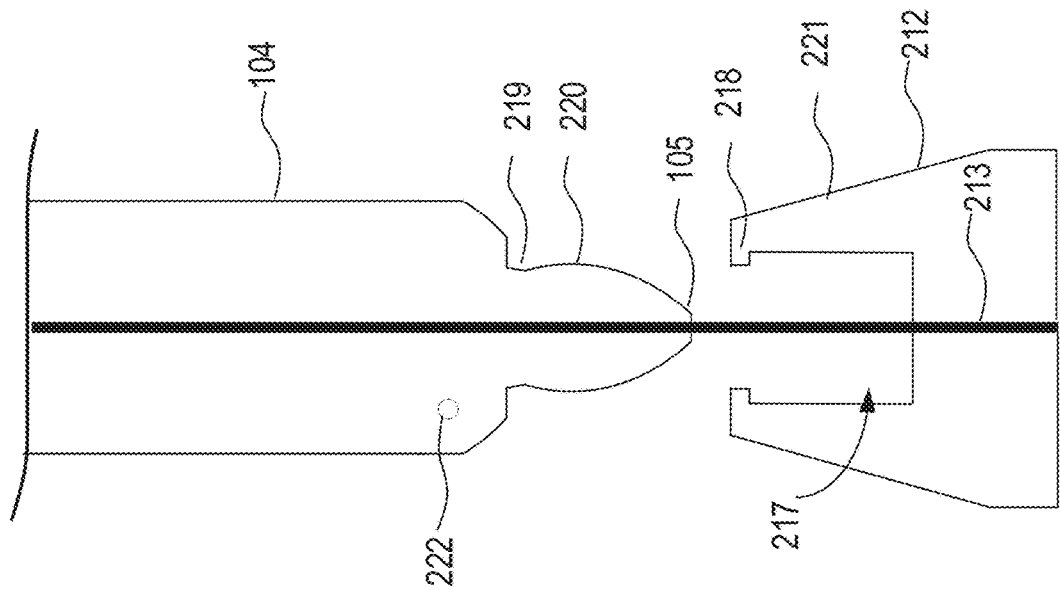
Figure 2E:
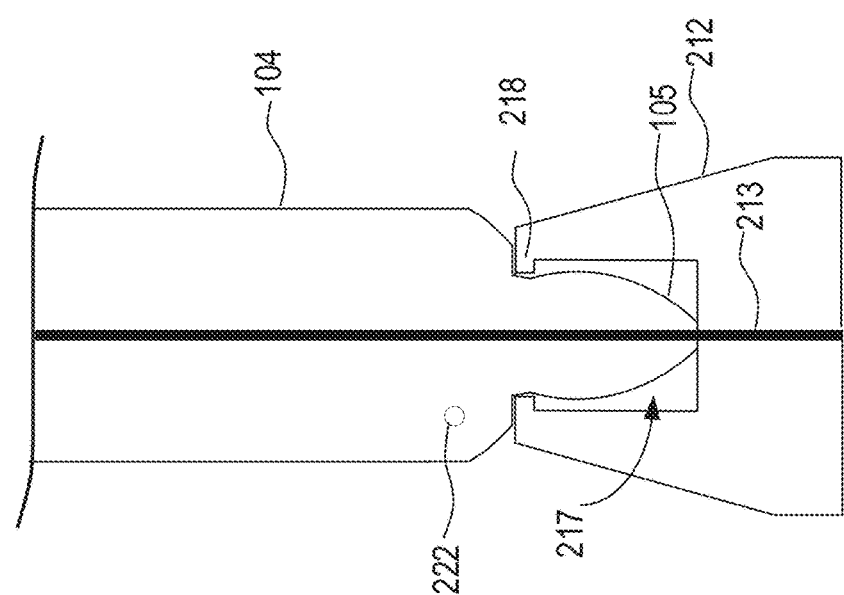
Figure 2D:
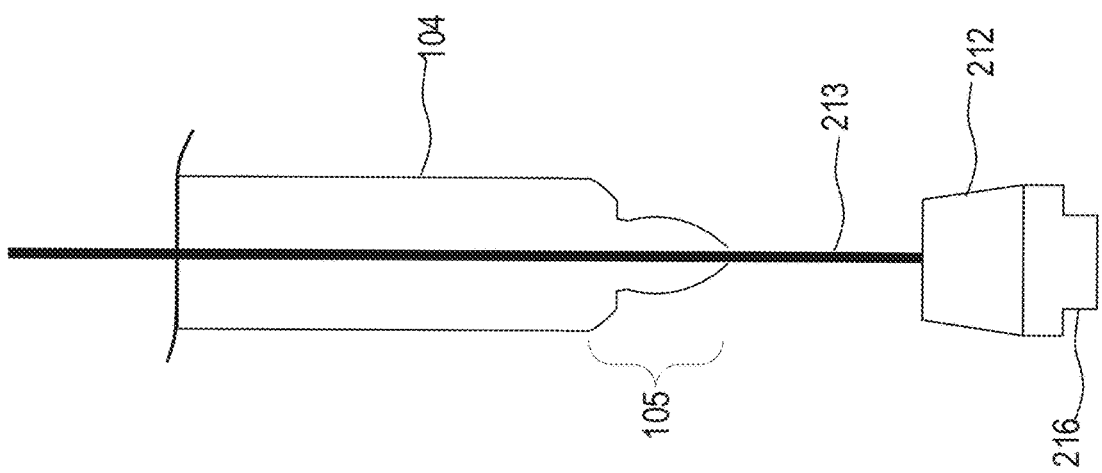

As illustrated in FIG. 2D, docking hub 212 optionally may be coupled to or may include connector 216. Connector 216 may have an outer diameter matching the inner diameter of anchor ring 214 and an inner diameter matching the outer diameter of the tether wire 213. In some configurations, tether wire 213 distally terminates within docking hub 212, and anchor 108 proximally terminates over docking hub 212 via connector 216. Laser welding, a concentrated laser to heat two contacting NiTi components, may be used to couple tether wire 213 to docking hub 212, may be used to couple docking hub 212 to connector 216, and/or may be used to couple connector 216 to anchor ring 214. Anchor 108 optionally may be cut from a relatively large NiTi tube, for instance having a 2.0 to 5.0 mm (e.g., 3.4 mm) outer diameter and a 0.1 to 0.5 mm (e.g., 0.25 mm) wall. Tether wire 213 optionally may have a diameter of 0.2 to 0.5 mm, for example, 0.373 mm. It should be understood that such dimensions are intended to be purely illustrative, and not intended to be limiting. Additionally, it should be understood that any suitable combination of techniques may be utilized to couple docking hub 212 to tether wire 213 and anchor 108. For instance, distal tip 105 of conduit 104 may include one or more structural members that are driven radially outward when advanced over docking hub 212 and recover radially inward once past docking hub 212. Such structural member(s) may include a catch to inhibit or prevent distal tip 105 of conduit 104 from disengaging from docking hub 212 by moving proximally. Alternatively, distal tip 105 of conduit 104 may include a threaded interface that threads together with a threaded interface in docking hub 212. Another exemplary variation may include a pin inserted through anchor ring 214 and docking hub 212 and welded to anchor ring 214 on both sides.

In some configurations, docking hub 212 may work in conjunction with conduit 104 so as to inhibit conduit 104 from inadvertently migrating along tether wire 213 and to seal the interior of conduit 104 from the blood environment of the blood vessel. Any suitable configuration may be used to create this retention and seal, either alone or in conjunction with other features. For example, the distal tip 105 of conduit 104 may include a detent, and docking hub 212 may include a protrusion that detachably engages the detent. Illustratively, a snap interface such as shown in FIGS. 2E-2I may be configured so as to allow for tuning of the insertion and extraction forces, for example through geometric modifications of distal tip 105 of conduit 104, and to provide a smooth transition from the surface of docking hub 212 to the surface of distal tip 105 of conduit 104 which may reduce or minimize locations for clot growth in the area. In the illustrated configuration, the proximal end of docking hub 212 includes cavity 217 configured to receive distal tip 105. Cavity 217 may include a protrusion such as retention ridge 218 which partially covers the proximal end of cavity 217. Distal tip 105 may include a detent 219 and shoulder 220 configured such that when distal tip 105 is inserted into cavity 217, shoulder 220 pushes out retention ridge 218 until the shoulder passes beyond retention ridge 218 and retention ridge 218 engages with detent 219. Distal tip 105 may also or alternatively include a semi-malleable retention ring or retaining O-ring which may secure distal tip 105 in cavity 217, for example in a manner such as described with reference to FIGS. 2G-2H. Cavity 217 may be sufficiently large as to accommodate a soft-deform material that may be molded into distal tip 105, 105', or provided as a floating insert, to create an additional seal.

As also illustrated in FIGS. 1A-1C, 2A, and 2D-2I, the outer surface of docking hub 212 optionally may include a sloped surface 221 configured to engage with a sheath. For example, should it be desired to retrieve anchor 108 from a blood vessel, the sloped surface of docking hub 212 should help guide docking hub 212 into the sheath which may be used as a retrieval catheter. As another example, should it be desired to replace compliant member 102 with another such compliant member, may serve as a reference for a sheath, such as a balloon exchange catheter, to push against during an extraction, isolating anchor 108 from any exchange forces. Further, conduit 104 optionally may include radiopaque marker 222 configured to permit visualization of location of distal tip 105 relative to docking hub 212. Alternatively, distal tip 105 may be radiopaque.

Figure 2H:
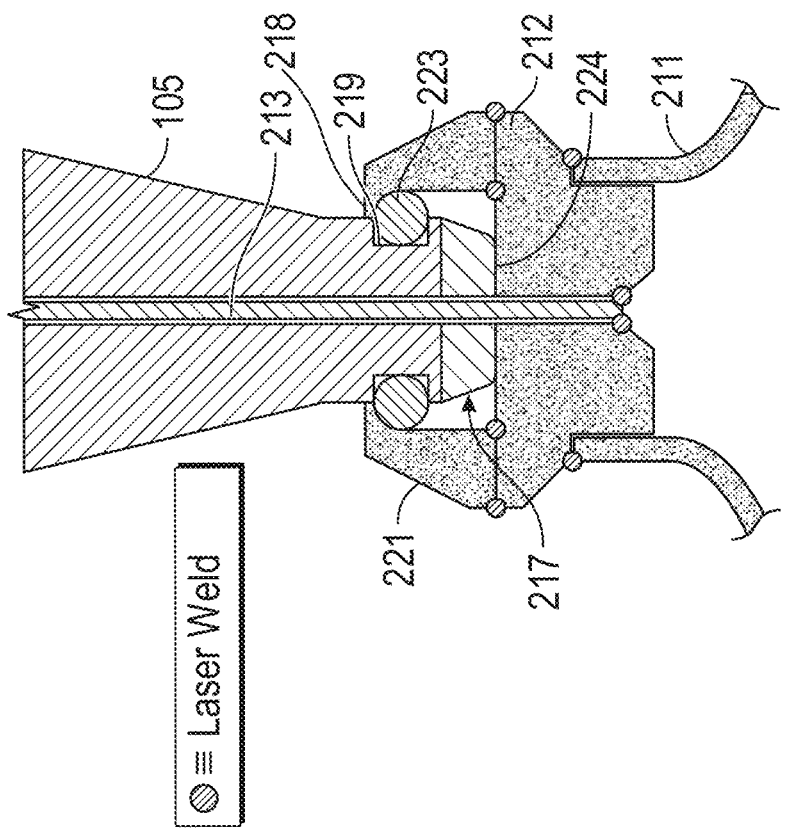
Figure 2G:
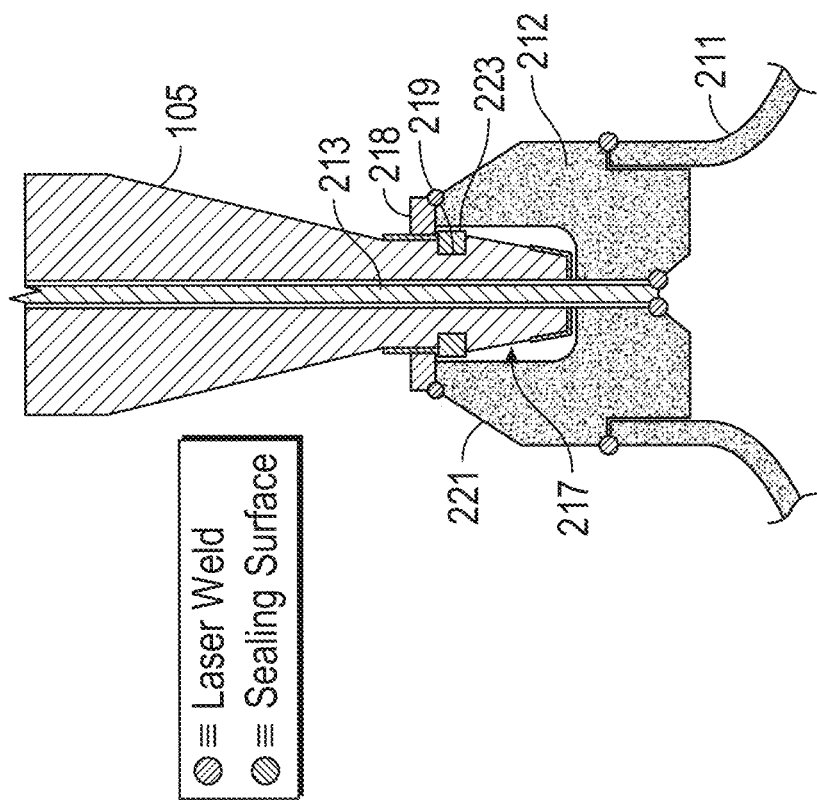

FIG. 2G illustrates an exemplary configuration including a snap interface similar to that illustrated in FIGS. 2D-2F, including docking hub 212 with retention ridge 218 engaging with detent 219 of radiopaque distal tip 105, and which further includes a semi-malleable retention ring 223 disposed within detent 219. Docking hub 212 and retention ridge 218 may be laser welded to one another in a manner such as illustrated in FIG. 2G, or docking hub 212 may be integrally formed with retention ridge 218. Additionally, or alternatively, docking hub 212 may be laser welded to struts 211, and may be laser welded to tether wire 213. Sealing surfaces may be provided by one or more of engagement of distal tip 105 with retention ridge 218, of retention ring 223 with detent 219 and docking hub 212, or of the terminal surface of distal tip 105 with the inner surface of cavity 217, for example as indicated in FIG. 2G. FIG. 2H illustrates another exemplary configuration including a snap interface similar to that illustrated in FIGS. 2D-2G, including docking hub 212 with retention ridge 218 engaging with detent 219 of radiopaque distal tip 105, and which further includes O-ring 223 disposed within detent 219. Docking hub 212 and retention ridge 218 may be laser welded to one another in multiple locations in a manner such as illustrated in FIG. 2H. Additionally, or alternatively, the upper surface of docking hub 212 may be flat, and the sidewalls of cavity 217 provided by the sidewalls of retention ridge 218. Additionally, or alternatively, docking hub 212 may be laser welded to struts 211, and may be laser welded to tether wire 213. Sealing surfaces may be provided by one or more of engagement of distal tip 105 with retention ridge 218, of retention ring 223 with detent 219 and docking hub 212, or of the terminal surface of distal tip 105 with the inner surface of cavity 217, for example as indicated in FIG. 2H. Optionally, distal tip 105 may include a soft material 224 at its terminal end, facilitating a seal between the distal tip 105 and the upper surface of docking hub 212.

FIG. 2I illustrates another exemplary configuration including a snap interface similar to that illustrated in FIGS. 2D-2H, including docking hub 212 with retention ridge 218 engaging with detent 219 of radiopaque distal tip 105 (e.g., including barium-loaded polymers, or polycarbonate-based thermoplastic urethanes such as CHRONOFLEX®, which is commercially available from AdvanSource Biomaterials Corporation (Wilmington, MA)). Docking hub 212 and retention ridge 218 may be laser welded to one another in a manner such as illustrated in FIG. 2I. Additionally, or alternatively, docking hub 212 may be laser welded to struts 211, and may be laser welded to tether wire 213. Sealing surfaces may be provided by one or more of engagement of distal tip 105 with retention ridge 218, of retention ring 223 with detent 219 and docking hub 212, or of the terminal surface of distal tip 105 with the inner surface of cavity 217, for example as indicated in FIG. 2I. Optionally, cavity 217 may be configured so as to provide a space for soft deform material to be molded into distal tip 105 so as to provide an additional seal between the distal tip 105 and the upper surface of docking hub 212, e.g., in a manner such as described with reference to FIG. 2H, or for a free-floating insert to be provided so as to provide such a seal.

Although the particular configuration of expandable structure 200 illustrated in FIGS. 2A-2C includes six diamond-shaped structural members 201 that are coupled to one another via connector struts and that are coupled to anchor ring 214 via respective bridge struts 211, it should be understood that the expandable structure may include any suitable number of structural members that are of any suitable shape and are coupled to anchor ring 214 and/or to one another in any suitable manner. Other non-limiting examples of expandable structures are described elsewhere herein with reference to FIGS. 9A-13C.

FIG. 2J provides further top, side, and perspective views of anchor 108. FIGS. 2K and 2L show the anchor as it is cut from a tube, with FIG. 2K showing a flattened version and FIG. 2L showing a tubular version.

Figure 3A:
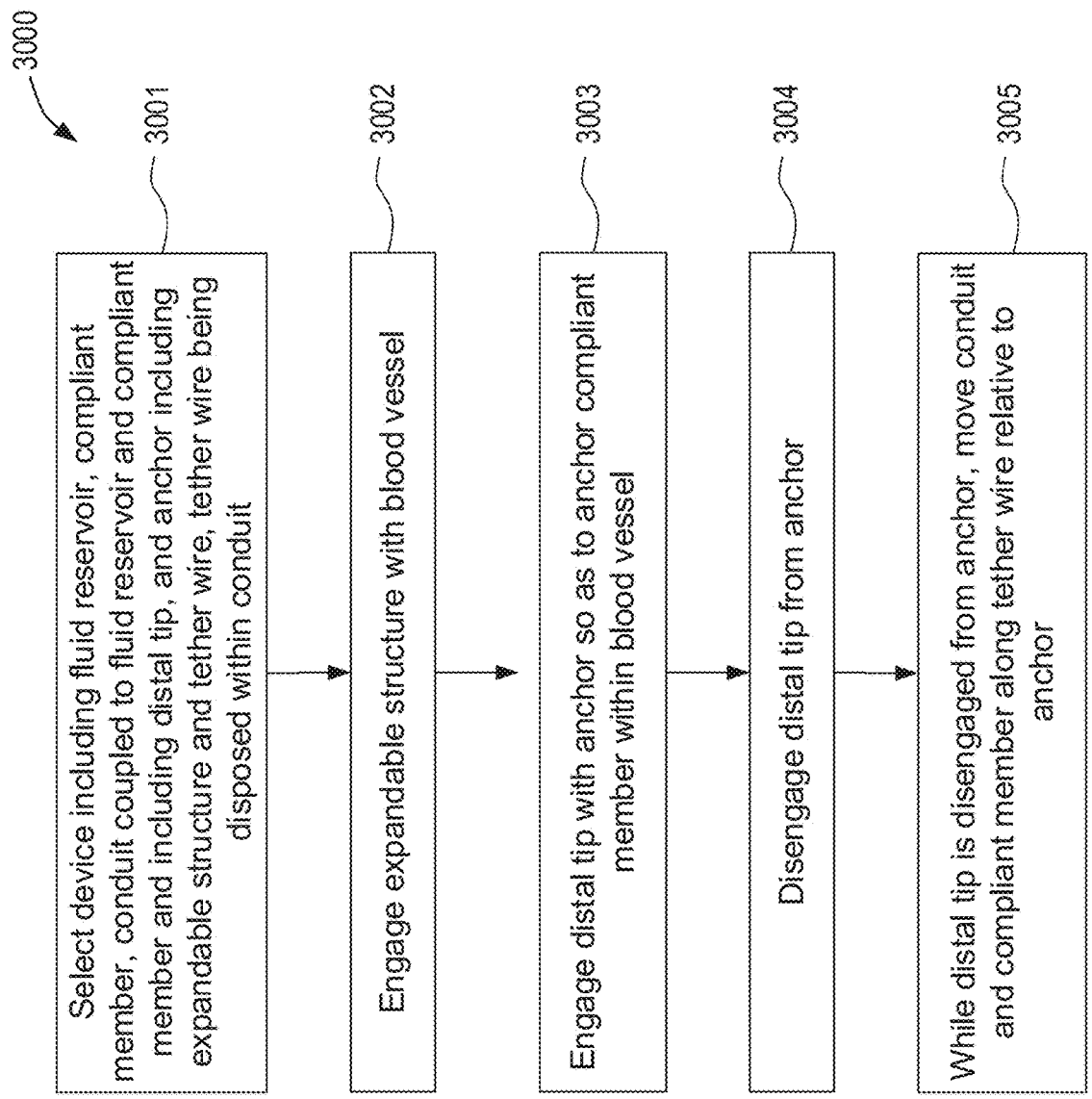
FIG. 3A illustrates an exemplary flow of operations in a method for delivering and moving an implantable device including an anchor and a detachable compliant member for reducing pulsatile pressure within a blood vessel, in accordance with the principles of the present disclosure.

It should be appreciated that devices such as described herein suitably may be delivered to, retrieved from, and used in any suitable blood vessel. For example, FIG. 3A illustrates an exemplary flow of operations in a method 3000 for delivering and moving an implantable device including an anchor and a detachable compliant member for reducing pulsatile pressure within a blood vessel. Method 3000 includes selecting a device (operation 3001). The selected device may be configured such as described with reference to FIGS. 1A-1C and 2A-2I, for example may include a fluid reservoir (e.g., reservoir 106), a compliant member (e.g., compliant member 102), a conduit coupled to the fluid reservoir and the compliant member and including a distal tip (e.g., conduit 104), and an anchor (e.g., anchor 108). The anchor may include an expandable structure (e.g., expandable structure 200) and a tether wire (e.g., tether wire 213), the tether wire being disposed within the conduit (e.g., within conduit 104).

Method 3000 illustrated in FIG. 3A may include engaging the expandable structure with a blood vessel (operation 3002). Method 3000 also may include engaging the distal tip with the anchor so as to anchor the compliant member within the blood vessel (operation 3003). For example, FIG. 3B schematically illustrates the device of FIGS. 1A-1C and 2A-2I in a delivery state in which the anchor is contracted within a sheath within a blood vessel, such as the pulmonary artery.

In FIG. 3B, expandable structure 200 of anchor 108 is in a compressed or constrained state within sheath 300, which is disposed inside of blood vessel 310. In the example shown in FIG. 3B, the distal tip 105 of conduit 104 is detachably coupled to anchor 108 in the delivery state, for example via a docking hub 212 or other structure such as described elsewhere herein. Compliant member 102 may be in a collapsed, deflated state when inserted into blood vessel 310 within sheath 300.

FIG. 3C schematically illustrates the device of FIGS. 1A-1C and 2A-2I in a deployed state in which the anchor expands to engage the blood vessel. For example, expandable structure 200 may self-expand to engage with blood vessel 310 responsive to retraction of sheath 300. In FIG. 3C, one or more struts of structural members contact and engage with the inner wall of the blood vessel 10, e.g., pulmonary artery, so as to anchor compliant member 102, which coupled thereto via docking hub 212, within the blood vessel. After deployment of anchor 108 and compliant member 102 past the distal end of sheath 300, sheath 300 may be removed from the patient or may be permanently implanted at a position such that the distal end of sheath 300 does not interfere with expansion of compliant member 102 or anchor 108 and the proximal end of sheath 300 does not interfere with coupling the proximal end of conduit 104 to reservoir 106. One or both of anchor 108 and compliant member 102 also or alternatively may be permanently implanted within the patient. By "permanently implanted" it is meant that the component(s) remain within the blood vessel for a period of days, weeks, months, or years. Anchor 108 and compliant member 102 may be, but need not necessarily be, permanently implanted in the blood vessel for the same amount of time as one another. For example, in some configurations, anchor 108 remains within the blood vessel for a period of years, while compliant member 102 remains within the blood vessel for a shorter period than that of anchor 108.

Figure 15B:
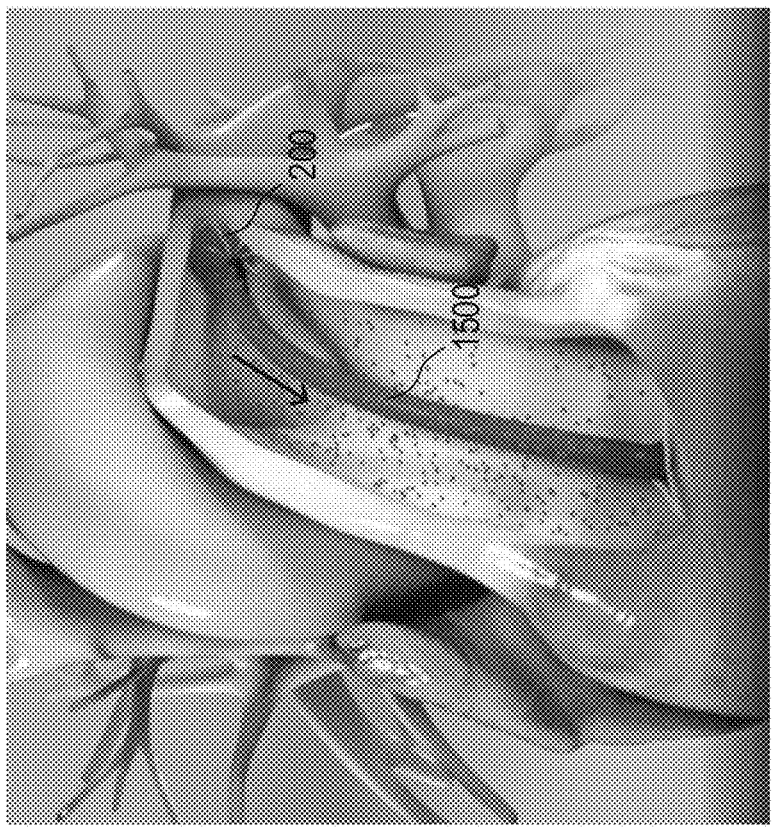
FIGS. 15A-15I schematically illustrate use of the implantable device of FIGS. 1A-1C during the method of FIG. 3A in accordance with the principles of the present disclosure.
Figure 15A:
Figure 15D:
Figure 15C:
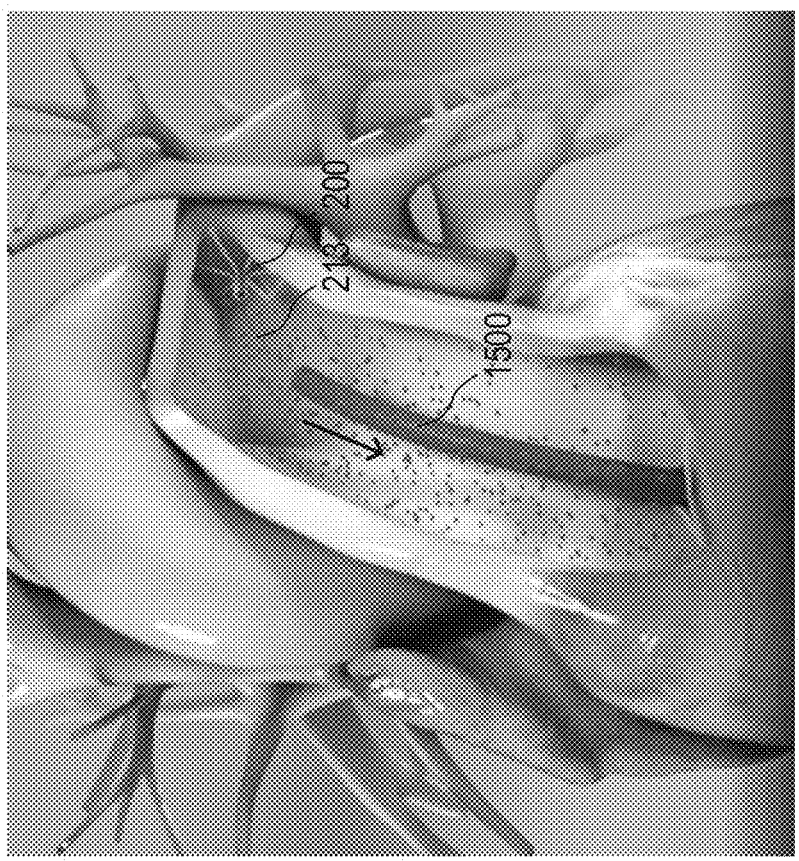
Figure 15F:
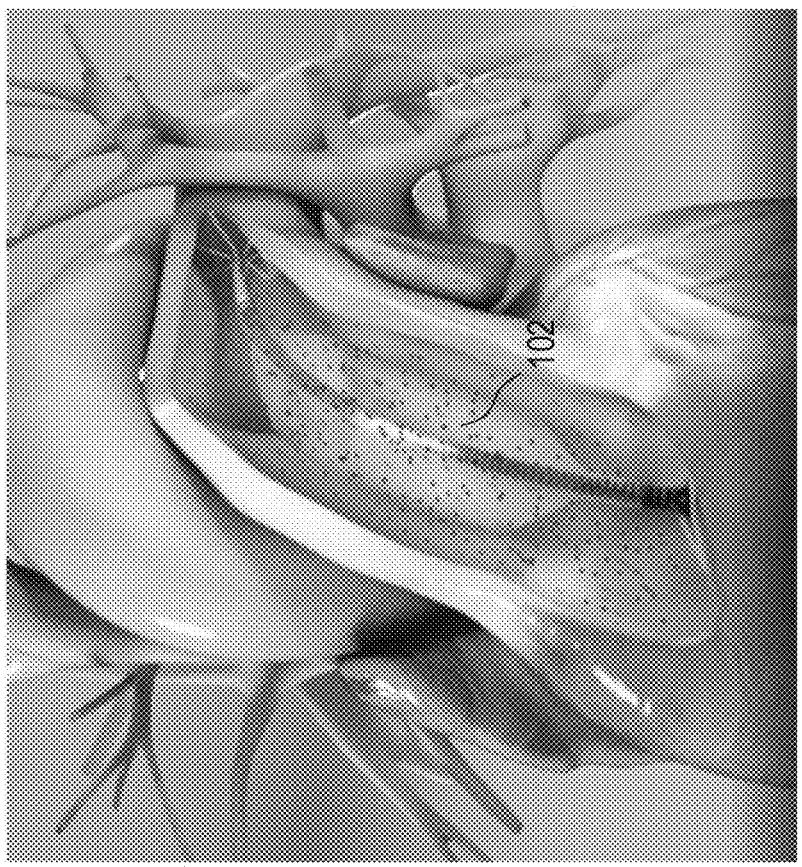
Figure 15E:
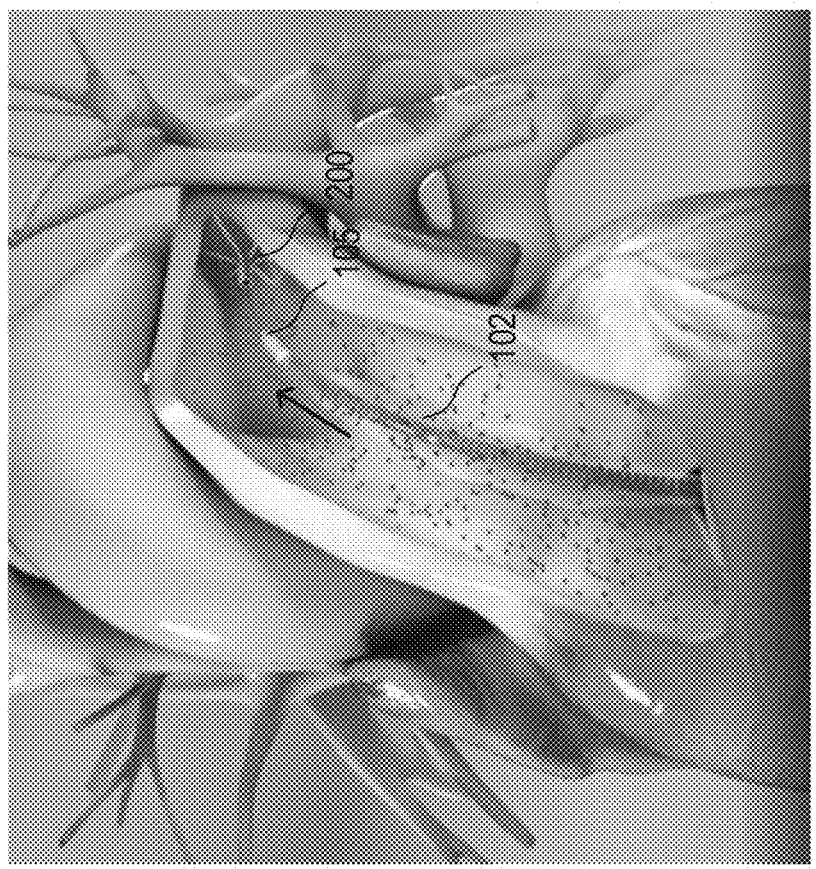
Figure 15G:
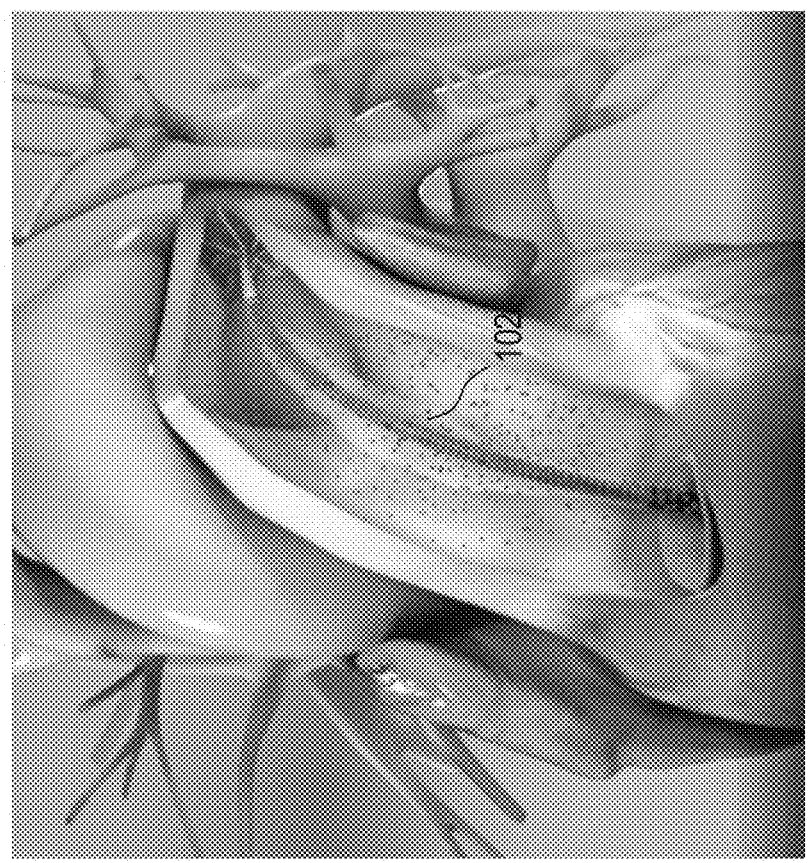

Although FIGS. 3B-3C illustrate conduit 104 as being coupled to anchor 108 prior to and during insertion and retraction of sheath 310 within blood vessel 300, it should be appreciated that operations 3002 and 3003 of method 3000 do not necessarily require the distal tip 105 of conduit 104 to be coupled to anchor 108 throughout the entire delivery process. For example, FIGS. 15A-15I schematically illustrate use of the implantable device of FIGS. 1A-1C during the method of FIG. 3A in accordance with the principles of the present disclosure. In the example shown in FIGS. 15A-15I, sheath 1500 may be used to deliver expandable structure 200 of anchor 108 within blood vessel 1510 in a manner similar to that shown in FIGS. 3B and 3C, but without conduit 104 being coupled to anchor 108. For example, at the time shown in FIG. 15A, expandable structure 200 of anchor 108 is in a compressed or constrained state within sheath 1500, which is disposed inside of blood vessel 1510 such as the pulmonary artery. At the time shown in FIG. 15B, expandable structure 200 is expanded at a desired location within blood vessel 1510 by retracting sheath 1500 relative to tether wire 213. At the time shown in FIG. 15C, sheath 1500 is further retracted, and expandable structure 200 is fully expanded so as to engage the desired location within blood vessel 1510. At the time shown in FIG. 15F, sheath 1500 is completely retracted, and it may be seen that tether wire 213 extends out of the heart. At the time shown in FIG. 15E, conduit 104 is delivered over tether wire 213, and at the time shown in FIG. 15F, distal tip 105 of conduit 104 engages with anchor 108 while expandable structure 200 is engaged with the blood vessel. Regardless of the order in which anchor 108 and compliant member 102 are delivered into blood vessel 310, after delivery, compliant member 102 may be expanded by introduction of fluid from reservoir 106 through port 120 in a manner such as illustrated in FIG. 15F, and compressed responsive to increased pulsatile pressure in a manner such as illustrated in FIG. 15G.

Figure 15H:
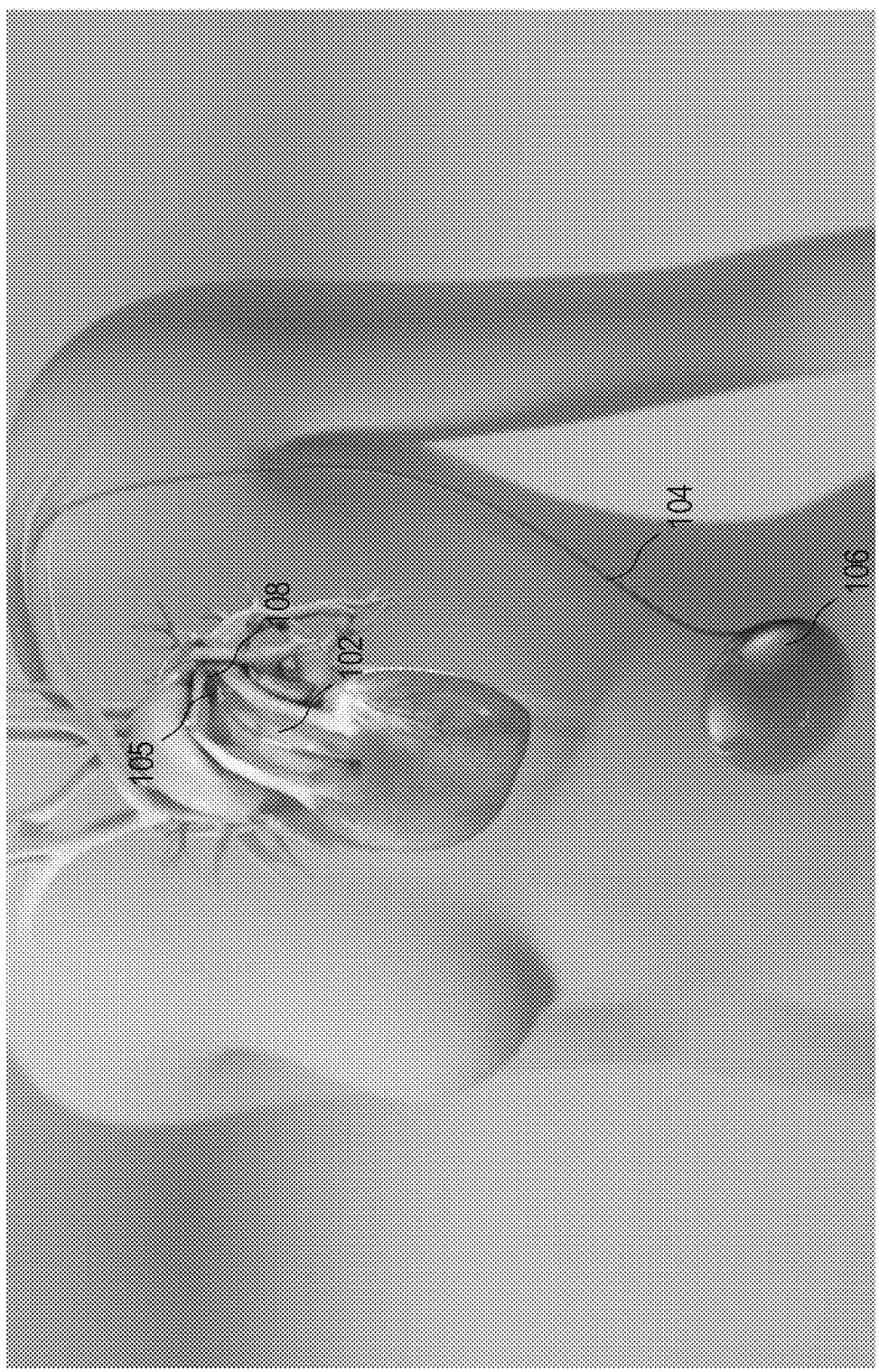

FIG. 15H illustrates additional components of the device of FIGS. 1A-1C during the time illustrated in FIG. 15F, as implanted in the body. As shown in FIG. 15H, compliant member 102 is in the expanded state. In this image, reservoir 106 is implanted subcutaneously over the left upper abdomen. Conduit 104 has an intravascular segment and an extravascular segment, and the two segments are fluidly coupled and meet where the conduit penetrates the subclavian vein. The extravascular segment is located subcutaneously and is connected to the reservoir. The intravascular segment extends from the subclavian vein to the compliant body implanted in the pulmonary artery. Specifically, in the exemplary implanted state shown in this image, the reservoir is implanted subcutaneously superficial to the left upper abdomen with the conduit extending subcutaneously from the reservoir, along the left lateral thorax, into an opening created in the subclavian vein, into the superior vena cava, through the right atrium and ventricle, through the pulmonary valve, and into the pulmonary artery such that the balloon is implanted in the pulmonary artery.

Figure 15I:
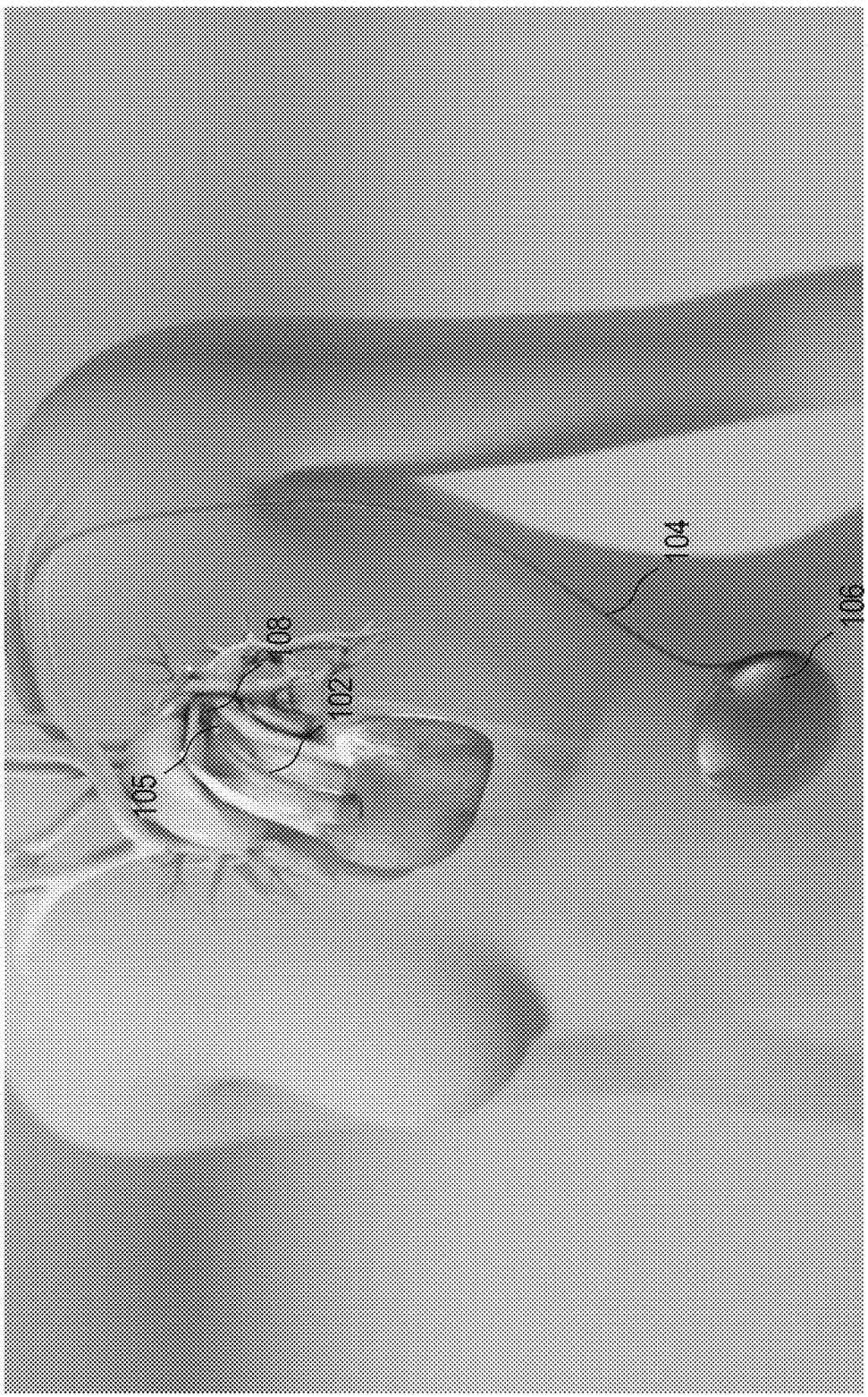

FIG. 15I illustrates additional components of the device of FIGS. 1A-1C during the time illustrated in FIG. 15G, as implanted in the body. As shown in FIG. 15I, compliant member 102 is in the compressed state. Compliant member 102 cycles between the expanded state (FIG. 15H) and the compressed state (FIG. 15I) responsive to pressure change during the cardiac cycle.

As noted elsewhere herein, anchor 108 may be configured to detachably engage the distal tip 105 of conduit 104, thus facilitating exchange of one or both of compliant member 102 and conduit 104 while anchor 108 remains in place within blood vessel 310. For example, method 3000 optionally further includes disengaging distal tip 105 from anchor 108 (operation 3004). Illustratively, a sheath (not illustrated) may be advanced over conduit 104 and over compliant member 102 that has an internal diameter sufficiently small as to engage docking hub 212, for example at or along sloped surface 221. That sheath may be pressed forward while conduit 104 is retracted, causing disengagement of distal tip 105 from docking hub 212. Method 3000 may include, while the distal tip 105 is disengaged from anchor 108, moving conduit 104 and compliant member 102 along tether wire 213 relative to anchor 108 (operation 3005). If desired, a replacement conduit and/or replacement compliant member may be introduced into the patient over tether wire 213, for example within a sheath, and the distal tip 105 of such conduit may be engaged with docking hub 212 by pressing the tip into the hub in a manner such as described with reference to FIGS. 2E-2I.

Alternatively, should it be desired to remove anchor 108 and compliant member 102 from the blood vessel together with one another, sheath 300 or 1500, or another similar sheath, may be advanced distally, or conduit 104 pulled proximally, such that compliant member 102 and anchor 108 enter the lumen of the sheath at the distal end of the sheath to return anchor 108 to the contracted state. Conduit 104, compliant member 102, and anchor 108, then may be retrieved from sheath 300 or 1500, e.g., by detaching the proximal end of conduit 104 from reservoir 106 and pulling the proximal end of conduit 104 proximally out the proximal end of the sheath.

Figure 4B:
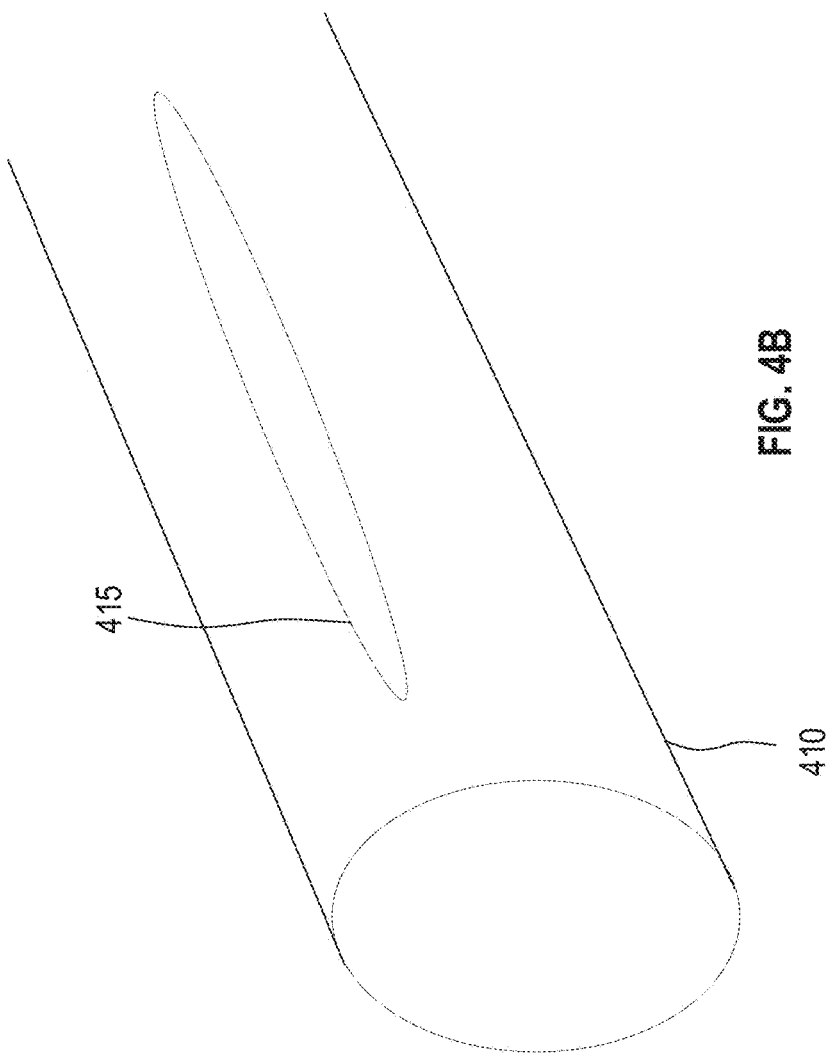
FIGS. 4A and 4B schematically illustrate an exemplary locking tube for coupling a tether wire to a tether wire extension in accordance with the principles of the present disclosure.
Figure 4A:
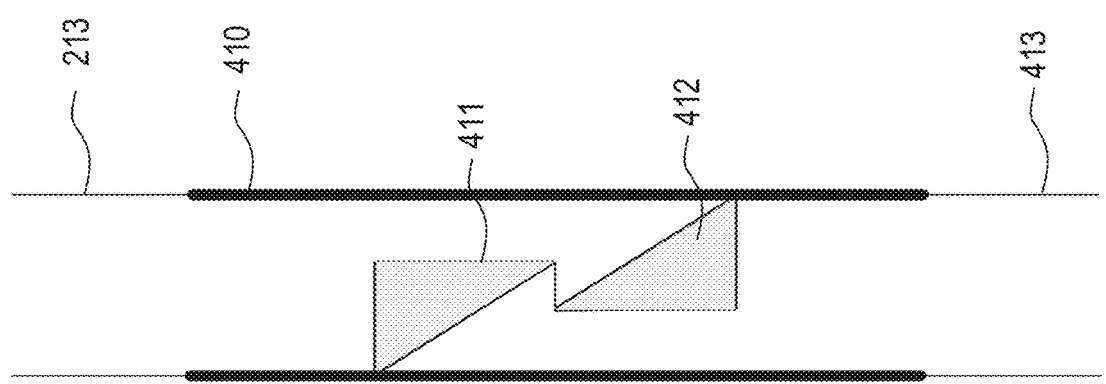

During delivery or moving of anchor 108 and/or of compliant member 102, an exchange length of tether wire 213, referred to herein as a tether wire extension, may be used. It may not necessarily be desirable to implant such a tether wire extension with the reservoir within the patient's body. Instead, a cavity within reservoir to house this length of wire may be created, or an extravascular tether wire extension 413 may be made removable. There are several ways to temporarily create a link between tether wire 213 and such a tether wire extension, which may have the same diameter as one another. For example, FIGS. 4A and 4B schematically illustrate an exemplary locking tub for coupling a tether wire to a tether wire extension, in accordance with the principles of the present disclosure. In some configurations, a locking cam profile design, as shown in FIG. 4A may be used. The tether wire extension 413 can have a first profile, and the tether wire 213 has a second profile configured to detachably engage the first profile so as to create a joint. The same profile may be ground or cut into both tether wire 213 and tether wire extension 413. The two profiles may then be brought together outside of or within a locking tube 410, for example a section of hypo-tube that has been slotted so as to allow for some expansion of locking tube 410. Such an insertion technique allows for easy alignment of the two profiles and a tactile snap when they are fully mated. Following the alignment of the two profiles, locking tube 410 may be advanced to a section with no slotting, thus locking the joint together. FIG. 4B illustrates slot 415 disposed on locking tube 410, which slot optionally may be formed by laser cutting. Optionally, assembly of the joint may be performed inside locking tube 410. For example, tether wire 213 and tether wire extension 413 respectively may include ramps 411, 412 that may be forced past each other within the section of tube 415 that includes slot 415. Once the wedges are driven past each other, locking tube 410 may be advanced distally to a non-slotted section to secure the joint.

It should be appreciated that any suitable structures may be used so as to couple components of the present devices to one another. For example, FIGS. 5A-7B schematically illustrate alternative structures for coupling a docking hub to a conduit, in accordance with the principles of the present disclosure. Now referring to FIGS. 5A-5D, alternative structures for coupling docking hub 212 to conduit 104 are shown. Shape memory radial clamping may be used by exploiting the shape memory effect of NiTi and creating components with intentional dimensional overlap, cooling the surrounding component into a martensitic phase, expanding that component using a die, and allowing the outer component to heat back up and recover onto the inner component. This may be done in combination with a barbed/profiled feature 501. For instance, features on the surface of the inner connecting component both distal and proximal to the intended overlap region 502 may be configured such that the outer component can be forced into position under considerable load, but not disassembled while normally loaded during operation. Further, by adding these features, the force needed to translate conduit 104 over tether wire 213 may increase and may allow tether wire 213 to easily pass through distal tip 105 in only one direction. A soft distal section of distal tip 105 that is intended to engage a sloped surface on docking hub 212 as well as anchor 108 or tether wire 213 may be used by either deforming inward to create a seal or expanding outward to envelop docking hub 212 to create retention and a seal. Specifically, FIGS. 5B-5D illustrate a barbed tether wire joining with docking hub 212 and conduit 104. Burrs 503 may be cut into the distal tip of tether wire 213, for example, with an angle of 60 degrees and evenly spaced, although any suitable angle and spacing(s) may be used. Burrs 503 optionally may be permanently deformed and heat set. Docking hub 212 may suitably be advanced over burrs 503, for example in an ice bath after docking hub 212 has been expanded. The joining then may be warmed and conduit 104 may be advanced over proximal burrs 503 to lock the conduit in place.

Now referring to FIG. 6, NiTi ring 601 within the distal tip of the conduit that has dimensional overlap with tether wire 213 to couple to cryo clamped hub 602 is described. NiTi ring 601 may be exposed to a lumen within conduit 104 through which cold solution can be flushed to transition NiTi ring 601 to martensite, making translation along tether wire 213 possible during flush, and not possible when flush is stopped. NiTi ring 601 may be cold expanded directly prior to implant, then will clamp down to seal and hold position. Preferably, the transition back to austenite may be slowed thermally. This may be cold flush activatable.

Figure 5A:
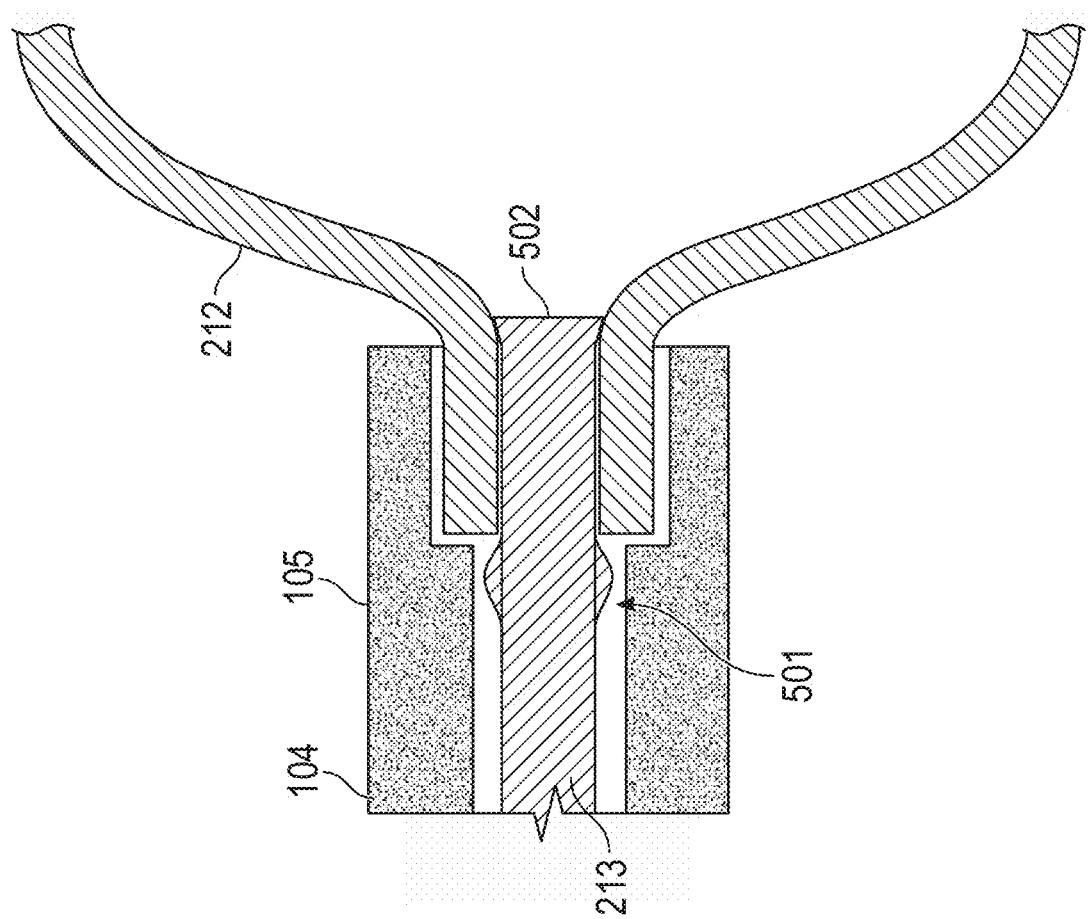
Figure 5B:
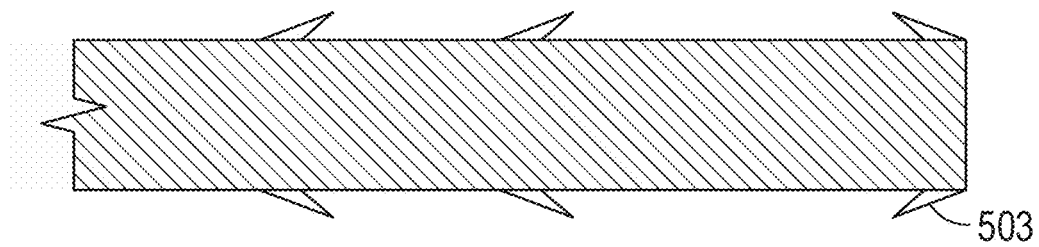
Figure 5C:
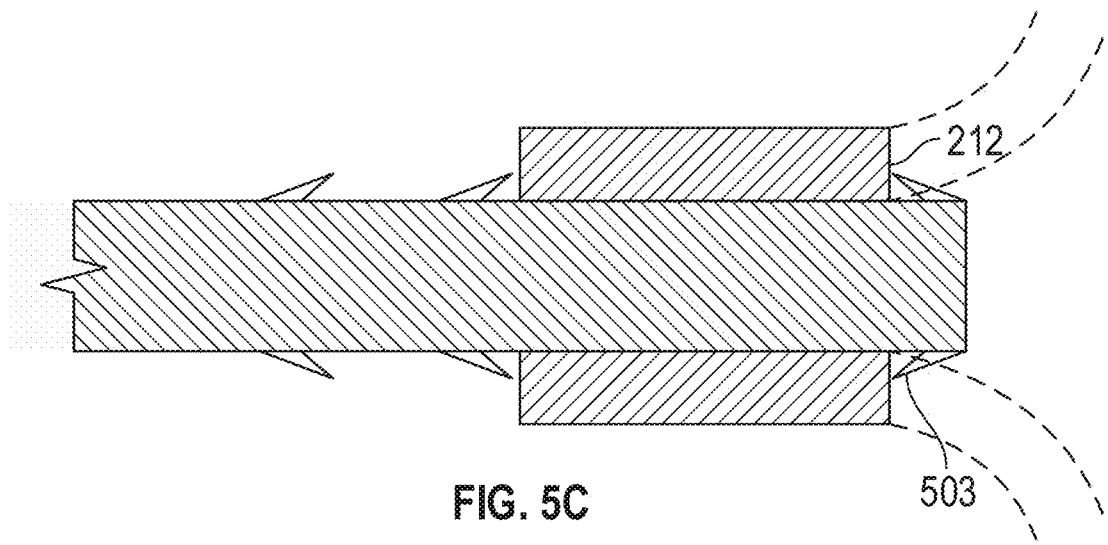
Figure 5D:
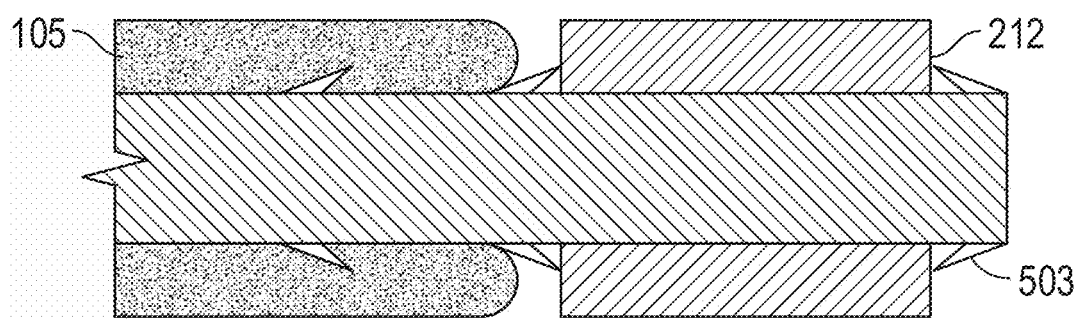

Referring now to FIG. 7A, similar to FIG. 5A, shape memory radial clamping may be used in addition to a high resistance distal feature. Resistance feature 701 of the distal tip of the conduit may have tolerances that marginally allow tether wire 213 to pass through it. Further, FIG. 7A demonstrates the deformable distal catheter section design. Soft distal section 702 of may be included to engage a sloped surface on docking hub 212, either by deforming inward when docking hub 212 is met to create a seal or expanding outward to envelope docking hub 212 to create retention and a seal. The deformed tip may retain some preload against docking hub 212 long term for a seal. FIG. 7B depicts the distal tip 105 of the conduit prior to deformation. This may also be used with radiopaque marker 222.

FIGS. 8A-8F schematically illustrate alternative exemplary structures for coupling tether wire 213 to tether wire extension 413 in accordance with the principles of the present disclosure. For example, an exchange of a balloon system, such as replacement of compliant member 102, may utilize an exchange length of tether wire (250-300 mm hub to proximal end), which may be referred herein to as a tether wire extension. It may not be desirable to store this length of wire in a subclavian space in the manner described above. Thus, an extension system may be implemented to allow a significant length of wire to be temporarily connected to a tether wire. As described with reference to FIGS. 4A-4B, a tether wire 213 and tether wire extension 413 may be coupled together using locking tube 410, such as a slide-over hypotube, that retains a joint between tether wire 213 and tether wire extension 413 to lock these elements to one another and that may be removed to disconnect these elements from one another. Other interfaces suitably may be used to detachably couple tether wire 213 and tether wire extension 413 to one another. For example, FIG. 8A illustrates a threaded interface between tether wire 213 and tether wire extension 413. FIG. 8B illustrates a matching cam profile between tether wire 213 and tether wire extension 413 locked within tube 410, similar to the design shown in FIG. 4A. FIGS. 8C-8D illustrate an interlocking pattern between tether wire 213 and tether wire extension 413 locked within tube 410. FIG. 8E illustrates a hook profile between tether wire 213 and tether wire extension 413 locked within tube 410. FIG. 8F illustrates a temporarily glued pin interface between tether wire 213 and tether wire extension 413.

Figure 9A:
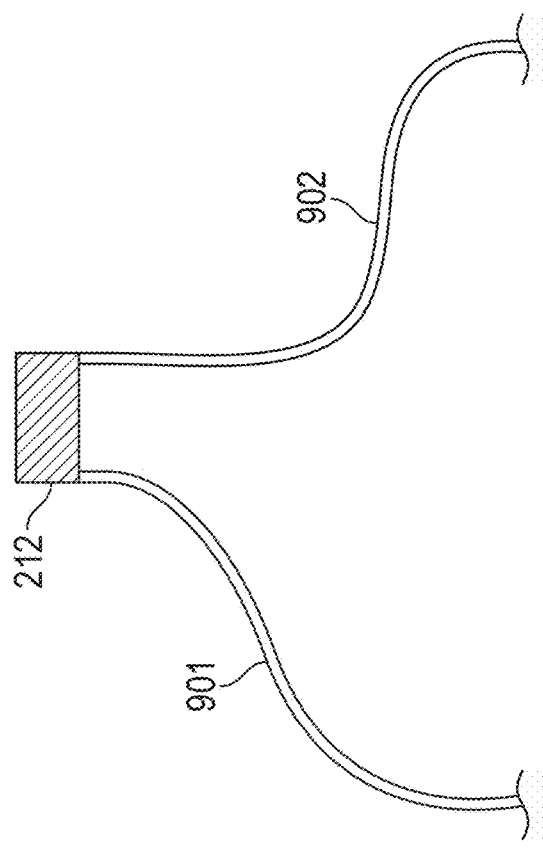
Figure 9B:
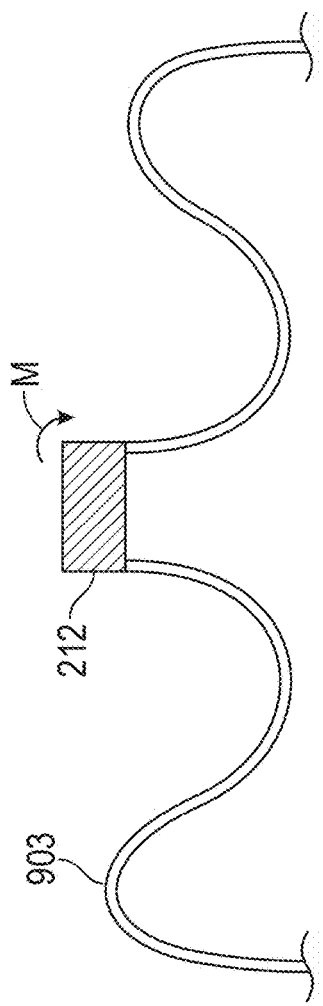

Still further configurations suitably may be implemented within the present devices. For example, FIGS. 9A-11C schematically illustrate alternative exemplary struts of the anchor 108 in accordance with the principles of the present invention. Referring now to FIGS. 9A-9B, alternative anchor strut designs are described. In FIG. 9A, multiple types of bridging struts, which respectively may be coupled to hub 212, may be included within the same anchor 108. Docking hub 212 of anchor 108 can be subjected to some complex loadings. Thus, it may make sense to explore alternate geometries in the axial struts, such as inverting every other strut. FIG. 9A illustrates normal strut 901 and inverted strut 902. If implemented within anchor 108 having six bridging struts, three of such bridging struts may be normal struts 901 and three may be inverted struts 902. This concept may be implemented with a difference height of transition from axial strut to stent section. This design has the potential to make the structure more robust to different kinds of loads, because inverted struts 902 may be stiffer in some loadings than normal struts 901. In FIG. 9B, bridging struts 903 that roll back into an "S" type profile are shown. For example, prolapsed axial struts 903 may be used. To save on axial implant length, while still providing a retrievable design, anchor 108 may include a prolapsed hub 212 and axial struts 903. This would turn the axial struts into "S" spring type struts. This design would save on implant length. However, axial forces on docking hub 212 would cause the stent structure to pull away from the wall if forces were high enough. This design would likely have greater resistance to deflections caused by moments M acting on docking hub 212 as shown. It also takes away the potential of unintentional device prolapse in vivo, as it is formed prolapsed.

Figure 10:
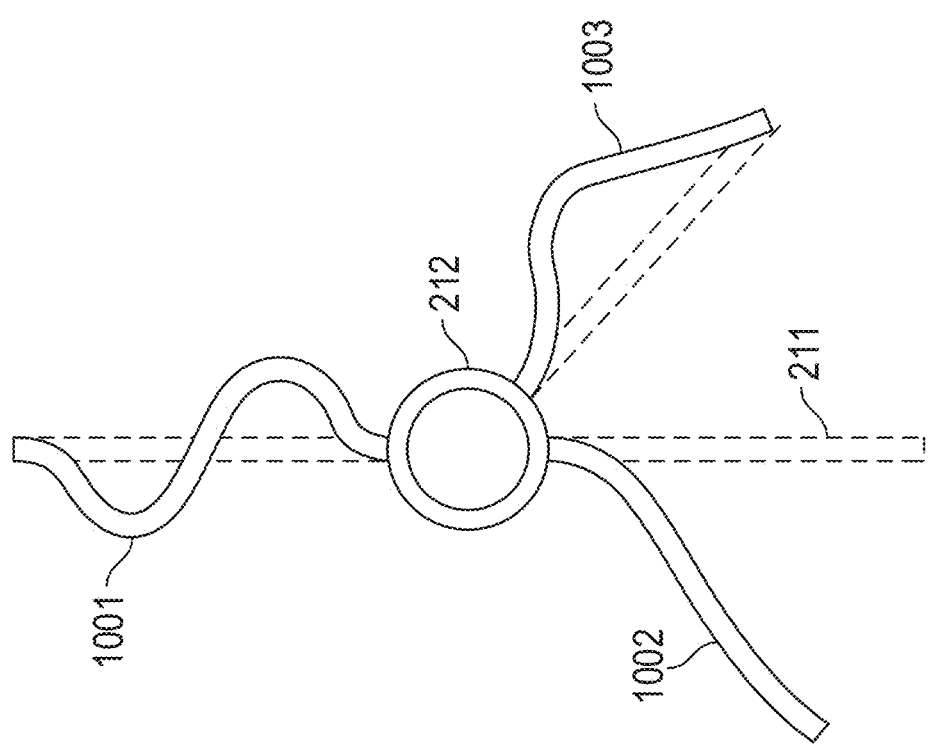

Referring now to FIG. 10-11C, additional strut variations are described. In FIG. 10, regular bridging struts 211 are shown in dashed lines for reference. Bridging struts 1001, 1002, 1003 may be formed into any suitable non-straight (curved or bent) profile when viewed axially. Bridging strut 1001 is a spring feature to isolate deformation in bridging strut 1001. Bridging strut 1002 would be clocked struts that twist docking hub 212 with relation to expandable structure 200. Would load catheter in torque to displace axially. Bridging strut 1003 is a curve-out hybrid of bridging strut 1001 and bridging strut 1002.

Reference is now made to FIG. 11A-11C. If barbs are not used with anchor 108 as described with reference to FIGS. 5A and 5B, the resistance provided by anchor 108 may in some configurations rely on friction to resist migration. Friction has three influences: friction coefficient, contact area, and normal force. To spread load over more even area or increase contact are in general, different features may be used, for instance split strut 1101 as shown in FIG. 11A, cross member 1102 as shown in FIG. 11B, and path controlled 1103 as shown in FIG. 11C. Migration resistance may be mitigated by having more geometries perpendicular to the luminal axis. These designs would still need to be retrievable. If geometries are too close to each other, it may negate advantages gained by "webbing" the tissue between struts.

Figure 12A:
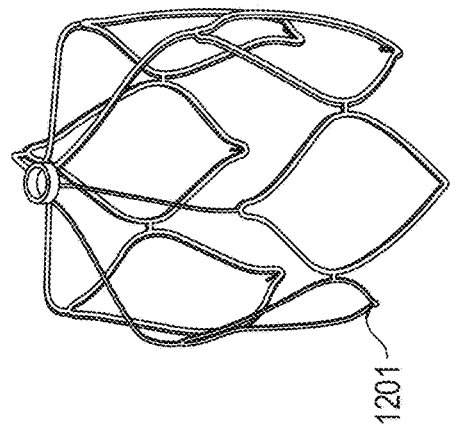
FIGS. 12A-13C schematically illustrate alternative exemplary expandable structures of the anchor in accordance with the principles of the present disclosure.
Figure 12B:
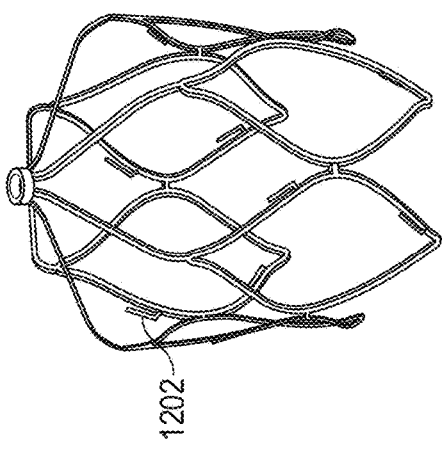
Figure 12C:
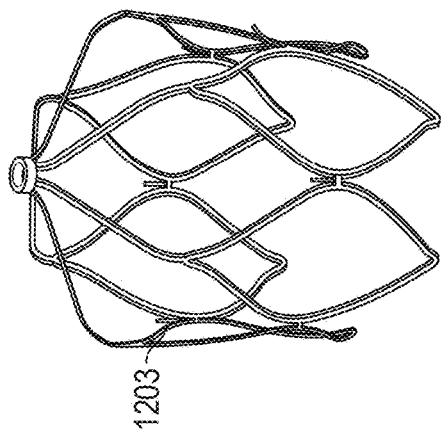
Figure 13A:
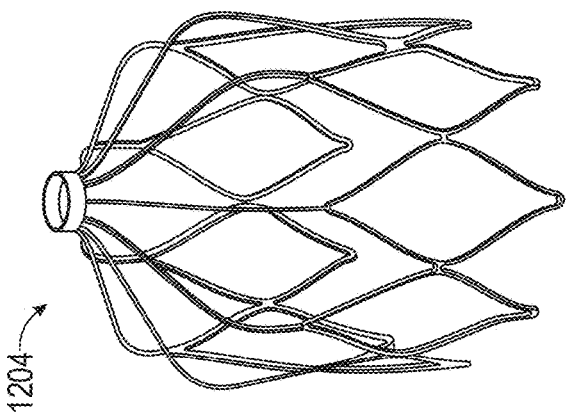
Figure 13B:
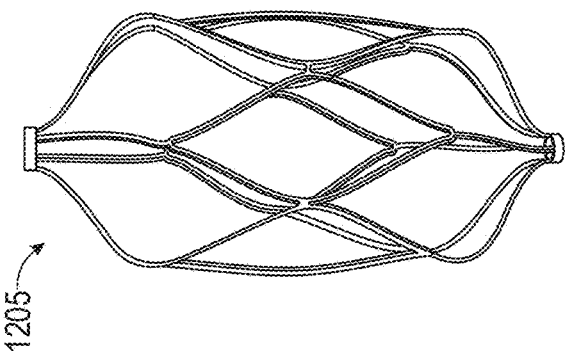
Figure 13C:
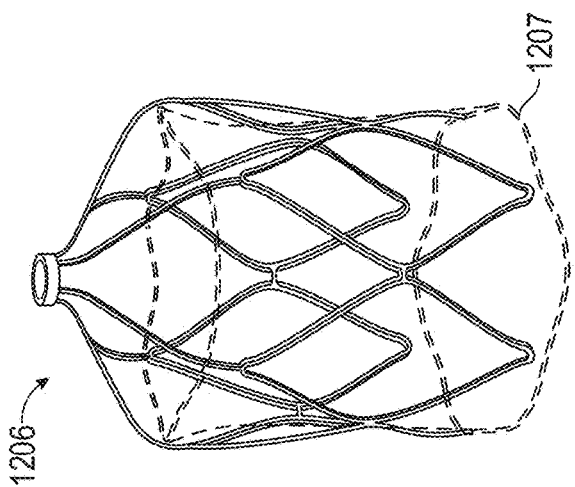

FIGS. 12A-13C illustrate alternative anchor configurations. Specifically, FIGS. 12A-12C illustrate a barbed anchor design. Barbs 1201 illustrated in FIG. 12A on the bottom apexes may increase migration resistance from the distal to proximal direction and may still be retrieved due to apex angulation. Barbs 1202 on the struts of the structural members or barbs 1203 on the connector struts may also prevent or inhibit migration of anchor 108. Expandable structure 200 of FIGS. 13A-13C may be nine-cell anchor 1204, double hub anchor 1205, and plastic encased anchor 1206, 1207. Any number of radial diamond elements in expandable structure 200 or any combination of bridging struts that emanate from the distal, proximal, or any intermediate point in expandable structure 200 may be used. Plastic or rubber coating 1207 over any suitable expandable structure in webs or around struts may be used to enhance friction. Alternatively, any number of axially stacked diamond elements in expandable structure 200 may be used. A non-symmetric radial pattern, possibly to accommodate anticipated anatomical geometries such as vessel branches may be used. The anchor may be a wound NiTi wire or stainless steel. Features may be laser cut or etched into the surface of the NiTi tube prior to laser cutting the struts to enhance the friction of the struts.

Figure 14A:
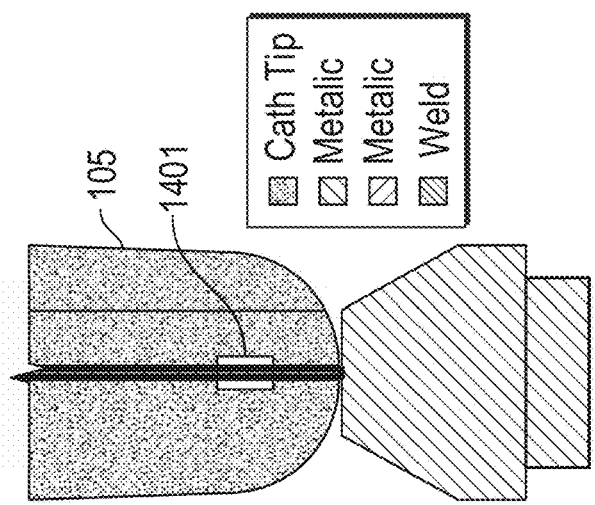
FIGS. 14A-14J schematically illustrate alternative exemplary configurations for coupling a docking hub to a conduit in accordance with the principles of the present disclosure.
Figure 14B:
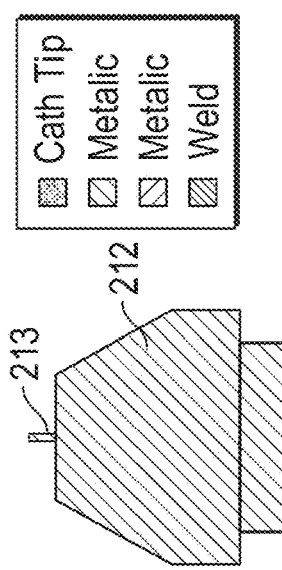
Figure 14C:
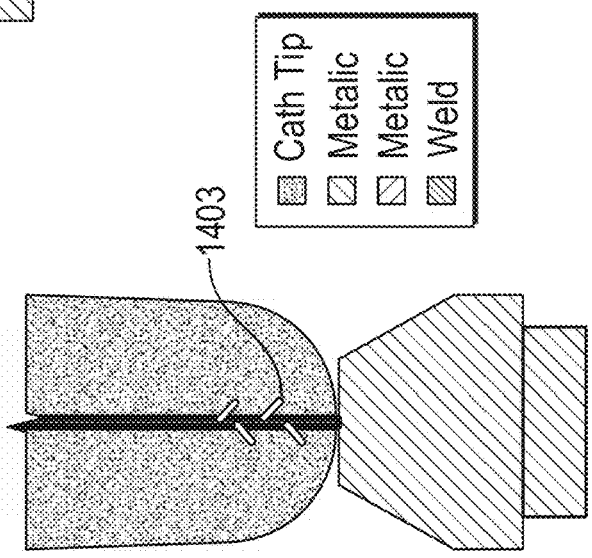
Figure 14D:
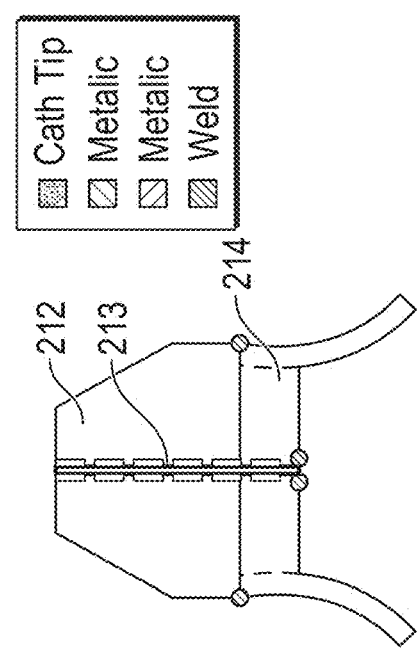
Figure 14E:
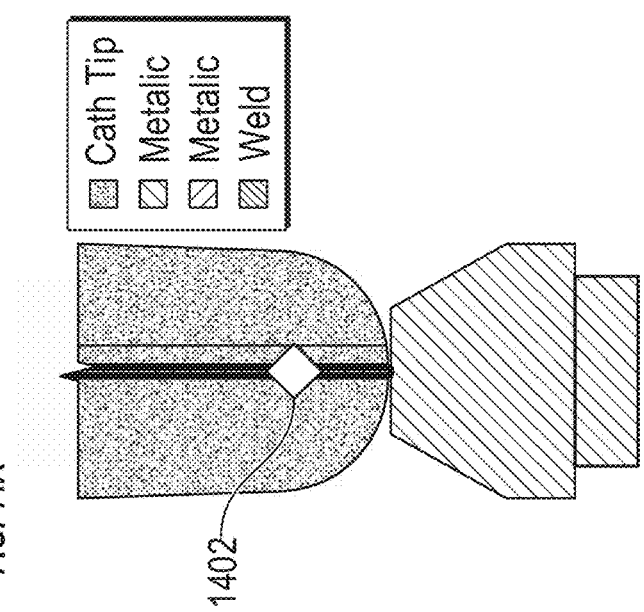
Figure 14F:
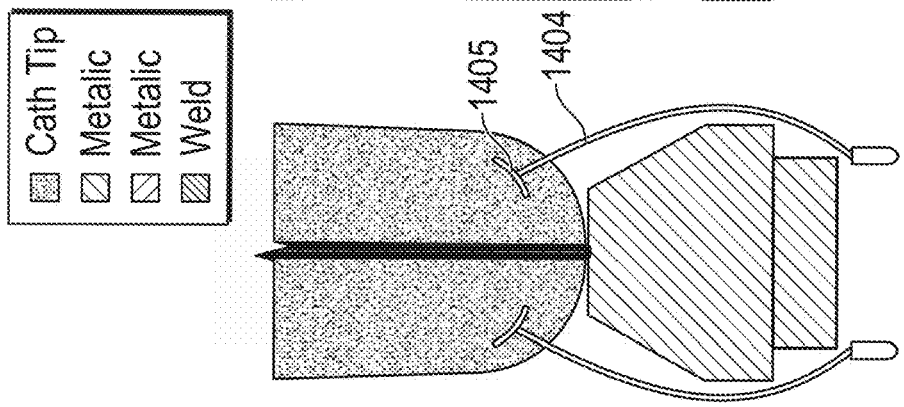
Figure 14G:
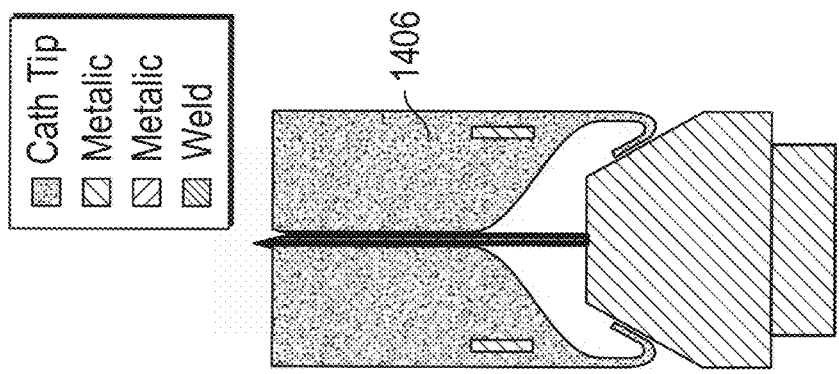
Figure 14H:
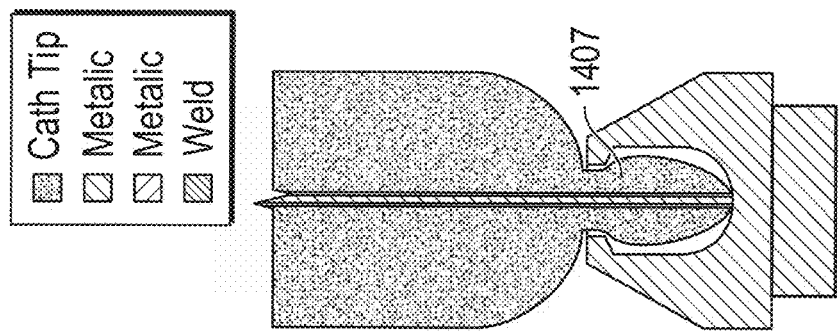
Figure 14I:
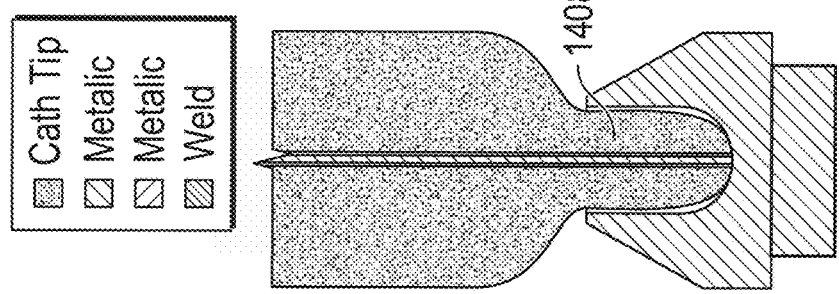
Figure 14J:
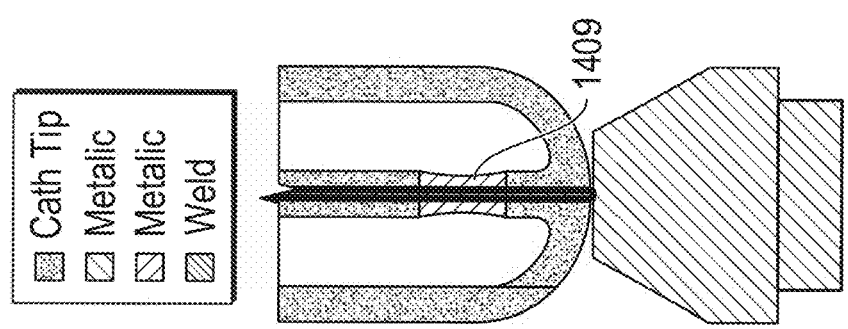

FIGS. 14A-14J schematically illustrate alternative exemplary configurations for coupling a docking hub 212 to a conduit 105 in accordance with the principles of the present disclosure. FIG. 14A illustrates a cross-sectional view of docking hub 212 welded to anchor ring 214 and to tether wire 213 in a manner such as described elsewhere herein. FIG. 14B illustrates a view of docking hub (plug) 212 and tether wire 213, with anchor ring 214 omitted. FIG. 14C illustrates an exemplary high resistance distal feature 1401, e.g., a feature within the distal tip 105 that has tolerances that marginally allow tether wire 213 to pass through it. FIG. 14D illustrates an exemplary interference distal wire feature 1402, e.g., a positive (profiled) feature on the wire (either adding material added locally to the wire or by removing adjacent material) that dramatically increases the force needed to translate the distal tip 105 over the wire. FIG. 14E illustrates exemplary barbed distal wire features 1403, e.g., directional features at the distal end of the tether wire that allow for easy passage of the wire though the catheter tip in one direction only. FIG. 14F illustrates deformable/snap over retention arms 1404, e.g., features that extend from the catheter tip that are driven radially outward when advanced over the hub 212 and recover radially inward once past the hub. Each arm 1404 optionally includes a catch 1405 to prevent or inhibit distal tip 105 from disengaging from the hub by moving proximally. FIG. 14G illustrates deformable distal catheter section 1406, e.g., a soft distal section of the catheter tip that is configured to engage a sloped surface on the docking hub 212, either deforming inward to create a seal or expanding outward to envelope the docking hub to create retention and a seal. FIG. 14H illustrates snap interference interface 1407, e.g., a cavity feature in the proximal end of the plug that has a ring that protrudes into the cavity at its proximal end. A plug with a positive bulb feature may be driven into the cavity until the bulb passes beyond the interference ring and the tip is captured within the cavity. FIG. 14I illustrates threaded interface 1408, e.g., a threaded interface at the distal tip 105. FIG. 14J illustrates a shape memory NiTi clamp, e.g., a NiTi ring within the distal tip 105 that has dimensional overlap with the tether wire. This ring may be exposed to a lumen within the conduit 104 through which cold solution can be flushed to transition the ring to martensite, making translation along the wire possible during flush, and inhibiting translation along the wire when flush is stopped.

Figure 16C:
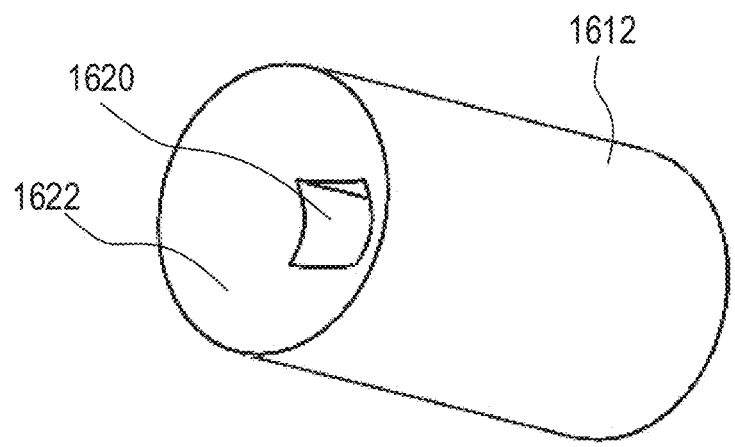

Referring now to FIGS. 16A-16E, additional alternative structures for decoupling docking hub 212 to the distal tip of conduit 104 via a screw attachment are provided. The balloon is omitted for clarity. As shown in FIGS. 16A and 16B, the distal tip of conduit 104 may include housing 1610 fixed within the lumen of conduit 104. Housing 1610 may include ridge 1628 for engaging with a corresponding groove within the proximal end of docking hub 212. Ridge 1628 may be a plurality of protrusions that fit within a plurality of grooves of docking hub 212. Alternatively, ridge 1628 may extending circumferentially about the distal end of housing 1610. At least a portion of the distal end of housing 1610 may extend beyond the distal end of conduit 104 to engage with the distal end of conduit 104, and may have an outer diameter equal to the outer diameter of conduit 104. Housing 1610 has a lumen extending therethrough sized and shaped to house screw head 1612 fixedly attached to screw 1614. Screw head 1612 may be rotated and moved axially within the lumen of housing 1610. As shown in FIG. 16C, screw head 1612 has cavity 1620 sized and shaped to receive distal end 1616 of guidewire 1602, as described in further detail below. Moreover, sloped portion 1622 of screw head 1612 may concave inward, or alternatively slope inward, to form cavity 1620. Referring again to FIGS. 16A and 16B, screw 1614 has a threaded outer surface that may removeably engage with a corresponding threaded surface within a cavity extending through the proximal end of docking hub 212. Docking hub 212 is coupled to the distal tip of conduit 104 when screw 1614 is coupled to docking hub 212.

Figure 22A:
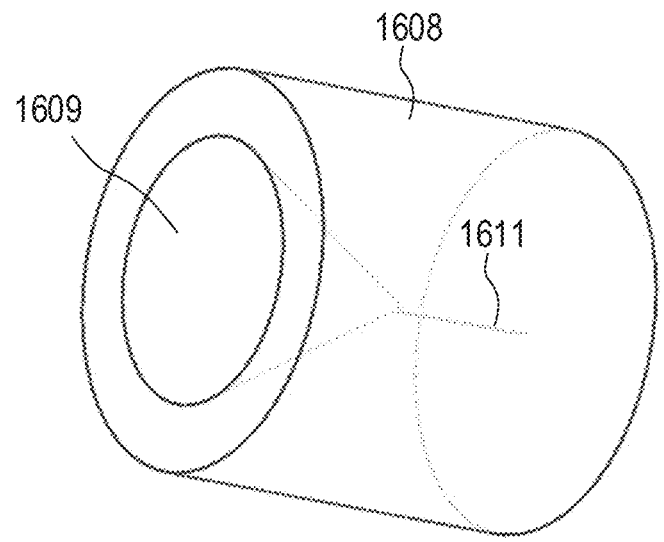
FIGS. 22A and 22B schematically illustrate an exemplary seal constructed in accordance with the principles of the present disclosure.
Figure 22B:
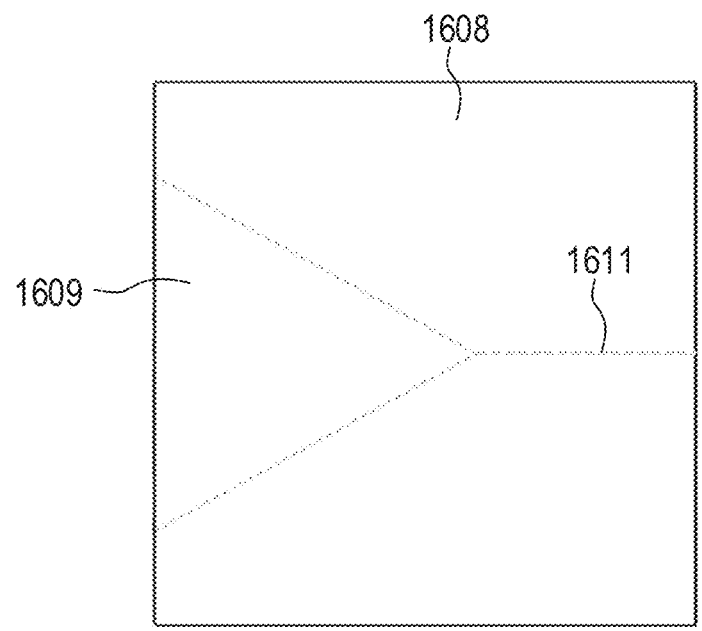

In addition, seal 1608 may be positioned within the lumen of conduit 104 proximal to housing 1610. Seal 1608 fluidicly isolates the balloon, conduit 104, and the reservoir during operation of the system as described above, e.g., from blood external to the system in contact with the distal tip of conduit 104 adjacent to docking hub 212. Seal 1608 may be formed of, e.g., silicon. As shown in FIG. 22A, seal 1608 may have a cylindrical outer surface that engages with the inner surface of the lumen of conduit 104 to form a seal. Accordingly, seal 1608 has an outer diameter equal to or greater than the diameter of the lumen of conduit 104. The proximal portion of seal 1608 may include conical cavity 1609 to guide distal end 1616 of guidewire 1602 therethrough, as described in further detail below. The distal portion of seal 1608 may include a narrow passageway 1611, e.g., formed by a thin needle, to permit distal end 1616 of guidewire 1602 to pass therethrough. When guidewire 1602 is not positioned within passageway 1611, passageway 1611 is narrow enough such that seal 1608 functions as a seal and prevents fluid from passing therethrough.

Referring again to FIGS. 16A and 16B, docking device 1606 may be fixedly positioned within the lumen of conduit 104 proximal to seal 1608. Docking device 1606 has lumen 1626 extending therethrough sized and sized to receive distal portion 1624 of pusher 1604. Lumen 1626 has a non-circular cross section such that distal portion 1624 cannot be rotated while within lumen 1626 of docking device 1606. For example, lumen 1626 may have a square or rectangular cross section, with rounded edges. Lumen 1626 may have a height and width essentially equal to the height and width of distal portion 1624 of pusher 1604, such that movement of distal portion 1624 within lumen 1626 is minimized. By preventing rotation of pusher 1604, pusher 1604 stabilizes guidewire 1602 and provides a counter-torque to the torque provided by the rotation of guidewire 1602, as described in further detail below.

Figure 16D:
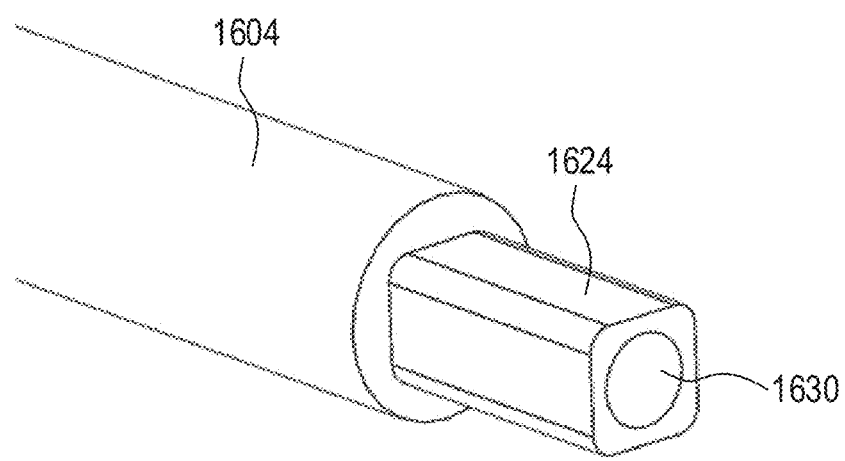

As shown in FIG. 16D, pusher 1604 includes distal portion 1624 having a geometry that corresponds with lumen 1626 as described above. Distal portion 1624 may have a square or rectangular shape, preferably with rounded edges. Distal portion 1624 and pusher 1604 may be formed as a unitary component. As shown in FIG. 16D, pusher 1604 includes lumen 1630 extending therethrough to device guidewire 1202.

Figure 16E:
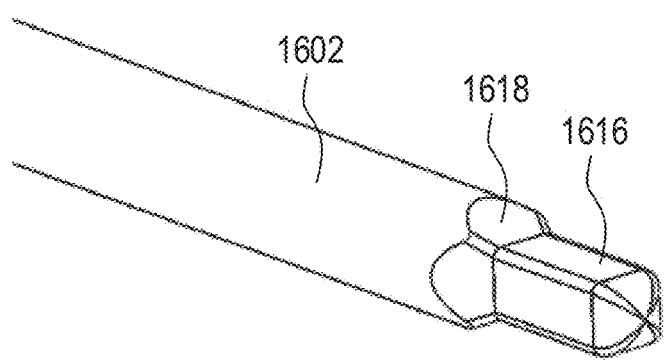

As shown in FIG. 16E, guidewire 1602 may include distal end 1616 having a geometry that corresponds with cavity 1620 of screw head 1612 as described above. Distal end 1616 may have a square or rectangular shape, preferably with rounded edges. Distal end 1616 and guidewire 1602 may be formed as a unitary component. Guidewire 1602 may include sloped portion 1618, which corresponds to the sloped portion 1622 of screw head 1612. Distal end 1616 may be actuated by rotating guidewire 1602, e.g., via the proximal end of guidewire 1602 extending out of the patient. Accordingly, when distal end 1616 is positioned within cavity 1620 of screw head 1612, and guidewire 1602 is rotated to actuate distal end 1616, the rotation of distal end 1616 causes screw head 1612 and accordingly, screw 1614 to rotate and disengage with docking hub 212 from the distal tip of conduit 104. The torque created by the rotation of guidewire 1602 is countered by pusher 1604 as described above. Thus, conduit 104 may be removed from the patient while anchor 108 remains implanted within the blood vessel.

Referring now to FIGS. 17A-17E, an exemplary method for decoupling docking hub 212 from the distal tip of conduit 104 using the structures of FIGS. 16A-16E is provided. FIG. 17A illustrates docking hub 212 coupled to the distal tip of conduit 104, e.g., during implantation of conduit 104 and anchor 108 as well as during operation of the system. Accordingly, anchor 108 and conduit 104 may be delivered to the implantation site within the blood vessel together within an introducer sheath. The introducer sheath may be retracted to deploy anchor 108 and balloon 102 (omitted for clarity) within the blood vessel, such that anchor 108 anchors balloon 102 and conduit 104 within the blood vessel.

When balloon 102 and conduit 104 need to be removed from the patient, the proximal end of conduit 104 may be decoupled from the reservoir, and pusher 1604 may be inserted through conduit 104 until distal portion 1624 engages with lumen 1626 of docking device 1606, as shown in FIG. 17B. Next, guidewire 1602 may be inserted through conduit 104, through lumen 1630 of pusher 1604, and through passageway 1611 of seal 1608, until distal end 1620 engages with cavity 1620, as shown in FIG. 17C. As shown in FIG. 17C, guidewire 1602 may be rotated to actuate distal end 1620 to thereby rotate screw head 1612 and accordingly screw 1614. When screw 1614 is completely disengaged from docking hub 212, as shown in FIG. 17D, conduit 104 may be removed from the patient, such that only anchor 108 remains implanted within the patient as shown in FIG. 17E.

Referring now to FIGS. 18A-18C, additional alternative structures for decoupling docking hub 212 to the distal tip of conduit 104 via a push mechanism are provided. The balloon is omitted for clarity. As shown in FIGS. 18A and 18B, proximal portion 1818 of docking hub 212 includes bulb 1820 extending from proximal portion 1818 via neck portion 1817. In addition, the distal tip of conduit 104 may include housing 1806 fixed within the lumen of conduit 104. Housing 1806 has cavity 1810 sized and shaped to receive proximal portion 1818 of docking hub 212.

In addition, housing 1806 includes one or more tangs 1812, which may transition between a contracted state and an expanded state upon actuation. As further shown in FIG. 18C, the distal portion of tangs 1812 includes gripping portion 1816 extending radially inward from tangs 1812, such that in the contracted state, gripping portion 1816 engages neck portion 1818 of docking hub 212. Accordingly, bulb 1820 may have an outer diameter larger than the opening provided by gripping portions 1816 of tangs 1812, and may fit within the portion of tangs 1812 between ramp 1814 and gripping portion 1816. Housing 1806 may include a plurality of tangs disposed circumferentially about the path of guidewire 1802. As shown in FIG. 18C, each tang 1812 may include ramp 1814. When the distal end of guidewire 1802 is actuated and pushed against ramp 1814, tangs 1812 transitions from the contracted state to the expanded state. Accordingly, cavity 1810 is large enough such that tangs 1812 may expand outwardly within cavity 1810 such that bulb 1820 may be released from tangs 1812 beyond gripping portion 1816.

Referring again to FIGS. 18A and 18B, seal 1608 may be positioned within the lumen of conduit 104 proximal to housing 1806. As described above, seal 1608 fluidicly isolates the balloon, conduit 104, and the reservoir during operation of the system, and includes a passageway for permitting guidewire 1802 to pass therethrough. In addition, pusher 1804 may be inserted through the lumen of catheter 1804. Pusher 1804 has lumen 1805 extending therethrough sized and shaped to receive guidewire 1802 therethrough. Lumen 1805 may have a diameter essentially equal to the outer diameter of guidewire 1802 such that pusher 1804 stabilizes guidewire 1802 within conduit 104 as the distal end of guidewire 1802 is actuated, e.g., by moving guidewire 1802 distally relative to conduit 104, to engage with ramp 1814 and transition tangs 1812 to the expanded state to thereby disengage docking hub 212 from the distal tip of conduit 104.

Figure 19D:
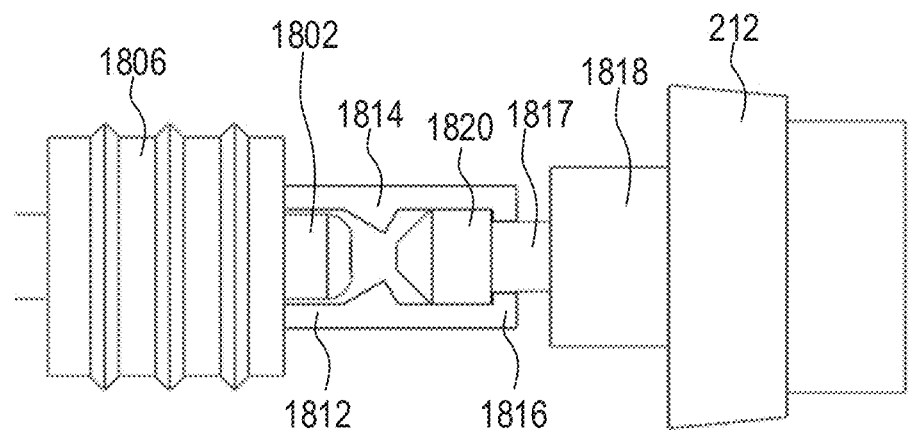

Referring to FIGS. 19A-19G, an exemplary method for decoupling docking hub 212 from the distal tip of conduit 104 using the structures of FIGS. 18A-18C is provided. FIG. 19A illustrates docking hub 212 coupled to the distal tip of conduit 104, e.g., during implantation of conduit 104 and anchor 108 as well as during operation of the system. When balloon 102 and conduit 104 need to be removed from the patient, the proximal end of conduit 104 may be decoupled from the reservoir, and pusher 1804 may be inserted through conduit 104 until the distal end of pusher 1804 rests against seal 1608, as shown in FIG. 19B. Next, guidewire 1802 may be inserted through conduit 104, through lumen 1805 of pusher 1804, through passageway 1611 of seal 1608, and through the path between tangs 1812 until the distal end of guidewire 1802 engages with ramp 1814, as shown in FIGS. 19C and 19D.

Figure 19E:
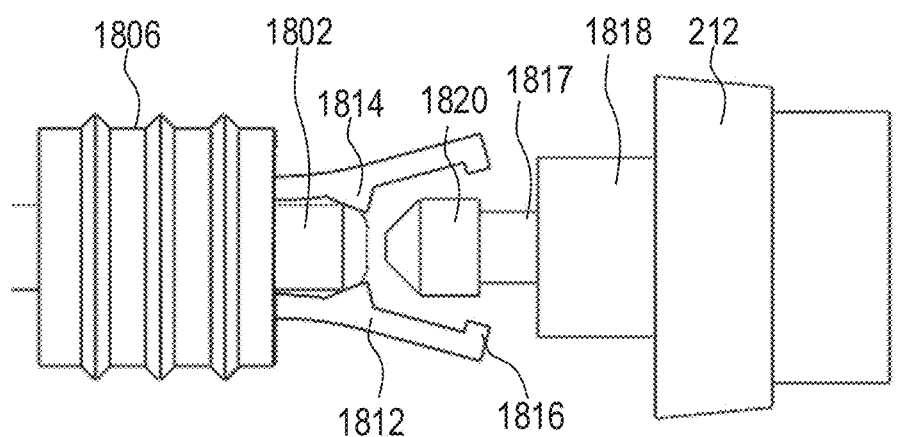

As shown in FIG. 19E, as guidewire 1802 is pushed distally against ramp 1814, tangs 1812 transition from the contracted state to the expanded state such that gripping portion 1816 disengages from neck portion 1817 of docking hub 212 to thereby release bulb 1820 from within tangs 1812. When tangs 1812 are in the expanded state, conduit 104 may be retracted proximally relative to anchor 108 to thereby disengage docking hub 212 from the distal tip of conduit 104, as shown in FIG. 19F. Accordingly, conduit 104 may be removed from the patient, such that only anchor 108 remains implanted within the patient as shown in FIG. 19G.

Figure 20A:
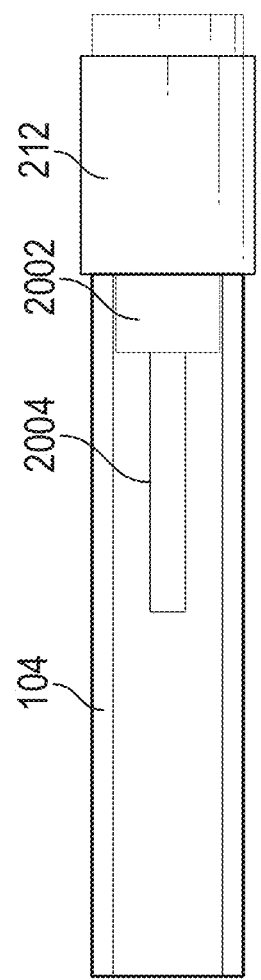
FIGS. 20A-20D schematically illustrate additional alternative structures for decoupling a docking hub from a conduit via a pull mechanism in accordance with the principles of the present disclosure.
Figure 20B:
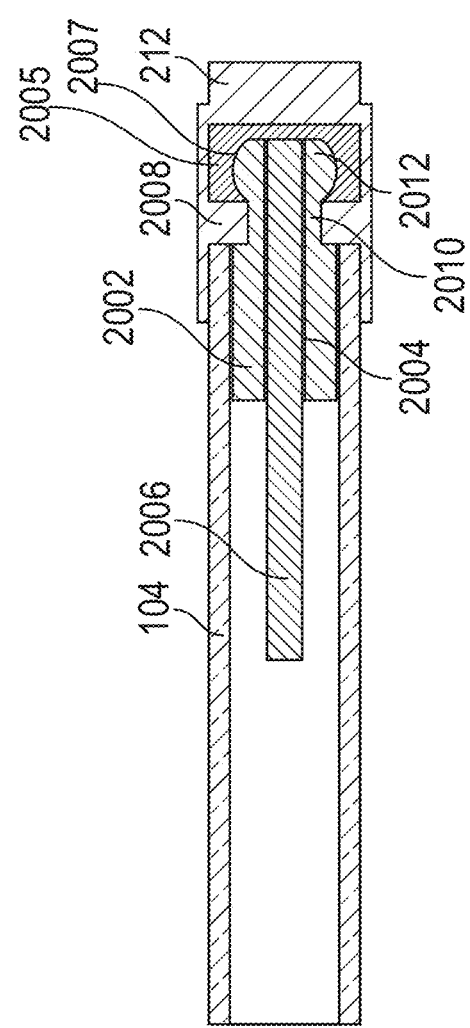

Referring now to FIGS. 20A-20D, additional alternative structures for decoupling docking hub 212 to the distal tip of conduit 104 via a pull mechanism are provided. The balloon is omitted for clarity. As shown in FIGS. 20A and 20B, docking hub 212 may include retention block 2005 for engaging with bulb portion 2012 of collapsible bulb 2002, and ridge 2008 for engaging with neck portion 2010 of collapsible bulb 2002. Block 2005 has cavity 2007 sized and shaped to receive bulb portion 2012, e.g., via a snap fit configuration. Accordingly, cavity 2007 has a geometry that corresponds with the geometry of bulb portion 2012. Ridge 2008 may be a plurality of protrusions, or alternatively, ridge 2008 may have a ring shape extending circumferentially about neck portion 2010. As shown in FIG. 20B, ridge 2008 may engage with the distal end of conduit 104.

Figure 20C:
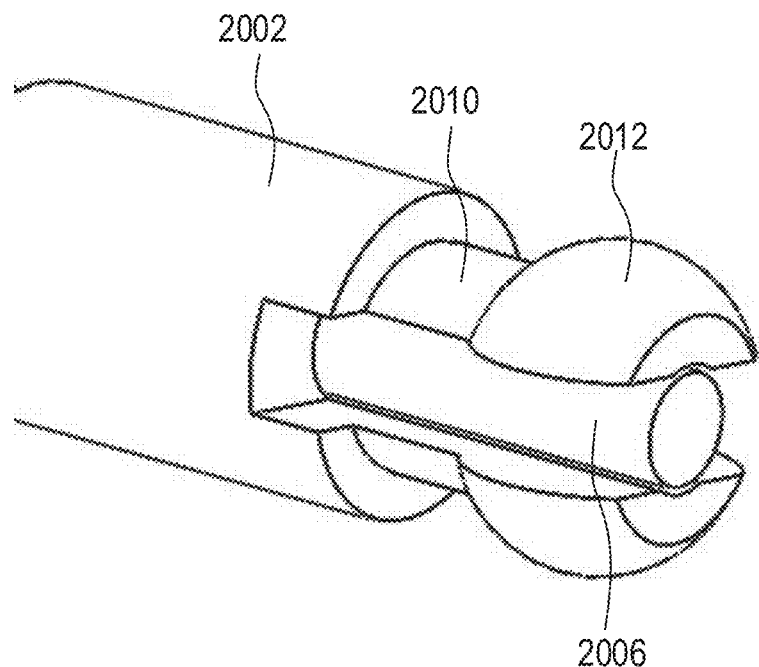

Collapsible bulb 2002 may be fixedly positioned within the lumen of conduit 104 at the distal tip of conduit 104. Collapsible bulb 2002 has neck portion 2010, bulb portion 2012, and lumen 2004 extending therethrough. Lumen 2004 is sized and shaped to receive wire 2006 therethrough. When wire 2006 is positioned within lumen 2004 of collapsible bulb 2002, e.g., during implantation of conduit 104 and anchor 108 as well as during operation of the system, as shown in FIG. 20C, bulb portion 2012 cannot be collapsed inwardly, such that ridge 2008 of docking hub 212 prevents proximal movement of collapsible bulb 2002 and collapsible bulb 2002 is engaged with docking hub 212.

Figure 20D:
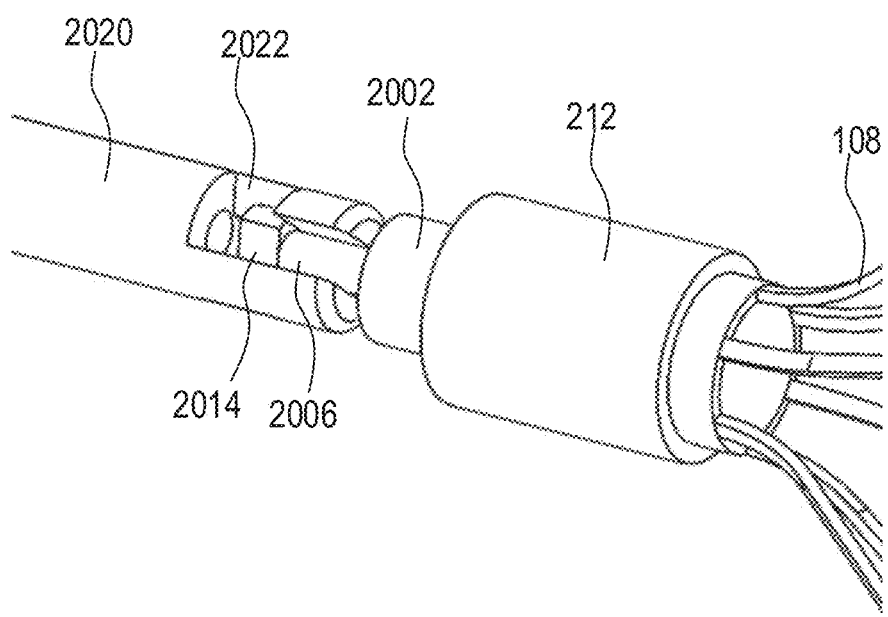

As shown in FIG. 20D, the proximal end of wire 2006 may include knob 2014. Knob 2014 may extend beyond at least a portion of the outer surface of wire 2006. In addition, guidewire 2020 is sized and shaped to be slidably movement within the lumen of conduit 104, and has a distal portion configured to engage with knob 2014 of wire 2006. For example, as shown in FIG. 20D, the distal portion of guidewire 2020 may include a groove, e.g., an L shaped groove, for receiving knob 2014. Groove 2022 may have a geometry that permits knob 2014 to be received axially therein, and locks knob 2014 within groove 2022, e.g., by rotating guidewire 2020.

Figure 21:
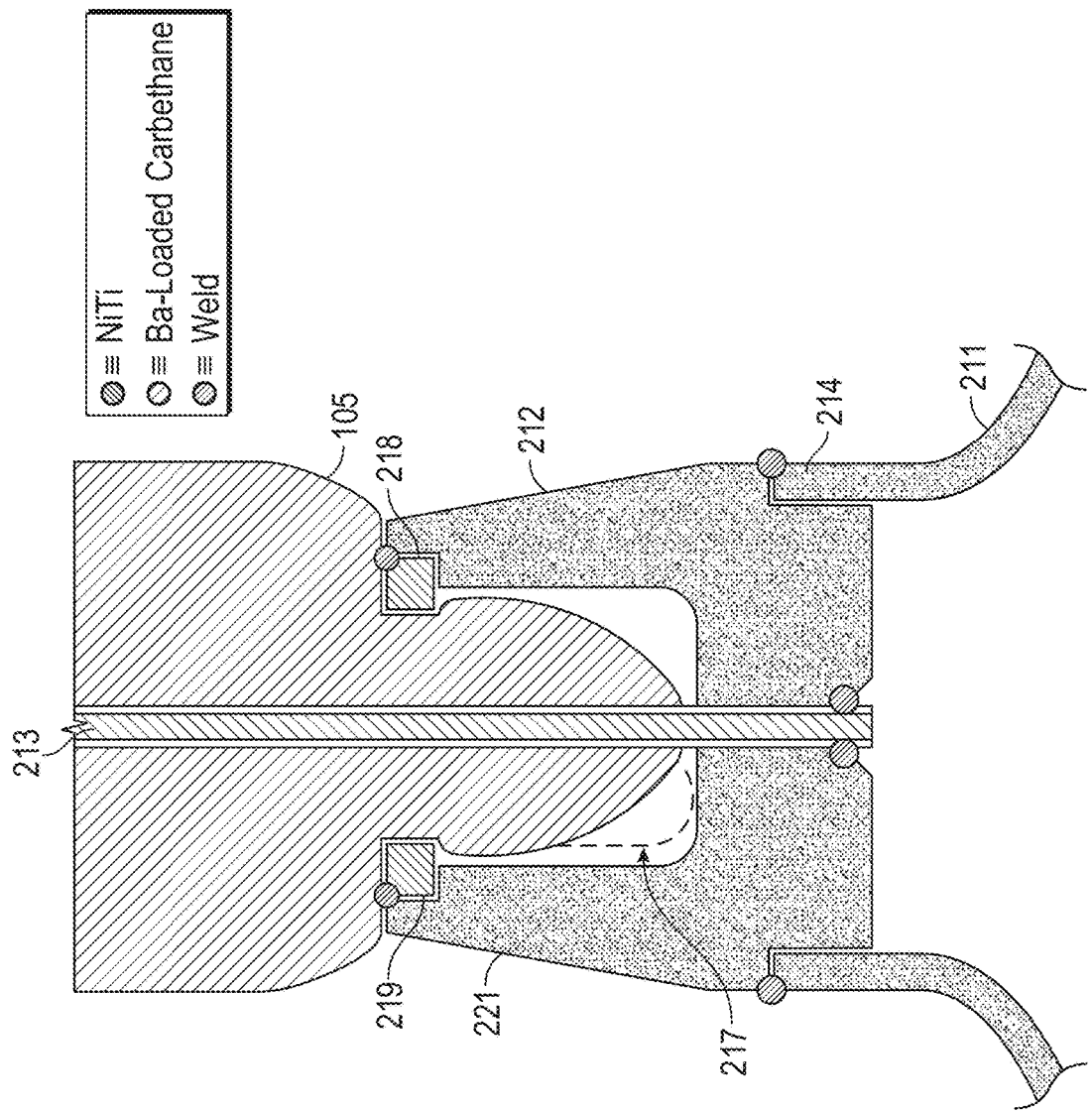
FIGS. 21A-21E schematically illustrate an exemplary method of decoupling and removing the conduit from the docking hub using the structures of FIGS. 20A-20D, in accordance with the principles of the present disclosure.

Referring to FIGS. 21A-21E, an exemplary method for decoupling docking hub 212 from the distal tip of conduit 104 using the structures of FIGS. 20A-20D is provided. FIG. 21A illustrates docking hub 212 coupled to the distal tip of conduit 104, e.g., during implantation of conduit 104 and anchor 108 as well as during operation of the system. When balloon 102 and conduit 104 need to be removed from the patient, the proximal end of conduit 104 may be decoupled from the reservoir, and guidewire 2020 may be inserted through conduit 104 until the distal portion of guidewire 2020 engages with knob 2014 of wire 2006. As described above, the distal portion of guidewire 2020 may be actuated to engage with knob 2014 by moving guidewire 2020 distally to receive knob 2014 within groove 2022, and then rotating guidewire 2020 such that knob 2014 is locked within groove 2022, as shown in FIG. 21B.

As shown in FIG. 21C, guidewire 2020 may then be retracted proximally relative to anchor 108 with a force sufficient to pull wire 2006 out from within lumen 2004 of collapsible bulb 2002. Next, as shown in FIG. 21D, conduit 104 may be retracted proximally with a force sufficient to cause ridge 2008 of docking hub 212 to push against bulb portion 2012 to cause bulb portion 2012 to collapses inward, such that collapsed bulb portion 2012 may be removed through the opening provided by ridge 2008. Accordingly, conduit 104 may be removed from the patient, such that only anchor 108 remains implanted within the patient as shown in FIG. 21E.

Figure 23A:
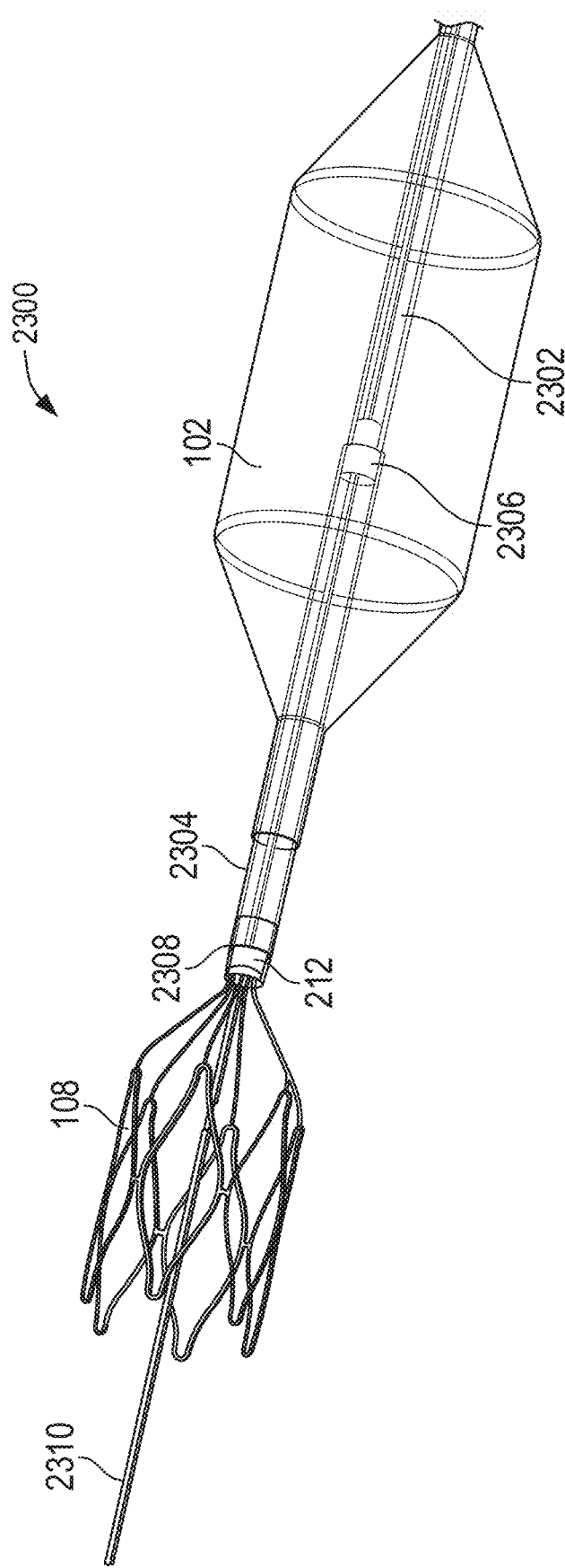
FIGS. 23A-23E schematically illustrate structures for withdrawing and deploying an anchor through a conduit in accordance with the principles of the present disclosure.

Referring now to FIGS. 23A-23E, an exemplary system for withdrawing and deploying an anchor through a conduit is provided. As shown in FIG. 23A, system 2300 may include first conduit 2302, which may be constructed similar to conduit 104 described herein, such that first conduit 2302 fluidicly couples balloon 102 and fluid reservoir 106. In addition, system 2300 further includes second conduit 2304 coupled to the distal end of first conduit 2302, and extending distally therefrom. As shown in FIG. 23A, balloon 102 may be positioned over at least a portion of second conduit 2304. Alternative, balloon 102 may be positioned over only first conduit 2302, such that second conduit 2304 is coupled to first conduit 2302 at a location distal to balloon 102. System 2300 may include seal 2306, which fluidicly isolates balloon 102, first conduit 2302, and the reservoir during operation of the system, and includes a passageway for permitting guidewire 2310 to pass therethrough.

Figure 23B:
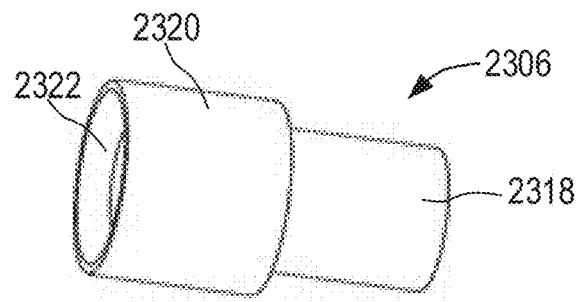

As shown in FIG. 23B, seal 2306 may include proximal portion 2318, distal portion 2320, and a seal disposed within lumen 2322 of seal 2320. The seal disposed within lumen 2322 may be constructed similar to, e.g., seal 1608 described above, to fluidicly isolate the system. Distal portion 2320 may have an outer diameter that is larger than the outer diameter of proximal portion 2318, for example, when second conduit 2304 has a larger inner diameter than first conduit 2304. Accordingly, seal 2306 may be fixed to both first conduit 2302 and second conduit 2304, e.g., seal 2306 may be reflowed in both first conduit 2302 and second conduit 2304.

Second conduit 2304 has a lumen sized and shaped to receive anchor 108 therein in a collapsed delivery state. Accordingly, the lumen of second conduit 2304 may slidably receive docking hub 212 therein, such that proximal movement of docking hub 212 within conduit 2304 causes anchor 108 to collapse into the lumen of conduit 2304, and distal movement of docking hub 212 within second conduit 2304 causes anchor 108 to be deployed within the patient's blood vessel. In addition, distal tip 2308 of second conduit 2304 has a retention feature configured to keep docking hub 212 within the lumen of second conduit 2304, and prevent docking hub 212 from moving distally beyond distal tip 2308, as described in further detail below.

Figure 23C:
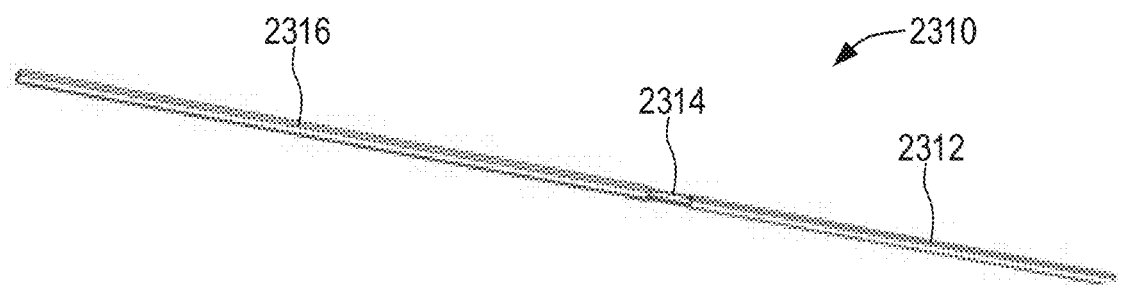

Referring again to FIG. 23A, guidewire 2310 may be used to withdraw anchor 108 into second conduit 2304, as well as to deploy anchor 108 from second conduit 2304. For example, as shown in FIG. 23C, guidewire 2310 may have proximal portion 2312, neck portion 2314, and distal portion 2316. Proximal portion 2312 may be a flattened guidewire, e.g., having one or more flat surfaces such that its cross-section is asymmetric. Similarly, distal portion 2316 also may be a flattened guidewire, e.g., having one or more flat surfaces such that its cross-section is asymmetric, such that the one or more flat surfaces of distal portion 2316 is offset, e.g., by 90 degrees, from the one or more flat surfaces of proximal portion 2312. Neck portion 2314 is narrower, or otherwise has a smaller diameter than proximal portion 2312 and distal portion 2314. Accordingly, guidewire 2310 may engage with docking hub 212 to move docking hub 212 proximally and distally within the lumen of second conduit 2304, as described in further detail below.

Figure 23D:
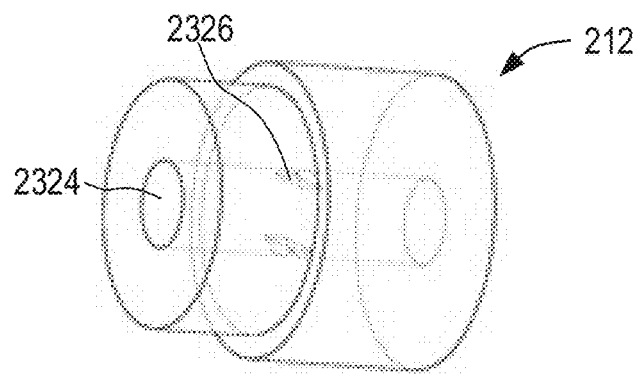
Figure 23E:
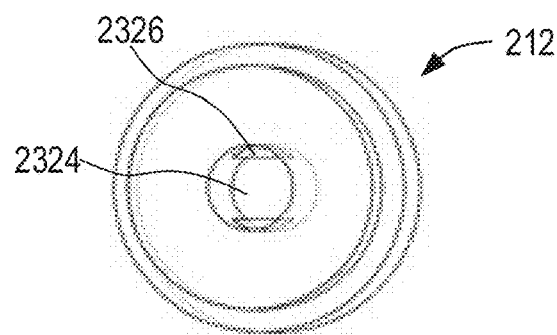

As shown in FIGS. 23D and 23E, docking hub 212 may include lumen 2324, and retention feature 2326, which narrows lumen 2324 adjacent to retention feature 2326. The shape of lumen 2324 formed by retention feature 2326 corresponds with the shape of proximal portion 2312 and distal portion 2316 of guidewire 2310. For example, in a first orientation of guidewire 2310, e.g., when the flat surfaces of distal portion 2316 extend along the upper and lower surfaces of distal portion 2316 and the flat surfaces of proximal portion 2312 extend along the lateral sides of proximal portion 2312 due to proximal portion 2312 and distal portion 2316 being offset by 90 degrees, distal portion 2316 may pass through retention feature 2326 within lumen 2324 of docking hub 212 while proximal portion 2312 cannot pass through retention feature 2326 within lumen 2324 of docking hub 212. Accordingly, guidewire 2310 may be moved distally through lumen 2324 of docking hub 212 until the distal end of proximal portion 2312 engages with retention feature 2326, such that further distal movement of guidewire 2310 causes anchor hub 212 to move distally as well.

Neck portion 2314 is positioned within retention feature 2326 when proximal portion 2312 is engaged with retention feature 2326. Accordingly, guidewire 2310 may be rotated while neck portion 2314 is within retention feature 2326 due to the smaller profile of neck portion 2314. Guidewire 2310 may be rotated to a second orientation, e.g., such that the flat surfaces of proximal portion 2312 extend along the upper and lower surfaces of proximal portion 2312 and the flat surfaces of distal portion 2316 extend along the lateral sides of distal portion 2316, while neck portion 2314 is within retention feature 2326. In the second orientation, proximal portion 2312 may pass through retention feature 2326 while distal portion 2316 cannot pass through retention feature 2326. Thus, guidewire 2310 may be moved proximally through lumen 2324 of docking hub 212 until the proximal end of distal portion 2316 engages with retention feature 2326, such that further proximal movement of guidewire 2310 causes anchor hub 212 to move proximal as well. As will be understood by a person having ordinary skill in the art, the first and second orientations need not be 90 degrees apart, and may be less or more than 90 degrees apart.

Figure 24A:
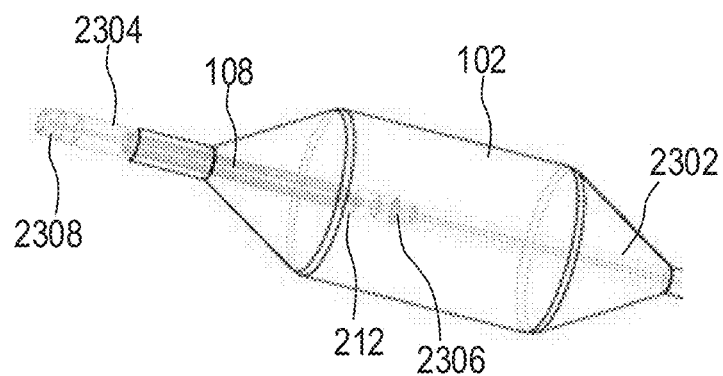
FIGS. 24A-24C schematically illustrate an exemplary method of deploying an anchor through a conduit using the structures of FIGS. 23A-23E, in accordance with the principles of the present disclosure.
Figure 24B:
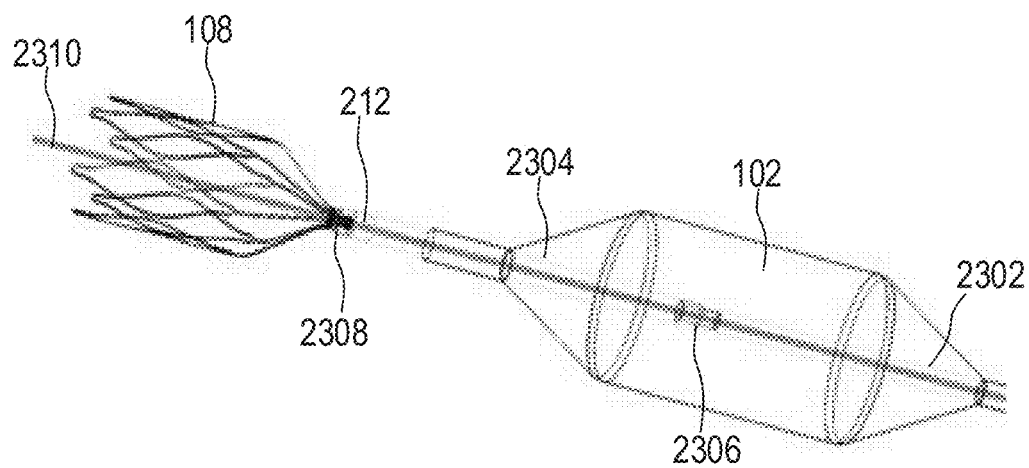
Figure 24C:
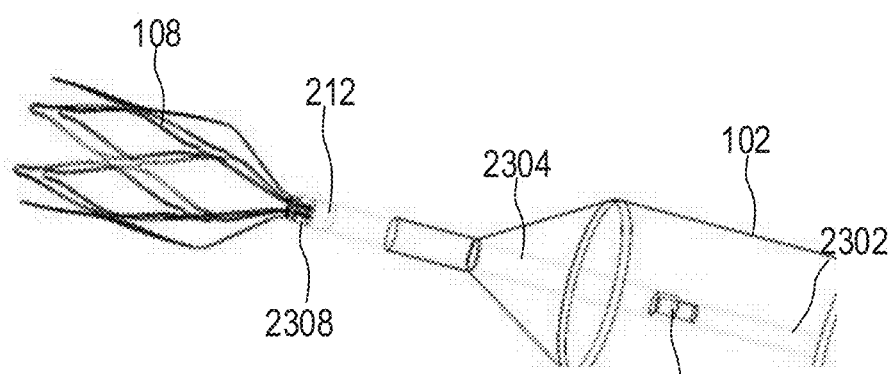

Referring now to FIGS. 24A-24C, an exemplary method of deploying anchor 108 using system 2300 of FIGS. 23A-23E is provided. As shown in FIG. 24A, anchor 108 may be delivered to the target location within the blood vessel in a collapsed delivery state within second conduit 2304. At the target location, anchor 108 may be deployed by inserting guidewire 2310 through first conduit 2302, through seal 2306, through second conduit 2304, and through docking hub 212 while distal portion 2316 of guidewire 2310 is aligned with retention feature 2326 of docking hub 212, until proximal portion 2312 engages with retention feature 2316 and causes docking hub 212 and accordingly, anchor 108 to move distally through second conduit 2304 beyond distal tip 2308 of second conduit 2308, as shown in FIG. 24B.

Should anchor 108 need to be retracted and redeployed, guidewire 2310 may be rotated to a second orientation while neck portion 2314 is within retention feature 2326 such that distal portion 2316 is not aligned with retention feature 2326, and proximal movement of guidewire 2310 causes distal portion 2316 to engage with retention feature 2326 and causes docking hub 212 and accordingly, anchor 108 to move proximal through second conduit 2304, thereby collapsing anchor 108 back into second conduit 2304. Anchor 108 may be redeployed using the steps described above. When anchor 108 is properly deployed within the patient's blood vessel, guidewire 2310 may be removed, as shown in FIG. 24C.

In some embodiments, proximal portion 2312 may have a constant shape along its entire length, e.g., from neck portion 2314 to its proximal end extending out of the patient's body. Alternatively, as shown in FIG. 25A, guidewire 2502 may include proximal portion 2506, neck portion 2508, distal portion 2510, and cylindrical portion 2502 extending proximally from proximal portion 2506. Like guidewire 2310, distal portion 2510 and proximal portion 2506 may have one or more flat surfaces offset from each other. For example, distal portion 2510 and proximal portion 2506 may both be formed from cylindrical portion 2504, e.g., a 0.035" wire. Alternatively, as shown in FIG. 25B, guidewire 2512 may include proximal portion 2516, neck portion 2518, distal portion 2520, and cylindrical portion 2514 extending proximally from proximal portion 2516, whereby distal portion 2510 and proximal portion 2506 may both be formed from, e.g., a 0.035" wire, whereas cylindrical portion 2514 has a smaller diameter, e.g., less than 0.020". As will be understood by a person having ordinary skill in the art, the proximal and/or distal portions of the guidewires described herein may have only one flat surface each, such that the shape of lumen formed by the retention feature of the docking hub permits passage therethrough upon alignment with the guidewire.

Figure 26A:
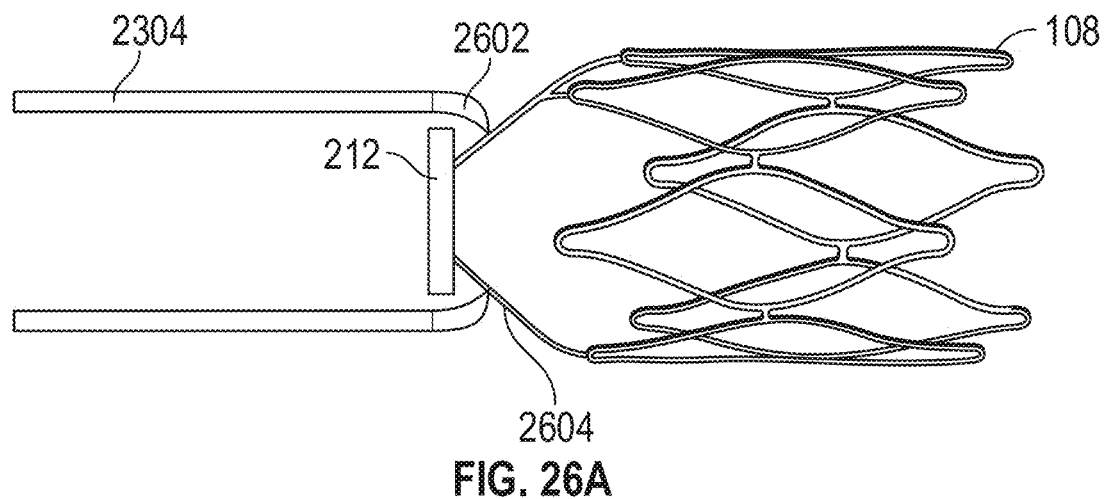
FIGS. 26A-26D schematically illustrate alternative distal tips of a conduit for retaining a docking hub within the conduit.

Referring now to FIGS. 26A-26D, alternative mechanisms to retain docking hub 212 within the conduit, e.g., conduit 2304, are provided. Some struts coupling anchor 108 to docking hub 212 are omitted for clarity. As shown in FIG. 26A, distal end 2602 of conduit 2304 may extend radially inward toward the longitudinal axis of conduit 2304, to thereby form an opening that is smaller than docking hub 212. Accordingly, while anchor 108 may be exposed beyond the opening formed by distal end 2602, distal end 2602 prevents distal movement of docking hub 212 beyond distal end 2602.

Figure 26B:
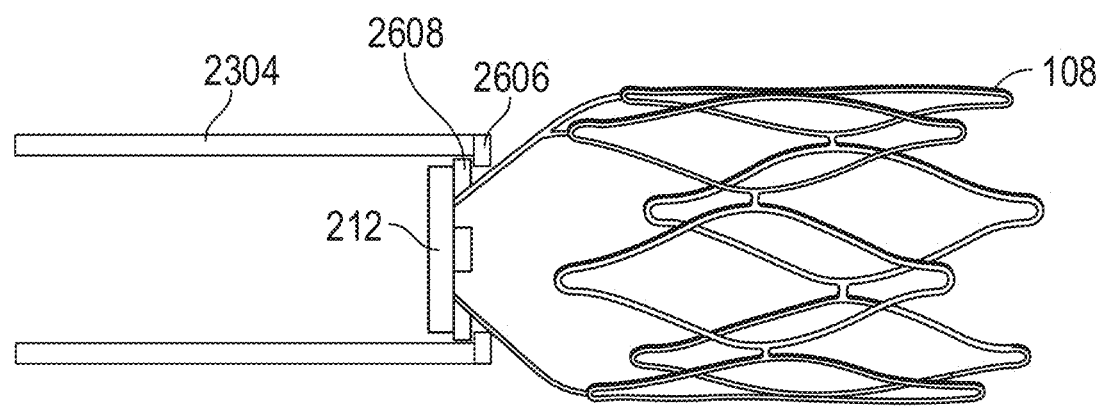

As shown in FIG. 26B, the distal end of conduit 2304 may have retention ring 2606, which narrows the opening at the end of conduit 2304. In addition, docking hub 212 may include ring 2608, which has a larger diameter than the diameter of the opening provided by retention ring 2606. Accordingly, while anchor 108 may be exposed beyond the opening formed by retention ring 2606, engagement between retention ring 2606 and ring 2608 prevents distal movement of docking hub 212 beyond retention ring 2606.

Figure 26C:
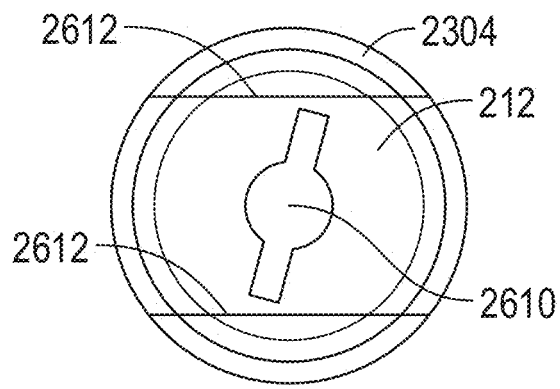

As shown in FIG. 26C, the distal tip of conduit 2304 may include one or more crossbars 2612 extending across the opening at the end of conduit 2304, such that docking hub 212 cannot move pass crossbars 2612 and are retained within the lumen of conduit 2304. Accordingly, while anchor 108 may be exposed beyond the opening of conduit 2304 across crossbars 2612, crossbars 2612 prevent distal movement of docking hub 212 beyond crossbars 2612. As shown in FIG. 26C, docking hub 212 may include a wing-shaped guidewire lumen 2610 for passing a winged-shaped guidewire therethrough. Alternatively, guidewire lumen 2610 may be have a retention feature similar to retention feature 2326 described above with regard to FIGS. 23D and 23E.

Figure 26D:
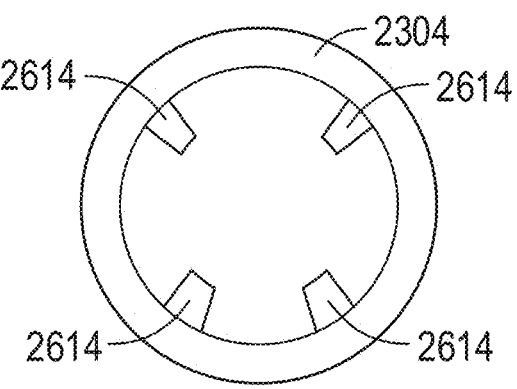

As shown in FIG. 26D, the distal end of conduit 2304 may include a plurality of retention tabs 2614, which extend radially inward toward the longitudinal axis of conduit 2304. Accordingly, while anchor 108 may be exposed beyond the opening of conduit 2304 across retention tabs 2614, retention tabs 2614 prevent distal movement of docking hub 212 beyond retention tabs 2614. In another embodiment, a retaining tether may be slidably fixed to the docking hub, such that the docking hub may slide axially along the tether wire. Thus, axial movement of the docking hub may be limited so that it cannot be deployed beyond the distal tip of the conduit. In yet another embodiment, a first part of the distal tip of the conduit may be reflowed into the conduit. Accordingly, the anchor may be loaded into the conduit in a collapsed delivery state during preparation of the conduit in the operating room. A second part of the distal tip may include any of the retention features described above, and may be snapped into the first reflowed part of the distal tip to thereby allow the anchor to be assembled into the system during implantation as opposed to during manufacturing thereof.

Figure 27C:
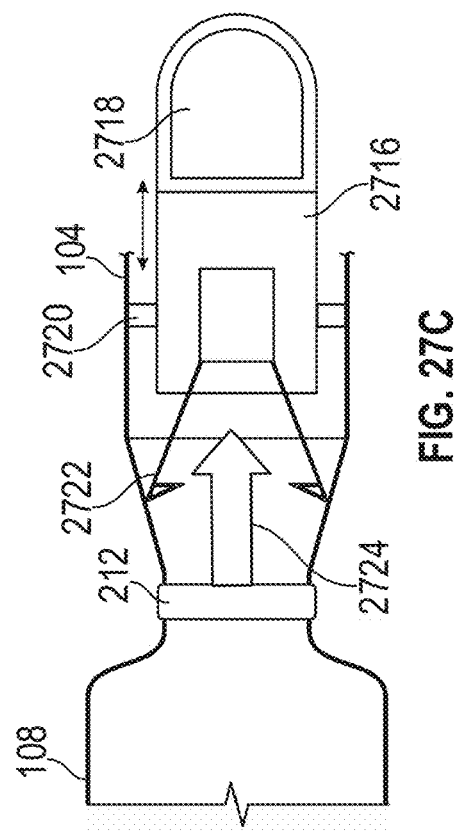
FIGS. 27A-27D schematically illustrate additional alternative structures for coupling a docking hub to a conduit in accordance with the principles of the present disclosure.
Figure 27D:
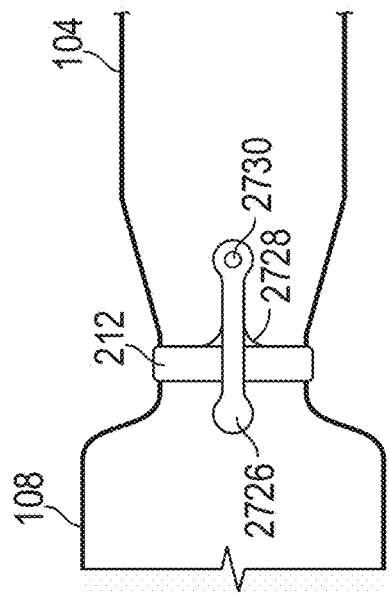
Figure 27A:
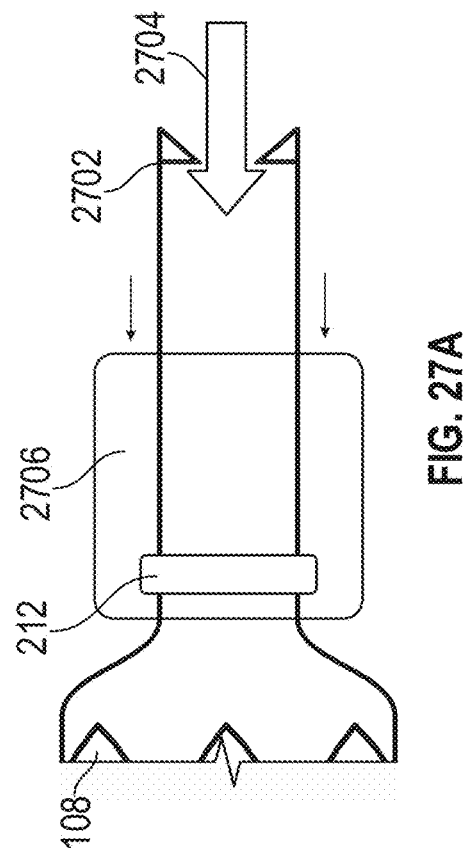

Referring now to FIGS. 27A-27D, additional alternative structures for decoupling docking hub 212 to the distal tip of conduit 104 are provided. As shown in FIG. 27A, docking hub 212 may include one or more tangs 2702 extending proximally therefrom. Tangs 2702 are transitionable between a contracted state and an expanded state, and may be biased toward the expanded state. In the contracted state, tangs 2702 may engage with arrowhead 2704 fixedly coupled to and extending distally from conduit 104, such that docking hub 212 is coupled to the distal tip of conduit 104. In addition, collar 2706 may be slidably positioned over tangs 2702 and arrowhead 2704, so as to maintain tangs 2702 in the contracted state and engaged with arrowhead 2704. When balloon 102 and conduit 104 need to be removed from the patient, a pusher device may be inserted through conduit 104 to engage with collar 2706 and push collar 2706 distally to exposed tangs 2702. Upon exposure from collar 2706, tangs 2702 transition to the expanded state, thereby releasing arrowhead 2704 such that docking hub 212 disengages with the distal tip of conduit 104. Accordingly, conduit 104 may be removed from the patient while anchor 108 remains implanted within the blood vessel.

Figure 27B:
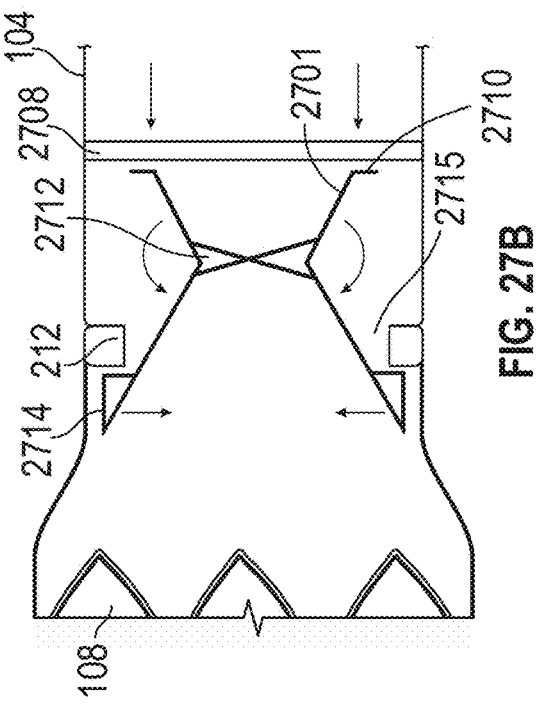

As shown in FIG. 27B, a plurality of tangs 2701 coupled to each other via scissor hinge 2712 may be fixedly coupled to the distal tip of conduit 104. Tangs 2701 are transitionable between a contracted state and an expanded state. In a first configuration, as shown in FIG. 27B, tangs 2701 are in the expanded state such that distal portion 2714 of tangs 2701 extend through lumen 2715 of docking hub 212 to engage with a distal side of docking hub 212, and proximal portion 2710 of tangs 2701 rest against seal 2708. Seal 2708 is slidably positioned within the lumen of conduit 104 proximal to tangs 2701. When balloon 102 and conduit 104 need to be removed from the patient, a pusher device may be inserted through conduit 104 to engage with seal 2708 to push seal 2708 distally to thereby engage with proximal portion 2710 of tangs 2701, which causes distal portion 2714 to contract inward to the contracted state via scissor hinge 2712 and release docking hub 212. In the contracted state, distal portion 2714 may be removed through lumen 2715 of docking hub 212. Accordingly, conduit 104 may be removed from the patient while anchor 108 remains implanted within the blood vessel.

As shown in FIG. 27C, one or more tangs 2722 may be coupled to and extend distally from the distal tip of conduit 104. Tangs 2722 are transitionable between a contracted state and an expanded state, and may be biased toward the expanded state. In the contracted state, tangs 2722 may engage with arrowhead 2724 fixedly coupled to and extending proximally from docking hub 212, such that docking hub 212 is coupled to the distal tip of conduit 104. In addition, collar 2716 may be slidably positioned over tangs 2722 and arrowhead 2724, so as to maintain tangs 2722 in the contracted state and engaged with arrowhead 2724. Collar 2716 includes eyelet 2718 sized and shaped to engage with a guidewire. For example, the distal end of the guidewire may have a hook to engage with eyelet 2718 and retract collar 2716. Moreover, seal 2720 may be positioned circumferentially between collar 2716 and the inner surface of conduit 104. When balloon 102 and conduit 104 need to be removed from the patient, the guidewire may be inserted through conduit 104 to engage with eyelet 2718 and pulled proximally to retract collar 2716 proximally relative to tangs 2722 to thereby expose tangs 2722. Upon exposure from collar 2716, tangs 2722 transitions to the expanded state, as shown in FIG. 27C, thereby releasing arrowhead 2724 such that docking hub 212 disengages with the distal tip of conduit 104. Accordingly, conduit 104 may be removed from the patient while anchor 108 remains implanted within the blood vessel.

As shown in FIG. 27D, the distal tip of conduit 104 may be coupled to docking hub 212 via bulb 2726. Bulb 2726 may be coupled to the distal tip of conduit 104 via a plurality of thin connectors 2728, and engaged with docking hub 2726 via a snap fit connection. The proximal end of bulb 2726 includes eyelet 2730 sized and shaped to engage with a guidewire. For example, the distal end of the guidewire may have a hook to engage with eyelet 2730. When balloon 102 and conduit 104 need to be removed from the patient, the guidewire may be inserted through conduit 104 to engage with eyelet 2730 and pulled proximally to cause thin connectors 2728 to break and release bulb 2726 from docking hub 212 to disengage docking hub 212 from the distal tip of conduit 104. Accordingly, conduit 104 may be removed from the patient while anchor 108 remains implanted within the blood vessel.

Figure 28:
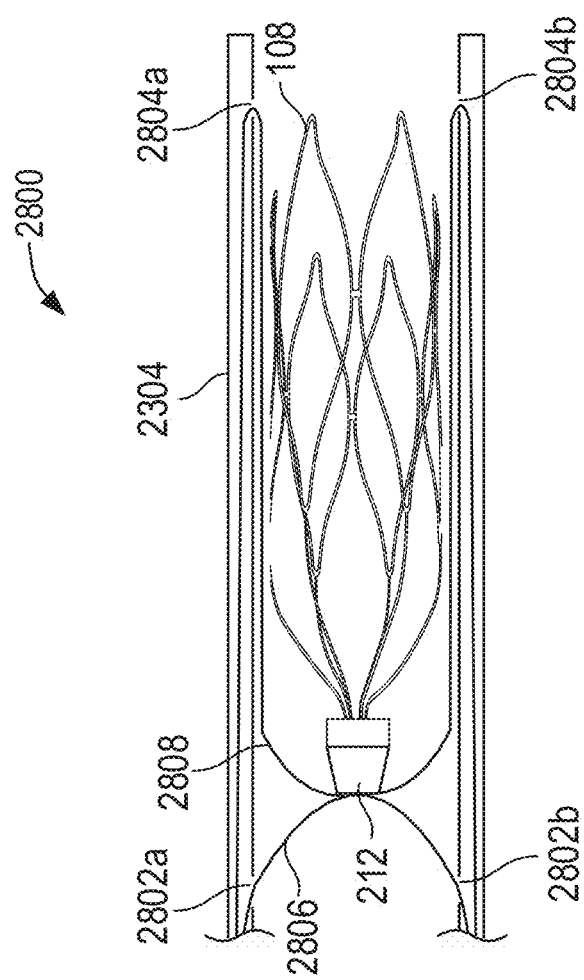
FIG. 28 schematically illustrates alternative structures for deploying an anchor through a conduit in accordance with the principles of the present disclosure.

Referring now to FIG. 28, an alternative system for deploying anchor 108 from within the conduit, e.g., conduit 2304, is provided. Conduit 2304 of system 2800 includes two or more proximal side ports 2802a, 2802b, and two or more distal side ports 2804a, 2804b. Alternatively, ports 2804a, 2804b may be positioned at the distal end of conduit 2304, as opposed to facing the lumen of conduit 2304. First wire 2806 may extend distally through the wall of conduit 2304, exit from side port 2802a, couple to docking hub 212, enter side port 2802b, and extend proximally through the wall of conduit 2304 to outside of the patient's body. In addition, second wire 2808 may extend distally through the wall of conduit 2304, exit from side port 2804a, extend proximally within the lumen of conduit 2304 to couple to docking hub 212, extend distally within the lumen of conduit 2304 to enter side port 2804b, and extend proximally through the wall of conduit 2304 to outside of the patient's body. First wire 2806 and second wire 2808 may be formed of metal or, alternatively, a polymer such as sutures.

As shown in FIG. 28, second wire 2808 is coupled to docking hub 212 at an axial location proximal to side ports 2804a, 2804b at least a length of anchor 108 in the collapsed delivery state, such that when the free ends of second wire 2808 are pulled completely proximally, anchor 104 is moved distally and exposed from the distal tip of conduit 2304. First wire 2806 and second wire 2808 may each have their own passageway through the wall of conduit 2304, or alternatively, they may share a passageway through the wall of conduit 2304.

Accordingly, anchor 108 may be delivered to the target location with the patient's blood vessel in a collapsed delivery state within conduit 2304. At the target location, one or both free ends of second wire 2808 may be pulled proximally to cause anchor 108 to move distally relative to conduit 2304, until anchor 108 is fully exposed from the distal tip of conduit 2304. Should anchor 108 need to be retracted and redeployed, one or both free ends of first wire 2806 may be pulled proximally to cause anchor 108 to be retracted back into the lumen of conduit 2304. When anchor 108 is properly deployed, one of the free ends of second wire 2808 may be released, and the other free end may be pulled to completely remove second wire 2808 from conduit 2304. Similarly, one of the free ends of first wire 2806 may be released, and the other free end may be pulled to completely remove first wire 2806 from conduit 2304. The distal tip of conduit 2304 may include any retention feature described herein to prevent docking hub 212 from moving distally beyond the distal tip of conduit 2304.

Figure 29A:
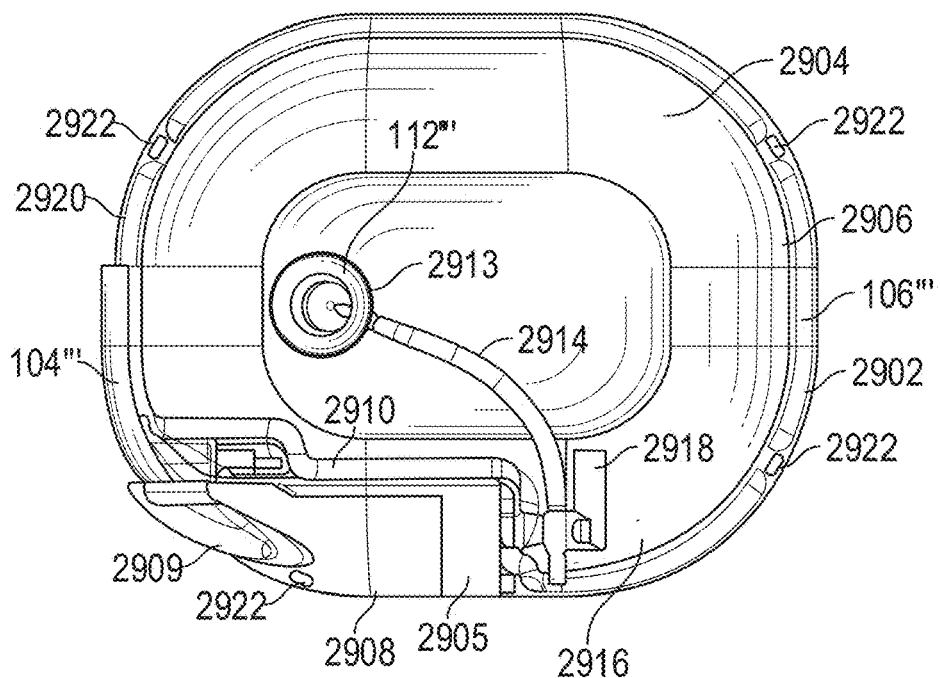
FIGS. 29A-29C illustrates an exemplary reservoir that may be used in the devices described herein.
Figure 29B:
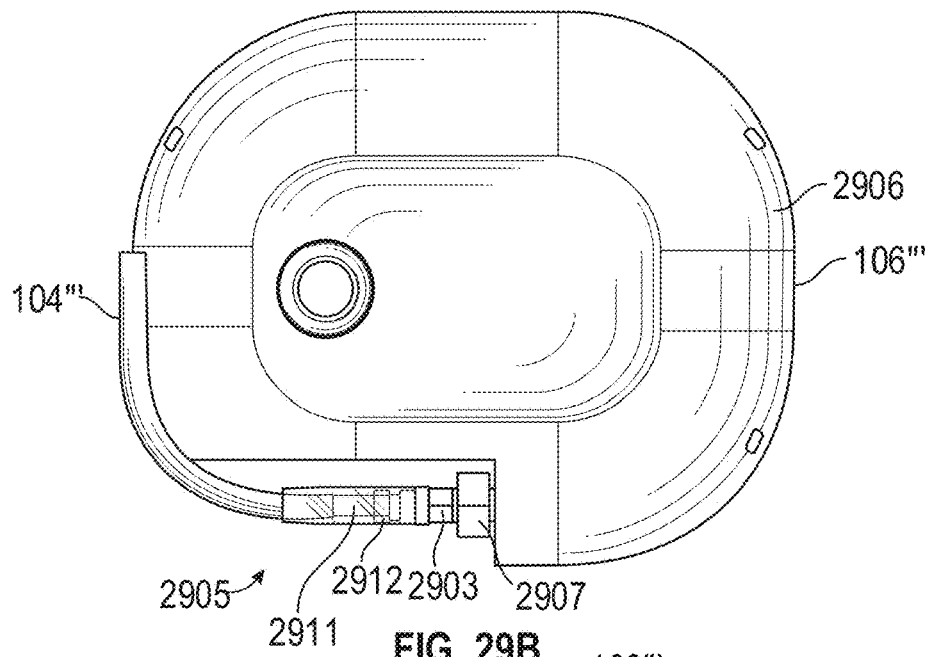
Figure 29C:
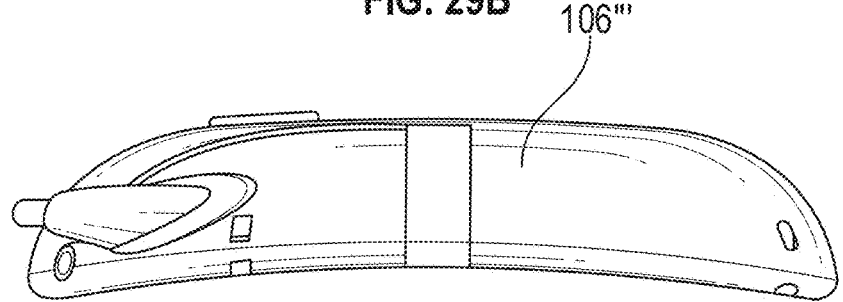

FIGS. 29A-29C illustrate exemplary reservoirs that may be used in the devices described herein. FIG. 29A shows reservoir 106''' which may be constructed in the manner as the reservoirs described above. FIG. 29A shows internal components that may be included in reservoir 106'''. Reservoir 106''' is formed from housing 2902 defining internal chamber 2904 configured to hold a fluid. The fluid, preferably a gas mixture, is designed to flow into and out of reservoir 106''' via conduit connector 2905 (best shown in FIG. 29B) responsive to pressure changes in the blood vessel where the balloon is implanted. Conduit connector 2905 permits conduit 104''' (only partially illustrated) to be releasably coupled to reservoir 106'''.

Housing 2902 may be formed from main body 2906 and removable body 2908 (or removable header) that is configured to be detached from main body 2906. Main body 2906 is fluid tight such that fluid within internal chamber 2904 only exits reservoir 106''' via conduit 104''' (or via septum 112''' when pierced). As illustrated, conduit 104''' may enter removable body 2908 at header connector 2909 that surrounds a portion of conduit 104''' to protect the portion of conduit 104''' entering reservoir 106''' and provide strain relief on conduit 104'''. Header connector 2909 may also guide conduit 104''' into the reservoir's groove described below and/or help keep the shape of reservoir 106''' to reduce pressure points. Header connector 2909 is preferably formed of a flexible/soft material such as silicone.

Reservoir 106''' also may include gasket 2910 that extends between main body 2906 and removable body 2908 to facilitate coupling between the bodies. Gasket 2910 may also help keep the shape of reservoir 106''' to reduce pressure points. In a preferred embodiment, main body 2906 and removable body 2908 are formed from a rigid material such as titanium while header connector 2909 and/or gasket 2910 are formed from a flexible material such as silicone. Header connector 2909 and gasket 2910 may be integrally formed of the same material. As illustrated, some or all of conduit connector 2905 may be disposed within removable body 2908 when attached to main body 2906.

FIG. 29B illustrates main body 2906 with removable body 2908 and header connector 2909 removed. Conduit connector 2905 may include a suitable structures to permit coupling between conduit 104''' and reservoir 106''' such as a nipple, threads, ribs, collet or the like. Illustratively, conduit connector 2905 includes inner tube 2911 within outer tube 2912. The proximal end of conduit 104''' is inserted within outer tube 2912 and over inner tube 2911. Inner tube 2911 has a lumen to provide a fluid path into main body 2906 of reservoir 106''' (e.g., into snorkel 2918 of the reservoir). Conduit connector 2905 may be removably coupled to main body 2906 of reservoir 106'''. For example, reservoir 106''' may have a threaded portion (e.g., female threads) and conduit connector 2905 may have a threaded portion (e.g., nut 2907 having male threads, or vice versa) for coupling. In addition, conduit connector 2905 includes a second, small nut 2903 that the conduit is attached to via outer tube 2912. Having conduit connector 2905 removable from main body 2906 of housing 2902 provides for better conduit coupling to the reservoir and permits suitable placement of the proximal region of the tether wire within internal chamber 2904.

Reservoir 106''' may include septum 112''' configured to be pierced to permit fluid communication within reservoir 106'''. Reservoir 106''' may include septum chamber 2913 within internal chamber 2904. Septum chamber 2913 may surround septum 112''' within internal chamber 2904 such that piercing septum 112''' provides fluid communication with septum chamber 2913. Reservoir 106''' illustratively includes internal drain tube 2914 within internal chamber 2904. Internal drain tube 2914 is coupled to septum chamber 2913 at one end and open to internal chamber 2904 at an opposing end. In this manner, liquid that may accumulate over time due to long term implantation within internal chamber 2904 may be drained via internal drain tube 2914.

The opposing end of internal drain tube 2914 may open to internal chamber 2904 at a position to facilitate liquid drainage when a patient having fluid reservoir 106''' implanted is in the seated, standing, or lying down position. The opposing end of internal drain tube 2914 may be located in internal chamber 2904 at a liquid accumulation cavity 2916 within internal chamber 2904. Liquid accumulation cavity 2916 is positioned within internal chamber 2904 to hold liquid in reservoir 106''' for ease during drainage.

Reservoir 106''' may include snorkel 2918 within internal chamber 2904. Snorkel 2918 is in fluid communication with the proximal end of conduit 104''' (e.g., via conduit connector 2905). Snorkel 2918 has an opening configured to be positioned away from liquid accumulation within internal chamber 2904 (e.g., within liquid accumulation cavity 2916). In this manner, as gas travels into and out of reservoir via snorkel 2918 into conduit 104''' responsive to pressure changes during the cardiac cycle, liquid accumulated within internal chamber 2904 is not moved, or is minimally moved, out of the reservoir along with the gas.

The outer surface of housing 2902 of reservoir 106''' may include groove 2920 configured to receive conduit 104'''. Groove 2920 may be located around a circumference of housing 2902. Groove 2920 allows conduit 104''' to be wrapped at least partially around reservoir 106''' and secured to reservoir 106'''. Reservoir 106''' may include one or more suture eyelets 2922 in housing 2902. For example, suture eyelets 2922 may be adjacent to groove 2920. Suture eyelets 2922 are designed to receive a suture to secure the conduit to the reservoir.

FIG. 29C is a side view of reservoir 106'''.

Figure 30A:
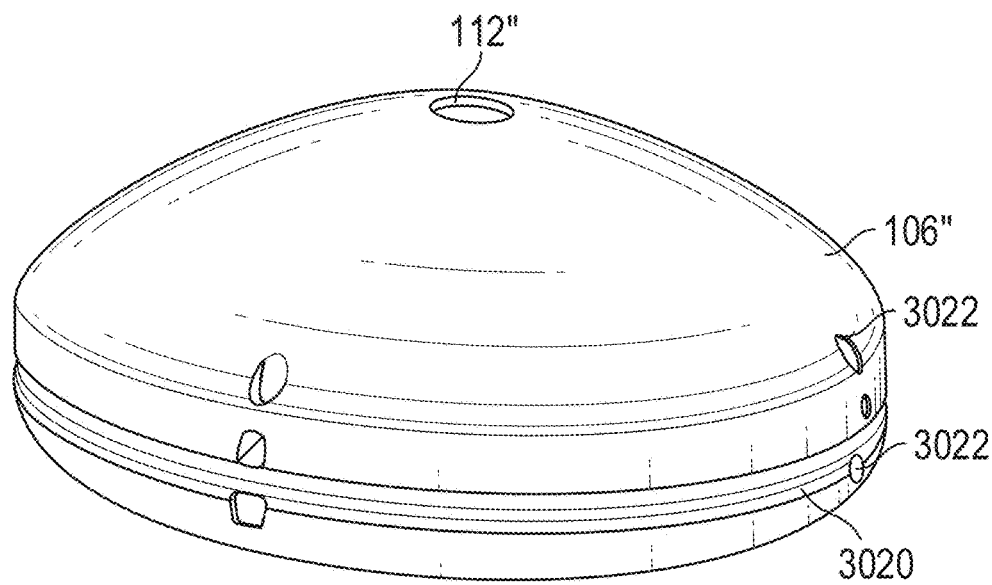
FIGS. 30A-30F illustrates an alternative exemplary reservoir that may be used in the devices described herein.

FIGS. 30A-30F illustrate reservoir 106" from FIGS. 1C and 1D that may be used in the devices described herein. Reservoir 106" is constructed similar to reservoir 106''', except that reservoir 106" has a more circular profile, with septum 112" positioned in a more central location on main body 3006. As shown in FIG. 30A, the outer surface of housing 3002 of reservoir 106" may include groove 3020 configured to receive conduit 104". Groove 3020 may be located around a circumference of housing 3002. Groove 3020 allows conduit 104" to be wrapped at least partially around reservoir 106" and secured to reservoir 106". Reservoir 106" may include one or more suture eyelets 3022 in housing 3002. For example, suture eyelets 3022 may be adjacent to groove 3020, and may straddle groove 3020. Suture eyelets 3022 are designed to receive a suture to secure the conduit to the reservoir. In this manner, a first suture eyelet 3022 may be on one side of groove 3020 and second suture eyelet 3022 may be on an opposing side of groove 3020 such that the suture travels through the first suture eyelet, around an outer surface of the conduit, and through the second suture eyelet to secure the conduit to the reservoir.

Figure 30B:
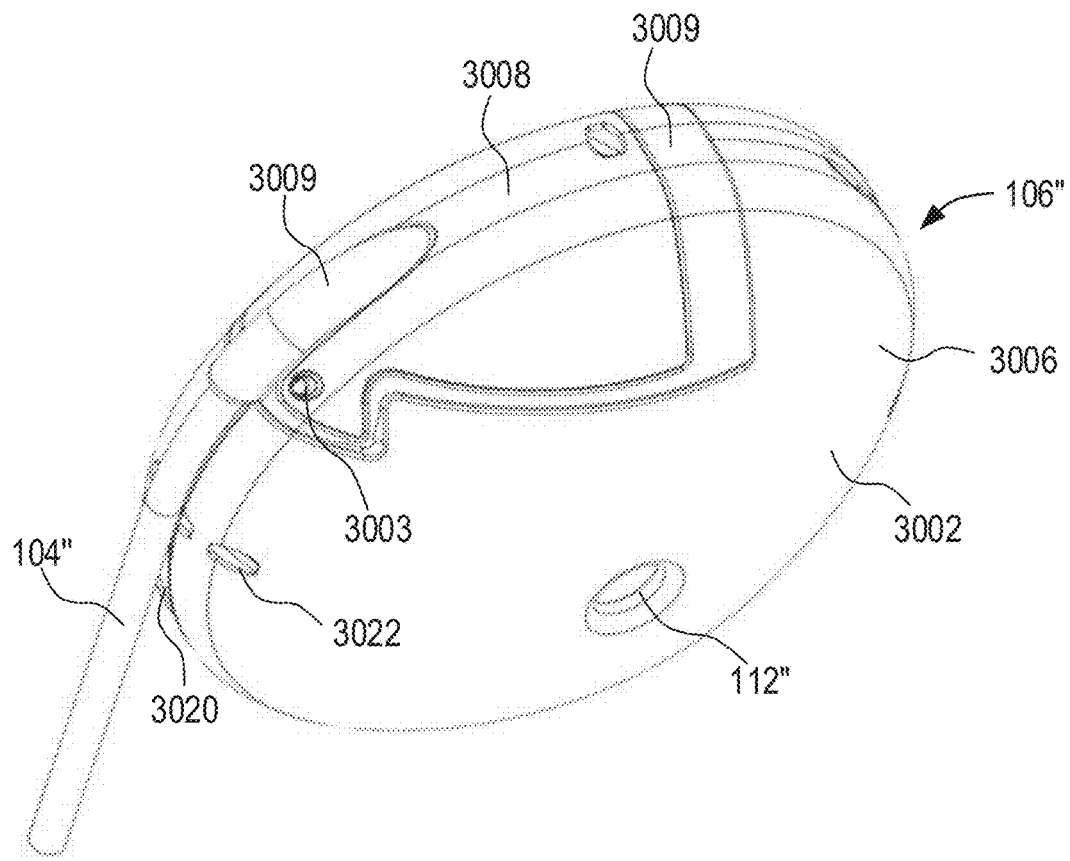
Figure 30C:
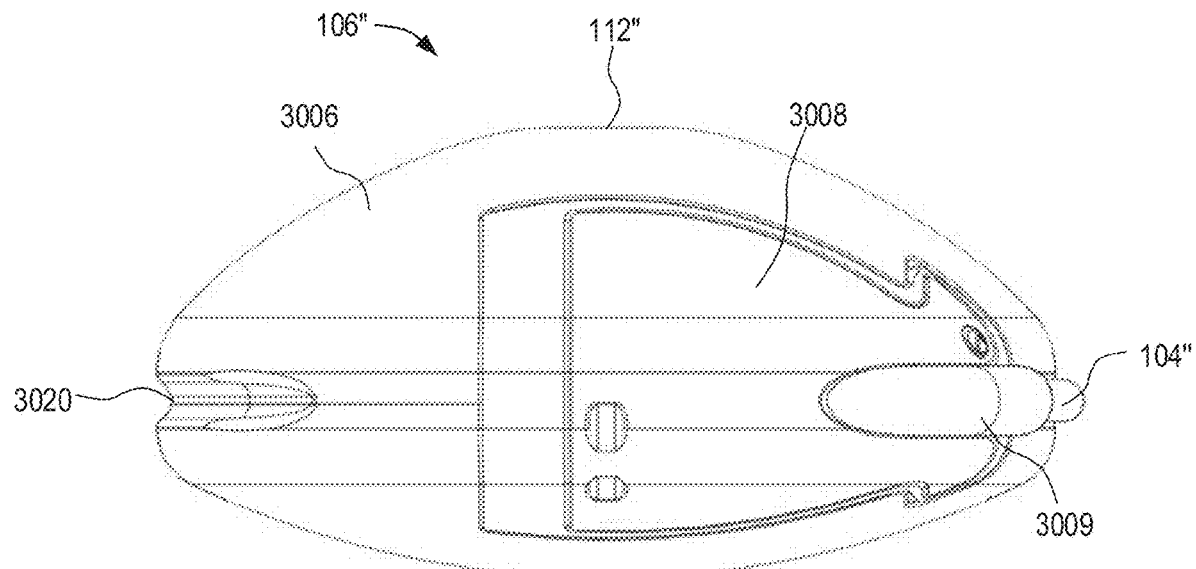

As shown in FIGS. 30B and 30C, housing 3002 may be formed from main body 3006 and removable body 3008 (or removable header) that is configured to be detached from main body 3006. Main body 3006 is fluid tight such that fluid within internal chamber 3004 only exits reservoir 106" via conduit 104" (or via septum 112" when pierced). As illustrated, conduit 104" may enter removable body 3008 at header connector 3009 that surrounds a portion of conduit 104" to protect the portion of conduit 104" entering reservoir 106" and provide strain relief on conduit 104". Header connector 3009 may also guide conduit 104" into the reservoir's groove described below and/or help keep the shape of reservoir 106" to reduce pressure points. Header connector 3009 is preferably formed of a flexible/soft material such as silicone.

Figure 30D:
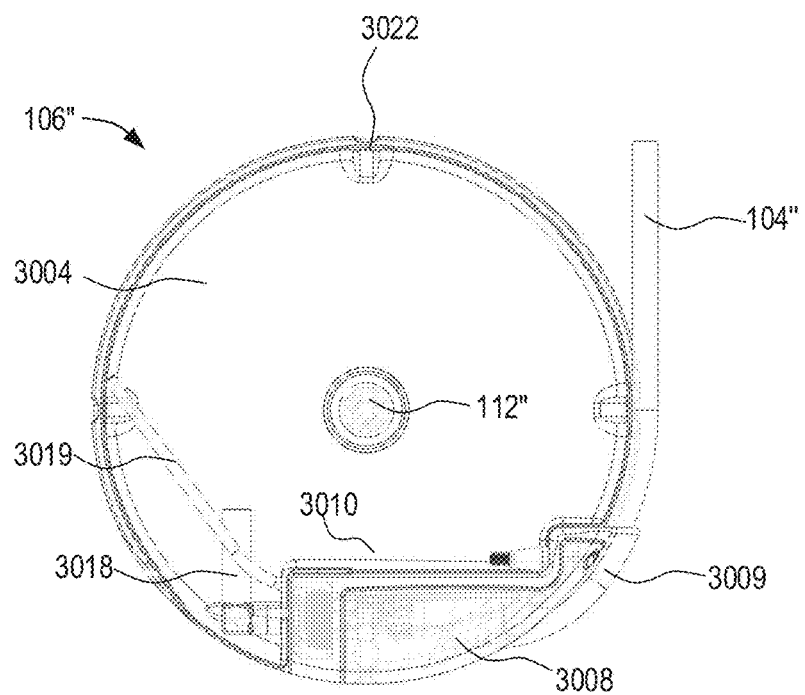
Figure 30E:
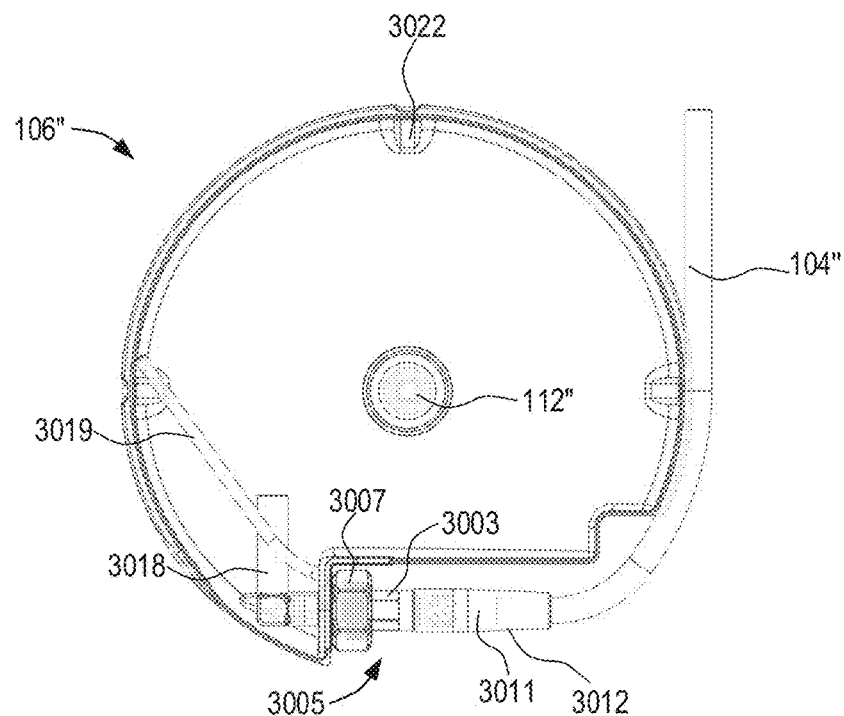

FIGS. 30D and 30E shows internal components that may be included in reservoir 106". Reservoir 106" is formed from housing 3002 defining internal chamber 3004 configured to hold a fluid. The fluid, preferably a gas mixture, is designed to flow into and out of reservoir 106" via conduit connector 3005 (best shown in FIG. 30E) responsive to pressure changes in the blood vessel where the balloon is implanted. Conduit connector 3005 permits conduit 104" (only partially illustrated) to be releasably coupled to reservoir 106". Reservoir 106" also may include gasket 3010 that extends between main body 3006 and removable body 3008 to facilitate coupling between the bodies. Gasket 3010 may also help keep the shape of reservoir 106" to reduce pressure points.

In a preferred embodiment, main body 3006 and removable body 3008 are formed from a rigid material such as titanium while header connector 3009 and/or gasket 3010 are formed from a flexible material such as silicone. Header connector 3009 and gasket 3010 may be integrally formed of the same material. As illustrated, some or all of conduit connector 3005 may be disposed within removable body 3008 when attached to main body 3006. Having conduit connector 3005 removable from main body 3006 of housing 3002 provides for better conduit coupling to the reservoir and permits suitable placement of the proximal region of the tether wire within internal chamber 3004. For example, tether wire may be disposed within tether wire channel 3019 positioned within internal chamber 3004. Preferably, one end of tether wire channel 3019 is coupled to conduit connector 3005, while the opposing end of tether channel 3019 is positioned along an outer edge of internal chamber 3004.

Figure 30F:
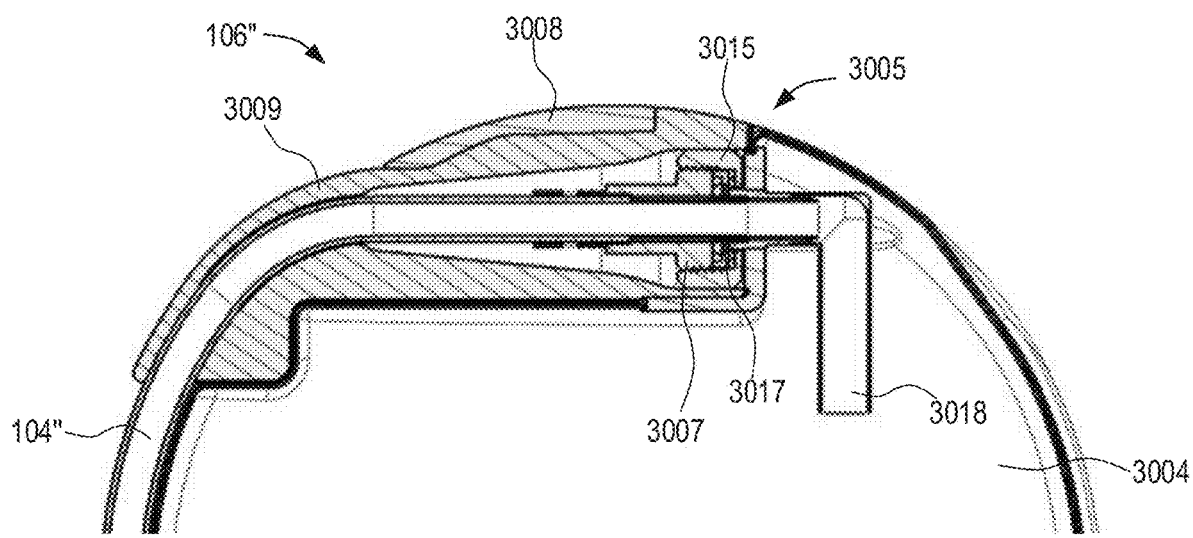

FIG. 30E illustrates main body 3006 with removable body 3008 and header connector 3009 removed. Conduit connector 3005 may include a suitable structures to permit coupling between conduit 104" and reservoir 106" such as a nipple, threads, ribs, collet or the like. Illustratively, conduit connector 3005 includes inner tube 3011 within outer tube 3012. The proximal end of conduit 104" is inserted within outer tube 3012 and over inner tube 3011. Inner tube 3011 has a lumen to provide a fluid path into main body 3006 of reservoir 106" (e.g., into snorkel 3018 of the reservoir). Conduit connector 3005 may be removably coupled to main body 3006 of reservoir 106". For example, as shown in FIG. 30F, reservoir 106" may have threaded portion 3015 (e.g., female threads) and conduit connector 3005 may have a threaded portion (e.g., nut 3007 having male threads, or vice versa) for coupling. O-ring 3017 may be positioned adjacent nut 3007 and threaded portion 3015 to form a seal. In addition, conduit connector 3005 includes a second, small nut 3003 that the conduit is attached to via outer tube 3012.

As shown in FIGS. 30A-30E, reservoir 106" may include septum 112" configured to be pierced to permit fluid communication within reservoir 106". Like reservoir 106''', reservoir 106" may include a septum chamber, internal drain tube, and liquid accumulation cavity, omitted herein for brevity.

As shown in FIG. 30F, reservoir 106" may include snorkel 3018 within internal chamber 3004. Snorkel 3018 is in fluid communication with the proximal end of conduit 104" (e.g., via conduit connector 3005). Snorkel 3018 has an opening configured to be positioned away from liquid accumulation within internal chamber 3004. In this manner, as gas travels into and out of reservoir via snorkel 3018 into conduit 104"

responsive to pressure changes during the cardiac cycle, liquid accumulated within internal chamber 3004 is not moved, or is minimally moved, out of the reservoir along with the gas.

FIGS. 31A-31F illustrate reservoir 106″″ configured to be used with the systems described in FIGS. 16A-28, which do not require a tether wire. Accordingly, reservoir 106″″ may have fewer welds, a smaller cutout for the conduit connector and header connector. In addition, reservoir 106″″ may be 3D printed, rather than machined, and thus, the header connector may be coupled to the reservoir via clip 3103, rather than a threaded screw attachment, as described in further detail below.

Figure 31A:
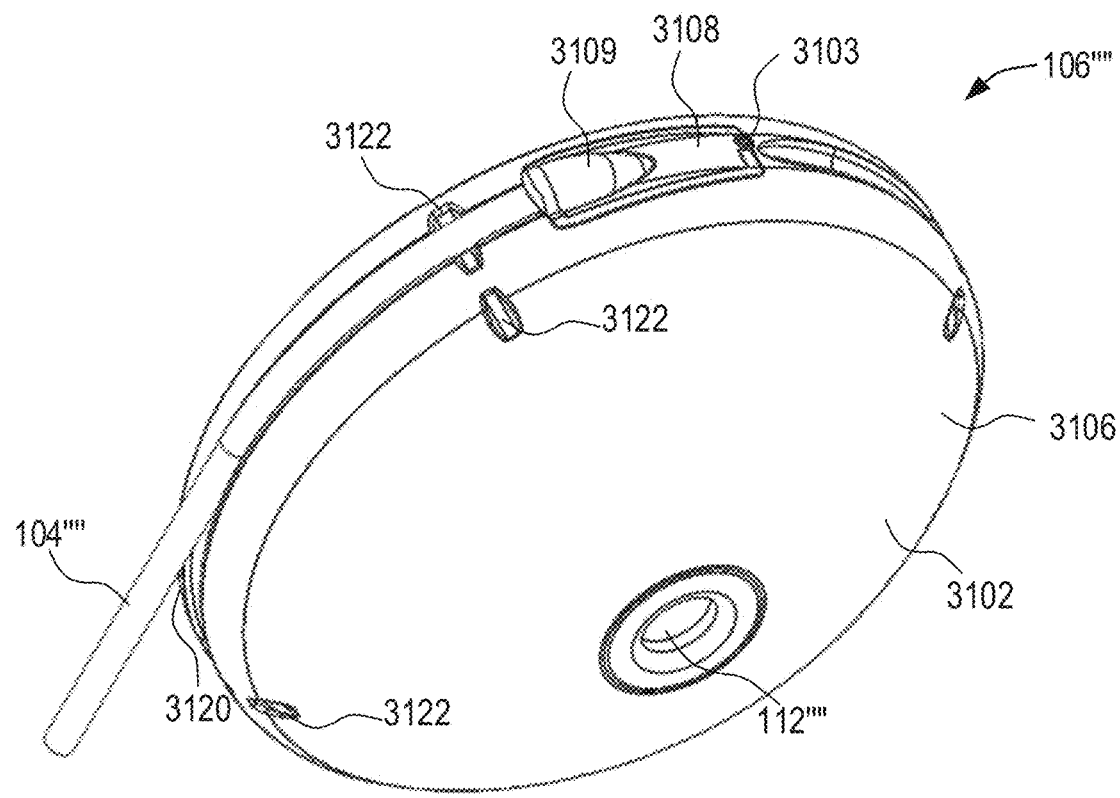
FIGS. 31A-31F illustrates another alternative exemplary reservoir that may be used in the devices described herein.

As shown in FIG. 31A, the outer surface of housing 3102 of reservoir 106″″ may include groove 3120 configured to receive conduit 104‴. Groove 3120 may be located around a circumference of housing 3102. Groove 3120 allows conduit 104″″ to be wrapped at least partially around reservoir 106″″ and secured to reservoir 106″″. Reservoir 106″″ may include one or more suture eyelets 3122 in housing 3102. For example, suture eyelets 3122 may be adjacent to groove 3120, and may straddle groove 3120. Suture eyelets 3122 are designed to receive a suture to secure the conduit to the reservoir. In this manner, a first suture eyelet 3122 may be on one side of groove 3120 and second suture eyelet 3122 may be on an opposing side of groove 3120 such that the suture travels through the first suture eyelet, around an outer surface of the conduit, and through the second suture eyelet to secure the conduit to the reservoir.

Figure 31B:
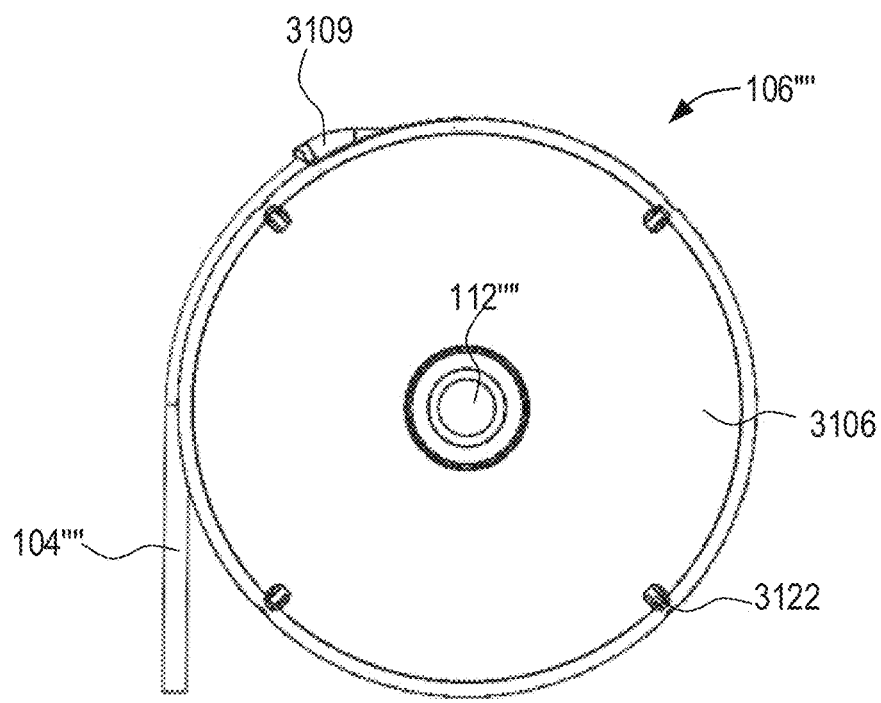
Figure 31C:
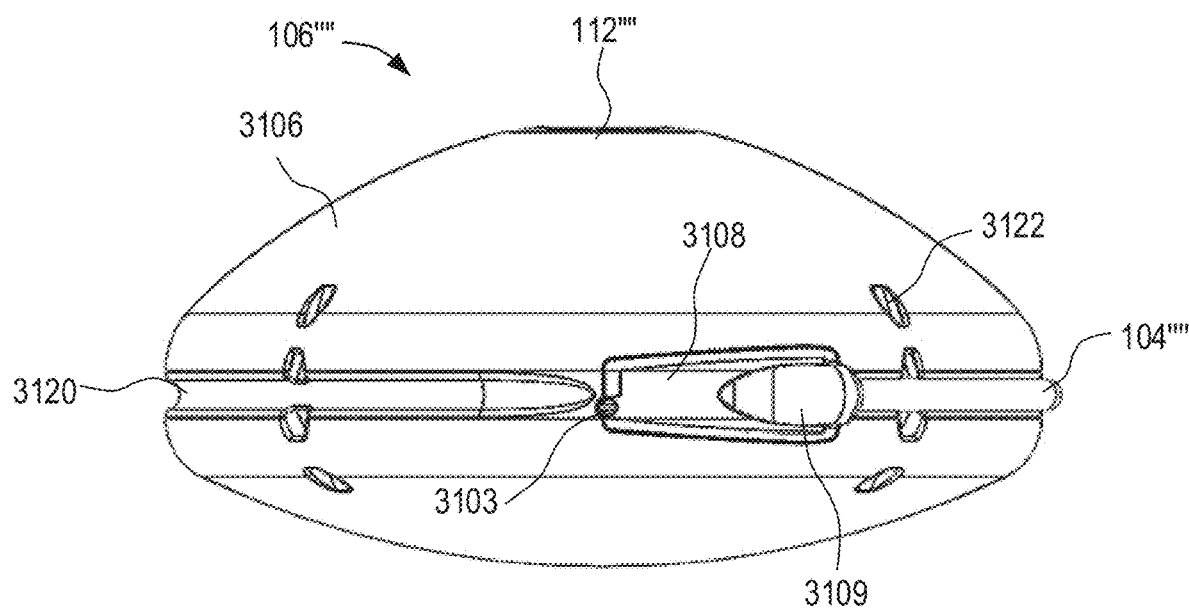

As shown in FIGS. 31A-31C, housing 3102 may be formed from main body 3106 and removable body 3108 (or removable header) that is configured to be detached from main body 3106 via clip 3103. Main body 3106 is fluid tight such that fluid within internal chamber 3104 only exits reservoir 106″″ via conduit 104″″ (or via septum 112″″ when pierced). As illustrated, conduit 104″″ may enter removable body 3108 at header connector 3109 that surrounds a portion of conduit 104″″ to protect the portion of conduit 104″″ entering reservoir 106″″ and provide strain relief on conduit 104″″. Header connector 3109 may also guide conduit 104″″ into the reservoir's groove described below and/or help keep the shape of reservoir 106″″ to reduce pressure points. Header connector 3109 is preferably formed of a flexible/soft material such as silicone.

Figure 31D:
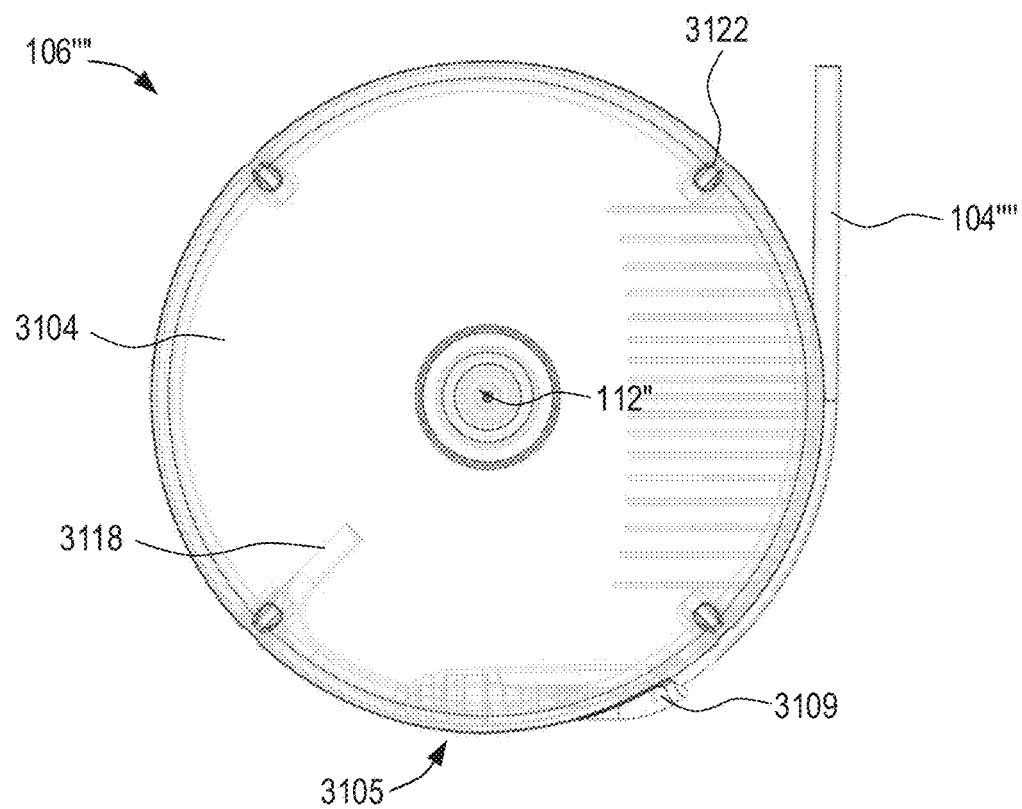
Figure 31E:
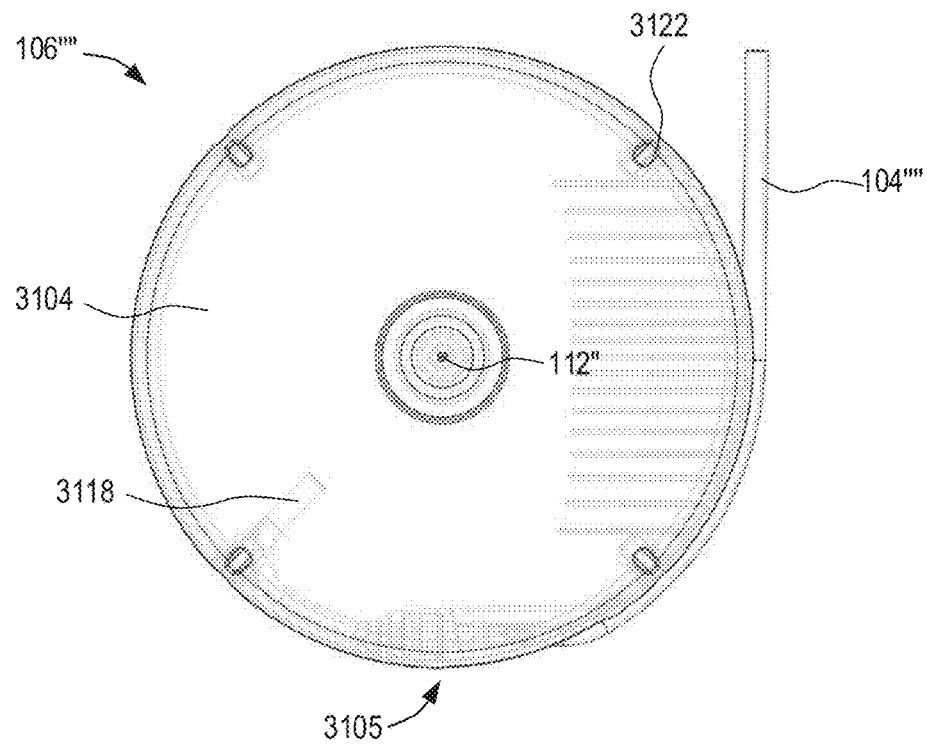

FIGS. 31D and 31E shows internal components that may be included in reservoir 106″″. Reservoir 106″″ is formed from housing 3102 defining internal chamber 3104 configured to hold a fluid. The fluid, preferably a gas mixture, is designed to flow into and out of reservoir 106″″ via conduit connector 3105 (best shown in FIG. 31F) responsive to pressure changes in the blood vessel where the balloon is implanted. Conduit connector 3105 permits conduit 104″″ (only partially illustrated) to be releasably coupled to reservoir 106″″. Like reservoir 106′, reservoir 106″″ may include a gasket, omitted herein for brevity.

In a preferred embodiment, main body 3106 and removable body 3108 are formed from a rigid material such as titanium while header connector 3109 may be formed from a flexible material such as silicone. As illustrated, some or all of conduit connector 3105 may be disposed within removable body 3108 when attached to main body 3106. Having conduit connector 3105 removable from main body 3106 of housing 3002 provides for better conduit coupling to the reservoir.

Figure 31F:
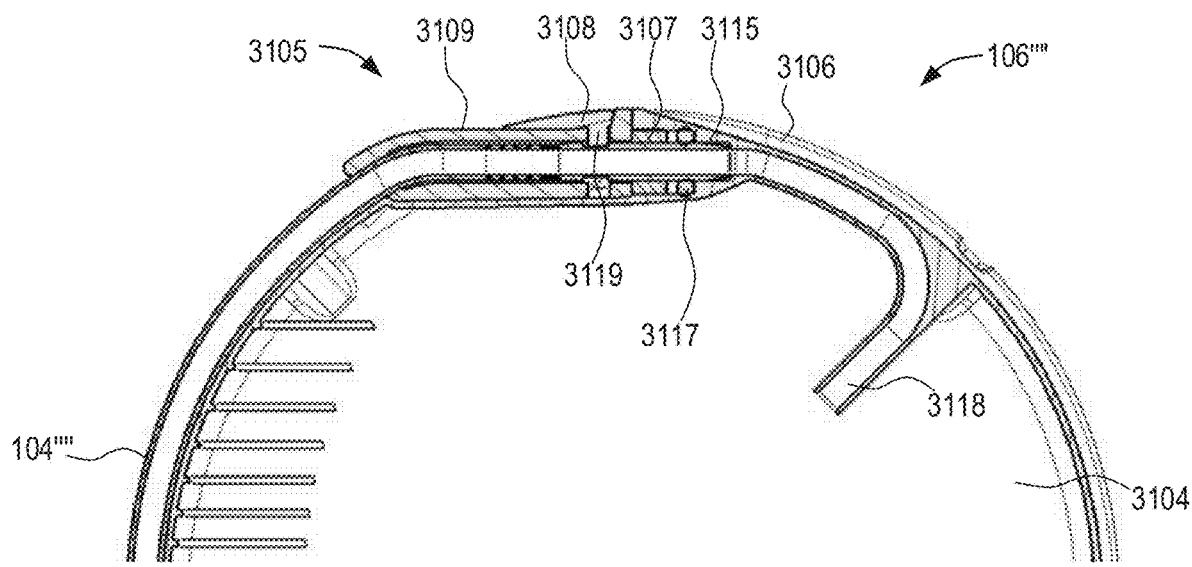

As shown in FIGS. 31A-31E, reservoir 106″″ may include septum 112″″ configured to be pierced to permit fluid communication within reservoir 106″″. Like reservoir 106″, reservoir 106″″ may include a septum chamber, internal drain tube, and liquid accumulation cavity, omitted herein for brevity. FIG. 31E illustrates main body 3106 with removable body 3108 and header connector 3109 removed. Removable body 3108 includes connection retention feature 3119 to maintain reliable connection between removeably body 3108 and main body 3106. As shown in FIG. 31F, reservoir 106″″ may have female connection feature 3115, and conduit connector 3105 may have a male connection feature 3107 for coupling. Moreover, reservoir 106″″ may include O-ring 3117, which may be a radial seal. As shown in FIG. 31F, O-ring 3117 may be positioned within main body 3106. This configuration permits a "non-splitable" introducer.

As further shown in FIG. 31F, reservoir 106″″ may include snorkel 3118 within internal chamber 3104. Snorkel 3118 is in fluid communication with the proximal end of conduit 104″″ (e.g., via conduit connector 3105). Snorkel 3118 has an opening configured to be positioned away from liquid accumulation within internal chamber 3104. In this manner, as gas travels into and out of reservoir via snorkel 3118 into conduit 104″″ responsive to pressure changes during the cardiac cycle, liquid accumulated within internal chamber 3104 is not moved, or is minimally moved, out of the reservoir along with the gas.

Figure 32:
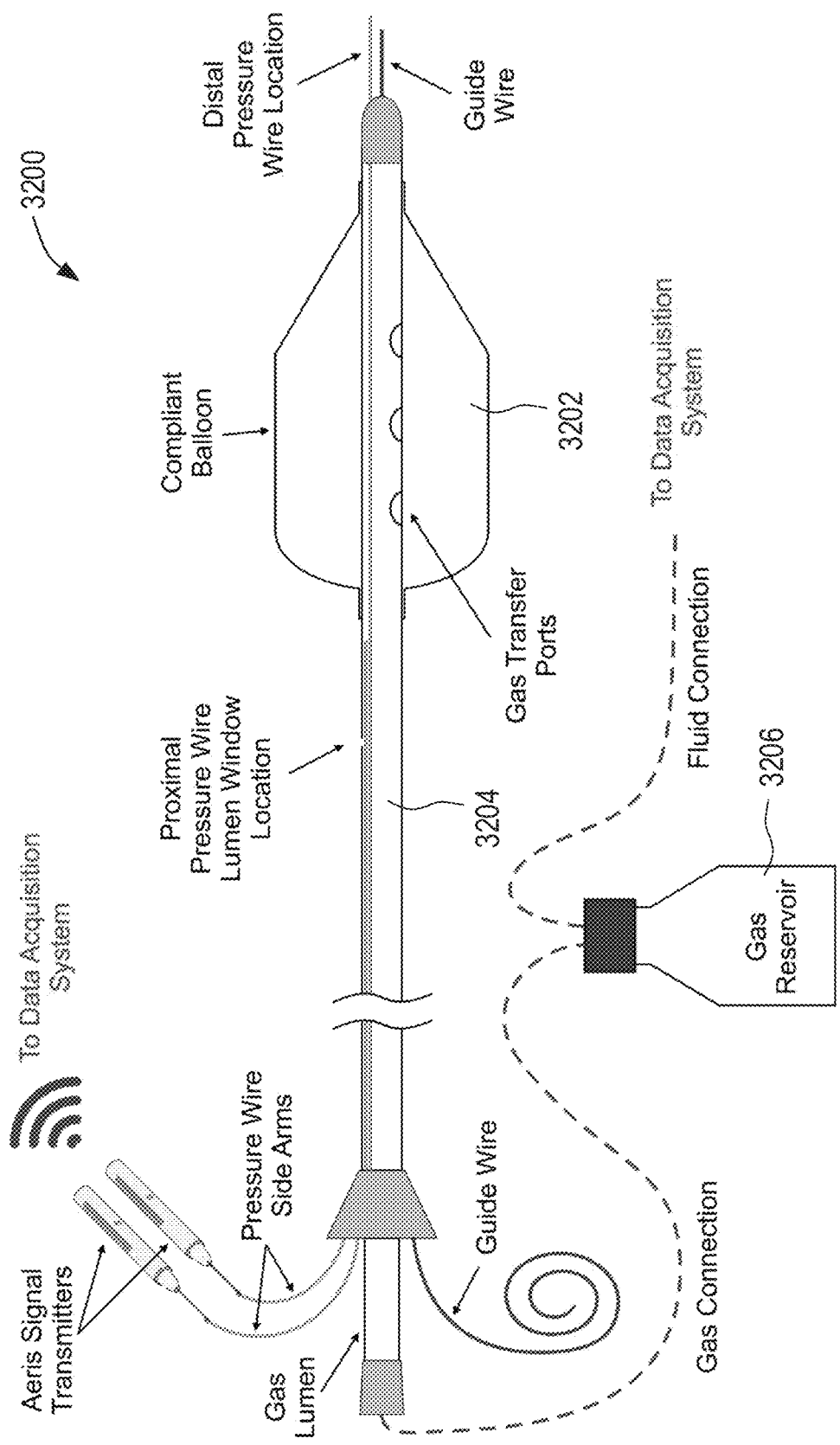
FIG. 32 illustrates exemplary components of a system that may be used for an acute treatment.

FIG. 32 illustrates exemplary components of system 3200 that may be used in an acute setting (e.g., used for hours or days (e.g., max 30 or 60 days) while in hospital care (e.g., in the ICU)). System 3200 includes compliant member 3202 and conduit 3204, each of which may be constructed similar to the respective components described above. System 3200 has reservoir 3206 that is constructed to remain external to the patient. In addition, system 3200 does not include the anchor in this illustrated example. System 3200 further may include embedded pressure wires to measure hemodynamics real time. As illustrated, system 3200 includes a distal pressure wire that extends distal to compliant member 3202 and is configured to measure pressure within the body lumen (e.g., pulmonary artery) distal to compliant member 3202. System 3200 further includes a proximal pressure wire that extends to a window in conduit 3204 located proximal to compliant member 3202 and is configured to measure pressure within the body lumen (e.g., pulmonary artery) proximal to compliant member 3202. The pressure wires may extend through one or more lumens within conduit 3204. The sensed parameters may be transferred to a data acquisition system and utilized in the manner described in U.S. Pat. No. 8,876,850 to Vollmers. The pressure wires may be commercially available devices, such as the PressureWire Aeris by St. Jude Medical. Conduit 3204 is also designed to receive a guide wire via a lumen in the conduit. Conduit 3204 also has one or more gas lumens connected to the gas transfer ports within compliant member 3202 so that gas can flow between compliant member 3202 and reservoir 3206 via conduit 3204. In this manner, compliant member 3202 transitions between the expanded state and the collapsed state responsive to pressure change in the body lumen to provide a beneficial result, as described above.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for reducing pulsatile pressure within a blood vessel, the system comprising:
a fluid reservoir;
a conduit configured to be coupled to the fluid reservoir, the conduit comprising a distal tip;
a balloon disposed on a distal portion of the conduit, the balloon configured to implanted in the blood vessel and fluidicly coupled to the fluid reservoir via the conduit;
an anchor comprising an expandable structure configured to engage the blood vessel in a deployed state, and a docking hub configured to detachably engage the distal tip of the conduit, the expandable structure comprising a metal frame configured to permit blood flow therethrough in the deployed state;
a guidewire configured to be slidably moveable through a lumen of the conduit, the guidewire comprising a distal end having a first geometry; and
a screw head positioned within a lumen of the conduit at the distal tip of the conduit, the screw head comprising a passageway having a second geometry sized and shaped to receive the first geometry of the distal end of the guidewire, and a threaded distal portion configured to detachably engage with the docking hub of the anchor,
wherein, when the distal end of the guidewire is engaged with the screw head, the distal end of the guidewire is configured to be actuated by rotating the guidewire to thereby rotate the threaded distal portion to disengage the distal tip of the conduit from the docking hub of the anchor such that the balloon and the conduit are removable from the blood vessel while the anchor remains implanted.

2. The system of claim 1, further comprising a seal positioned within the lumen of the conduit proximal to the distal tip, the seal configured to fluidicly isolate the fluid reservoir, the balloon, and the conduit when the conduit is coupled to the fluid reservoir and the balloon, the seal comprising a passageway for receiving the guidewire therethrough.

3. The system of claim 2, further comprising a pusher configured to be slidably moveable through the lumen of the conduit, the pusher having a lumen sized and shaped to receive the guidewire therethrough to stabilize the guidewire when the distal end of the guidewire is actuated to disengage the distal tip of the conduit from the docking hub of the anchor.

4. The system of claim 3, further comprising a pusher stop positioned within the lumen of the conduit proximal to the seal, the pusher stop comprising a passageway sized and shaped to receive a distal portion of the pusher to provide counter-torque when the guidewire is rotated to disengage the distal tip of the conduit from the docking hub of the anchor.

5. The system of claim 3, wherein the passageway of the seal comprises a conical proximal portion and a linear distal portion.

6. The system of claim 1, further comprising a housing at least partially positioned within the lumen of the conduit at the distal tip of the conduit, the housing having a cavity sized and shaped to rotatably receive at least a portion of the screw head.

7. The system of claim 1, wherein the fluid reservoir comprises:
a main body having an interior chamber and a groove extending circumferentially along an outer surface of the main body, the groove sized and shaped to receive at least a portion of the conduit; and
a header removably coupled to the main body via a clip attachment, the header configured to receive a proximal end of the conduit to fluidicly couple the conduit and the interior chamber of the fluid reservoir.

8. A system for reducing pulsatile pressure within a blood vessel, the system comprising:
a fluid reservoir;
a first conduit configured to be coupled to the fluid reservoir;
a balloon disposed on a distal portion of the first conduit, the balloon configured to implanted in the blood vessel and fluidicly coupled to the fluid reservoir via the first conduit;
a second conduit extending distally from the first conduit, the second conduit comprising a lumen and a distal tip;
an anchor comprising an expandable structure configured to transition between a contracted state within the lumen of the second conduit and an expanded state to engage the blood vessel, and a docking hub coupled to the expandable structure and configured to be slidably moveable within the second conduit, the docking hub having an asymmetric passageway; and
a guidewire configured to be slidably moveable through a lumen of the first and second conduits, the guidewire comprising a proximal portion having a first geometry, a distal portion having a second geometry offset from the first geometry, and a neck portion therebetween,
wherein the distal portion of the guidewire is slidably moveable through the asymmetric passageway of the docking hub while the guidewire is in a first orientation until the neck portion is disposed within the asymmetric passageway, and when the guidewire is rotated to a second orientation offset from the first orientation while the neck portion of the guidewire is positioned within the asymmetric passageway, the proximal portion of the guidewire is slidably moveable through the asymmetric passageway while the distal portion of the guidewire is not slidably moveable through the asymmetric passageway, and
wherein the distal tip of the second conduit is configured to prevent distal movement of the docking hub beyond the distal tip of the second conduit.

9. The system of claim 8, wherein, when the guidewire is in the second orientation and the distal portion of the guidewire is distal to the docking hub, proximal movement of the guidewire causes the distal portion of the guidewire to engage the docking hub and retract the docking hub within the lumen of the second conduit to thereby transition the expandable structure from the expanded state to the contracted state within the lumen of the second conduit.

10. The system of claim 8, wherein, when the guidewire is in the first orientation and the expandable structure is in the contracted state within the lumen of the second conduit, distal movement of the guidewire causes the proximal portion of the guidewire to engage the docking hub and push the docking hub distally within the lumen of the second conduit to thereby transition the expandable structure from the contracted state to the expanded state within the blood vessel.

11. The system of claim 8, wherein the first geometry of the proximal portion comprises a first flat surface, and wherein the second geometry of the distal portion comprises a second flat surface offset from the first flat surface by 90 degrees.

12. The system of claim 8, wherein the distal tip of the second conduit converges radially inward such that a distal end of the distal tip has a diameter less than a diameter of the docking hub to thereby prevent distal movement of the docking hub beyond the distal tip of the second conduit.

13. The system of claim 8, wherein the distal tip of the second conduit comprises a lip that extends radially inward, and wherein the docking hub comprises a retention ring that engages with the lip to thereby prevent distal movement of the docking hub beyond the distal tip of the second conduit.

14. The system of claim 8, wherein the distal tip of the second conduit comprises one or more crossbars extending across an opening of the distal tip to thereby prevent distal movement of the docking hub beyond the distal tip of the second conduit.

15. The system of claim 8, wherein the distal tip of the second conduit comprises one or more tabs that extend radially inward to thereby prevent distal movement of the docking hub beyond the distal tip of the second conduit.

16. The system of claim 8, further comprising a seal positioned between the first conduit and the second conduit, the seal configured to fluidicly isolate the fluid reservoir, the balloon, and the first conduit when the first conduit is coupled to the fluid reservoir and the balloon, the seal comprising a passageway for receiving the guidewire therethrough.

17. A method for reducing pulsatile pressure within a blood vessel of a patient, the method comprising:
   delivering a distal portion of a conduit within a blood vessel, the distal portion having a balloon disposed thereon;
   deploying an anchor coupled to a distal tip of the conduit via a docking hub detachably engaged with a threaded distal portion of a screw head positioned within a lumen of the conduit, the anchor comprising a metal frame configured to permit blood flow therethrough;
   coupling a proximal portion of the conduit to a fluid reservoir;
   implanting the reservoir within the patient;
   decoupling the proximal portion of the conduit from the fluid reservoir;
   inserting a guidewire through a lumen of the conduit to engage a distal end of the guidewire having a first geometry with a passageway of the screw head having a second geometry; and
   actuating the distal end of the guidewire by rotating the guidewire to thereby rotate the threaded distal portion to disengage the distal tip of the conduit from the docking hub of the anchor such that the balloon and the conduit are removable from the blood vessel while the anchor remains implanted.

* * * * *